(12) United States Patent
Shigeta et al.

US008889732B2

(10) Patent No.: US 8,889,732 B2
(45) Date of Patent: Nov. 18, 2014

(54) FUSED HETEROCYCLIC COMPOUNDS AND THROMBOPOIETIN RECEPTOR ACTIVATORS

(75) Inventors: Yukihiro Shigeta, Funabashi (JP); Shingo Umezawa, Funabashi (JP); Shunsuke Iwamoto, Funabashi (JP); Takanori Nakamura, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 1 day.

(21) Appl. No.: 13/503,560

(22) PCT Filed: Oct. 22, 2010

(86) PCT No.: PCT/JP2010/068754
§ 371 (c)(1),
(2), (4) Date: Apr. 23, 2012

(87) PCT Pub. No.: WO2011/049213
PCT Pub. Date: Apr. 28, 2011

(65) Prior Publication Data
US 2012/0209005 A1 Aug. 16, 2012

(30) Foreign Application Priority Data
Oct. 23, 2009 (JP) ................................. 2009-244852
Aug. 12, 2010 (JP) ................................. 2010-181032

(51) Int. Cl.
| A61K 31/38 | (2006.01) |
| C07D 333/32 | (2006.01) |
| C07D 231/18 | (2006.01) |
| C07D 333/38 | (2006.01) |
| C07D 401/12 | (2006.01) |
| C07D 409/12 | (2006.01) |
| C07D 409/14 | (2006.01) |
| C07D 409/04 | (2006.01) |
| C07D 333/40 | (2006.01) |

(52) U.S. Cl.
CPC ............ *C07D 409/14* (2013.01); *C07D 231/18* (2013.01); *C07D 333/38* (2013.01); *C07D 401/12* (2013.01); *C07D 409/12* (2013.01); *C07D 333/32* (2013.01); *C07D 409/04* (2013.01); *C07D 333/40* (2013.01)
USPC ........... 514/445; 514/444; 514/446; 514/448; 549/60; 549/62; 549/65; 549/68; 549/70; 549/74; 549/78; 549/80

(58) Field of Classification Search
CPC ............. C07D 333/32; C07D 333/38
USPC .................. 549/60, 62, 68, 70, 74, 78, 80, 65; 514/444, 445, 446, 448
See application file for complete search history.

(56) References Cited

U.S. PATENT DOCUMENTS

| 6,339,046 B1 * | 1/2002 | Nebel et al. ................... 504/280 |
| 7,241,783 B2 | 7/2007 | Duffy et al. ................... 514/369 |
| 7,351,841 B2 | 4/2008 | Owada et al. ................... 549/62 |
| 7,576,115 B2 | 8/2009 | Owada et al. ................. 514/406 |
| 7,960,425 B2 | 6/2011 | Miyaji et al. .................. 514/406 |
| 7,968,542 B2 | 6/2011 | Miyaji et al. ................ 514/231.5 |
| 8,026,368 B2 | 9/2011 | Miyaji et al. ................ 546/276.1 |
| 8,053,453 B2 | 11/2011 | Miyaji et al. .................. 514/381 |
| 8,093,251 B2 | 1/2012 | Miyaji et al. ............. 514/254.05 |
| 8,134,013 B2 | 3/2012 | Miyaji et al. .................. 548/527 |
| 8,318,796 B2 * | 11/2012 | Owada et al. ................. 514/445 |
| 8,552,031 B2 * | 10/2013 | Miyaji et al. .................. 514/318 |
| 2009/0281317 A1 | 11/2009 | Miyaji et al. .................. 544/379 |
| 2011/0077290 A1 | 3/2011 | Owada et al. ................. 514/445 |

FOREIGN PATENT DOCUMENTS

| JP | 10 72492 | 3/1998 |
| JP | 2004 520302 | 7/2004 |
| JP | 2009 501131 | 1/2009 |
| WO | 96 40189 | 12/1996 |
| WO | 96 40750 | 12/1996 |
| WO | 98 25965 | 6/1998 |
| WO | 02 49413 | 6/2002 |

(Continued)

OTHER PUBLICATIONS

Braga et al. "Making crystals..." Chem Commun J. Roy. Soc. Chem. p. 3635-3645 (2005).*

(Continued)

*Primary Examiner* — Celia Chang
(74) *Attorney, Agent, or Firm* — Oblon, Spivak, McClelland, Maier & Neustadt, L.L.P.

(57) ABSTRACT

Fused heterocyclic compounds useful for prevention, treatment or improvement of diseases against which activation of the thrombopoietin receptor is effective are provided.

A compound represented by the formula (I) (wherein $R^1$ is an aryl group fused to a saturated ring or the like, A, B, $L^1$, $R^2$, $L^2$, $L^3$, Y, $L^4$, $R^3$ and X are defined in the description), a tautomer, prodrug or a pharmaceutically acceptable salt of the compound or a solvate thereof.

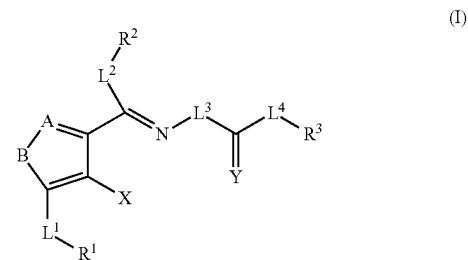

(I)

4 Claims, No Drawings

(56) References Cited

FOREIGN PATENT DOCUMENTS

| WO | 2004 108683 | 12/2004 |
|---|---|---|
| WO | 2006 062240 | 6/2006 |
| WO | 2007 010954 | 1/2007 |
| WO | WO 2009/092276 A1 | 7/2009 |
| WO | 2009 103218 | 8/2009 |

OTHER PUBLICATIONS

Chasset et al. "Cyclic compounds . . . " CA157:577187 (2012).*
"Improper Markush" Fed. Reg. v.76(27) p. 7162-7175, slide 1, 64-67 (2011).*
Patani et al. "Bioisosterism: a rational . . . " Chem. Rev. 96, p. 3147-3176 (1996).*
Prodrug "Am. Heritage Dictionary" p. 1 (internet) (2013).*
Seddon "Psudopolymor . . . " Crystal Growth and Design v.4(6) 1087 (2004).*
Vippagunta et al. "Crystalline solids . . . " Adv. Drug Del. Rev. v.48. p. 3-26 (2001).*
Wolff "Burger's medicinal chemistry . . . " p. 975-977 (1995).*
Zohair et al. "Synthesis of . . . " CA105:208698 (1986).*
Alves et al. "Evidence from the gas . . . " J. Mol. Spectroscopy, v.77(1) p. 124 (1979).*
Baulch et al. "rate constants . . . " J. Chem. Soc. Faraday Trans 2, 85(11) 1819-1826 (1989).*
Cardier, J.E., "Effects of Megakaryocyte Growth and Development Factor (Thrombopoietin on Liver Endothelial Cells in Vitro," Microvascular Research, vol. 58, pp. 108-113, (1999).
Brizzi, M.F., et al., "Thrombopoietin Stimulates Endothelial Cell Motility and Neoangiogenesis by a Platelet-Activating Factor-Dependent Mechanism," Circulation Research, vol. 84, pp. 785-796, (1999).
"Cell Migration, Growth Factors, and Chemokines in Stem Cell Biology," Blood, vol. 98, pp. 71a-72a, (2001).
International Search Report Issued Jan. 25, 2011 in PCT/JP10/68754 Filed Oct. 22, 2010.
Extended European Search Report issued Feb. 15, 2013 in European patent Application No. 10825062.2.

* cited by examiner

FUSED HETEROCYCLIC COMPOUNDS AND THROMBOPOIETIN RECEPTOR ACTIVATORS

TECHNICAL FIELD

The present invention relates to preventive, therapeutic and improving agents having affinity for and agonistic action on the thrombopoietin receptor for diseases against which activation of the thrombopoietin receptor is effective. Specifically, it relates to pharmaceutical compositions comprising compounds which increase platelets through stimulation of differentiation and proliferation of hematopoietic stem cells, megakaryocytic progenitor cells and megakaryocytes, compounds for therapeutic angiogenesis that stimulate differentiation and proliferation of vascular endothelial cells and endothelial progenitor cells or compounds with anti-arteriosclerosis action.

BACKGROUND ART

Thrombopoietin is a cytokine consisting of 332 amino acids that increases platelet production by stimulating differentiation and proliferation of hematopoietic stem cells, megakaryocytic progenitor cells and megakaryocytes mediated by its receptor and therefore is promising as a drug for hematological disorders. Recent reports that it stimulates differentiation and proliferation of vascular endothelial cells and endothelial progenitor cells have raised expectations of therapeutic angiogenesis, anti-arteriosclerosis and prevention of cardiovascular events (for example, non-patent document 1, non-patent document 2 and non-patent document 3).

Biologically active substances which have been known so far to regulate platelet production through the thrombopoietin receptor include, in addition to thrombopoietin itself, low molecular weight peptides having affinity for the thrombopoietin receptor (for example, patent document 1, patent document 2, patent document 3 and patent document 4).

As a result of search for nonpeptidic low molecular weight compounds that increase platelet production mediated by the thrombopoietin receptor, low molecular weight compounds having affinity for the thrombopoietin receptor have been reported (for example, patent document 5 to patent document 9).

(1) International Laid-open Patent Application filed by SmithKline Beecham Corp (patent document 5)

(2) Japanese Laid-open Patent Applications filed by Nissan Chemical Industries, Ltd. (patent documents 6 to 8)

(3) International Laid-open Patent Application filed by SHANGHAI HENGRUI PHARMACEUTICAL CO., LTD. (patent document 9)

PRIOR ART DOCUMENTS

Patent Document(s)

Patent Document 1: JP-A-10-72492
Patent Document 2: WO96/40750
Patent Document 3: WO96/40189
Patent Document 4: WO98/25965
Patent Document 5: WO02/49413
Patent Document 6: WO04/108683
Patent Document 7: WO06/062240
Patent Document 8: WO07/010,954
Patent Document 9: WO09/103,218

Non-Patent Document(s)

Non-Patent Document 1: Microvasc. Res., 1999: 58, p. 108-113

Non-Patent Document 2: Circ. Res., 1999: 84, p. 785-796
Non-Patent Document 3: Blood 2001: 98, p. 71a-72a

DISCLOSURE OF INVENTION

Technical Problem

Thrombopoietin and low molecular weight peptides having affinity for the thrombopoietin receptor are likely to be easily degraded in the gastrointestinal tract and are usually difficult to orally administer. As to thrombopoietin itself, the appearance of anti-thrombopoietin antibodies have been reported.

Besides, though it is probably possible to orally administer nonpeptidic low molecular weight compounds, sufficient reports have not been made about it.

Therefore, orally administrable low molecular weight compounds having excellent affinity for and agonistic action on the thrombopoietin receptor as preventive, therapeutic and improving agents for diseases against which activation of the thrombopoietin receptor is effective have been demanded. Specifically, novel low molecular weight compounds which can serve as platelet increasing agents or increasing agents for other blood cells by stimulating differentiation and proliferation of hematopoietic stem cells, megakaryocytic progenitor cells and megakaryocytes, low molecular weight compounds which can be used for therapeutic angiogenesis by stimulating endothelial cells and endothelial progenitor cells or novel compounds which can be used as preventive and therapeutic agents for arteriosclerosis have been demanded.

Solution to Problem

The present inventors conducted extensive research to find low molecular weight compounds having affinity for and agonistic action on the thrombopoietin receptor, and as a result, found that the compounds of the present invention have high affinity and agonistic action which enable them to show potent platelet increasing action by stimulating differentiation and proliferation of megakaryocytic progenitor cells and megakaryocytes. The present invention was accomplished on the basis of this discovery.

Namely, the present invention provides:

(1) A compound represented by the formula (I):

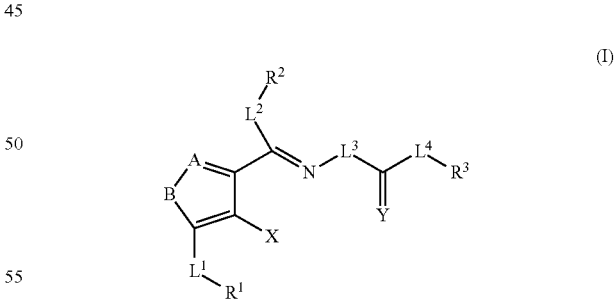

wherein A is a nitrogen atom or $CR^4$ (wherein $R^4$ is a hydrogen atom, a carboxy group, a carbamoyl group, a sulfamoyl group, a phosphono group, a sulfo group, a tetrazolyl group, a formyl group, a nitro group, a cyano group, a halogen atom, a $C_{1-6}$ alkyl group, a $C_{2-6}$ alkenyl group, a $C_{2-6}$ alkynyl group, a mono-$C_{1-6}$ alkylaminocarbonyl group, a di-$C_{1-6}$ alkylaminocarbonyl group, a $C_{1-6}$ alkylsulfonyl group, a $C_{2-14}$ aryl group or a $C_{2-9}$ heterocyclyl group (the $C_{1-6}$ alkyl group, the $C_{2-6}$ alkenyl group, the $C_{2-6}$ alkynyl group, the mono-$C_{1-6}$ alkylaminocarbonyl group, the di-$C_{1-6}$ alkylaminocarbonyl group, the $C_{1-6}$ alkylsulfonyl group, the $C_{2-14}$ aryl group and the $C_{2-9}$ heterocyclyl group are unsubstituted or substituted with one or more identical or different substituents selected from a substituent set $V^1$)), B is an oxygen atom, a sulfur atom or $NR^5$ (wherein $R^5$ is a hydrogen atom, a $C_{1-6}$ alkyl group, a $C_{2-6}$ alkenyl group, a $C_{2-6}$ alkynyl group or a $C_{1-6}$ alkylcarbonyl group (the $C_{1-6}$ alkyl group, the $C_{2-6}$ alkenyl group, the $C_{2-6}$ alkynyl group and the $C_{1-6}$ alkylcarbonyl group are unsubstituted or substituted with one or more identical or different substituents selected from a substituent set $V^1$)) (provided that when A is a nitrogen atom, B is not NH), $R^1$ is a $C_{2-14}$ aryl group fused to a $C_{3-10}$ cycloalkenyl group, a $C_{2-14}$ aryl group fused to a $C_{2-9}$ heterocyclyl group or a $C_{2-14}$ aryl group fused to a $C_{3-10}$ cyloalkyl group (the $C_{2-14}$ aryl group fused to a $C_{3-10}$ cycloalkenyl group, the $C_{2-14}$ aryl group fused to a $C_{2-9}$ heterocyclyl group and the $C_{2-14}$ aryl group fused to a $C_{3-10}$ cycloalkyl group are unsubstituted or substituted with one or more identical or different substituents selected from a substituent set $V^1$), each of $L^1$, $L^2$, $L^3$ and $L^4$ is independently a single bond, a $C_{1-6}$ alkylene group, a $C_{2-6}$ alkenylene group, a $C_{2-6}$ alkynylene group (the $C_{1-6}$ alkylene group, the $C_{2-6}$ alkenylene group and the $C_{2-6}$ alkynylene group are unsubstituted or substituted with one or more identical or different substituents selected from a substituent set $V^1$), $CR^6R^7$ (wherein $R^6$ and $R^7$ mean, together with each other, an oxo group or a thioxo group), an oxygen atom, a sulfur atom or $NR^8$ (wherein $R^8$ is a hydrogen atom, a $C_{1-6}$ alkyl group, a $C_{2-6}$ alkenyl group, a $C_{2-6}$ alkynyl group or a $C_{1-6}$ alkylcarbonyl group (the $C_{1-6}$ alkyl group, the $C_{2-6}$ alkenyl group, the $C_{2-6}$ alkynyl group and the $C_{1-6}$ alkylcarbonyl group are unsubstituted or substituted with one or more identical or different substituents selected from a substituent set $V^1$)), X is $OR^9$, $SR^9$ or $NR^{10}R^{11}$ (wherein each of $R^9$, $R^{16}$ and $R^{11}$ is independently a hydrogen atom, a $C_{1-6}$ alkyl group, a $C_{2-6}$ alkenyl group, a $C_{2-6}$ alkynyl group, a $C_{1-6}$ alkylsulfonyl group or a $C_{1-6}$ alkylcarbonyl group (the $C_{1-6}$ alkyl group, the $C_{2-6}$ alkenyl group, the $C_{2-6}$ alkynyl group, the $C_{1-6}$ alkylsulfonyl group and the $C_{1-6}$ alkylcarbonyl group are unsubstituted or substituted with one or more identical or different substituents selected from a substituent set $V^1$)), $R^2$ is a hydrogen atom, a $C_{1-6}$ alkyl group, a $C_{2-6}$ alkenyl group, a $C_{2-6}$ alkynyl group or a $C_{2-14}$ aryl group (the $C_{1-6}$ alkyl group, the $C_{2-6}$ alkenyl group, the $C_{2-6}$ alkynyl group and the $C_{2-14}$ aryl group are unsubstituted or substituted with one or more identical or different substituents selected from a substituent set $V^1$), Y is an oxygen atom, a sulfur atom or $NR^{12}$ (wherein $R^{12}$ is a hydrogen atom, a hydroxy group, a cyano group, a $C_{1-6}$ alkyl group, a $C_{2-6}$ alkenyl group, a $C_{2-6}$ alkynyl group or a $C_{1-6}$ alkylcarbonyl group (the $C_{1-6}$ alkyl group, the $C_{2-6}$ alkenyl group, the $C_{2-6}$ alkynyl group and the $C_{1-6}$ alkylcarbonyl group are unsubstituted or substituted with one or more identical or different substituents selected from a substituent set $V^1$)), $R^3$ is a $C_{1-6}$ alkyl group, a $C_{2-9}$ heterocyclyl group, a $C_{3-10}$ cycloalkyl group, a $C_{2-14}$ aryl group, a $C_{2-14}$ aryl group fused to a $C_{3-10}$ cycloalkenyl group, a $C_{2-14}$ aryl group fused to a $C_{2-9}$ heterocyclyl group or a $C_{2-14}$ aryl group fused to a $C_{3-10}$ cycloalkyl group (the $C_{1-6}$ alkyl group, the $C_{2-9}$ heterocyclyl group, the $C_{3-10}$ cycloalkyl group, the $C_{2-14}$ aryl group, a $C_{2-14}$ aryl group fused to a $C_{3-10}$ cycloalkenyl group, the $C_{2-14}$ aryl group fused to a $C_{2-9}$ heterocyclyl group and the $C_{2-14}$ aryl group fused to a $C_{3-10}$ cycloalkyl group are unsubstituted or substituted with one or more identical or different substituents selected from a substituent set $V^1$), and the substituent set $V^1$ consists of phosphono groups, sulfo groups, tetrazolyl groups, formyl groups, nitro groups, cyano groups, halogen atoms, $C_{1-6}$ alkyl groups, $C_{2-6}$ alkenyl groups, $C_{2-6}$ alkynyl groups, $C_{2-14}$ aryl groups, $C_{2-9}$ heterocyclyl groups (the $C_{1-6}$ alkyl groups, the $C_{2-6}$ alkenyl groups, the $C_{2-6}$ alkynyl groups, the $C_{2-14}$ aryl groups and the $C_{2-9}$ heterocyclyl groups are unsubstituted or substituted with one or more identical or different substituents selected from carboxy groups, carbamoyl groups, sulfamoyl groups, phosphono groups, sulfo groups, tetrazolyl groups, formyl groups, nitro groups, cyano groups, halogen atoms, $C_{1-6}$ alkyl groups, $C_{1-3}$ haloalkyl groups, $C_{1-6}$ alkoxy groups, $C_{1-3}$ haloalkoxy groups, hydroxy groups, amino groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{1-6}$ alkylthio groups, $C_{1-6}$ alkylsulfonyl groups, $C_{2-14}$ aryl groups and $C_{2-9}$ heterocyclyl groups (the $C_{2-14}$ aryl groups and the $C_{2-9}$ heterocyclyl groups are unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more $C_{1-6}$ alkyl groups, one or more $C_{1-6}$ haloalkyl groups, one or more $C_{1-6}$ alkoxy groups, one or more $C_{1-3}$ haloalkoxy groups, one or more hydroxy groups, one or more amino groups, one or more mono-$C_{1-6}$ alkylamino groups, one or more di-$C_{1-6}$ alkylamino groups, one or more mono-$C_{1-6}$ alkylaminocarbonyl groups (the mono-$C_{1-6}$ alkylaminocarbonyl groups are unsubstituted or substituted with one or more substituents selected from hydroxy groups, $C_{2-14}$ aryl groups and $C_{2-9}$ heterocyclyl groups), one or more di-$C_{1-6}$ alkylaminocarbonyl groups, one or more $C_{1-6}$ alkylcarbonylamino groups, one or more $C_{1-6}$ alkylthio groups or one or more $C_{1-6}$ alkylsulfonyl groups))

and the structures represented by the following formula (II):

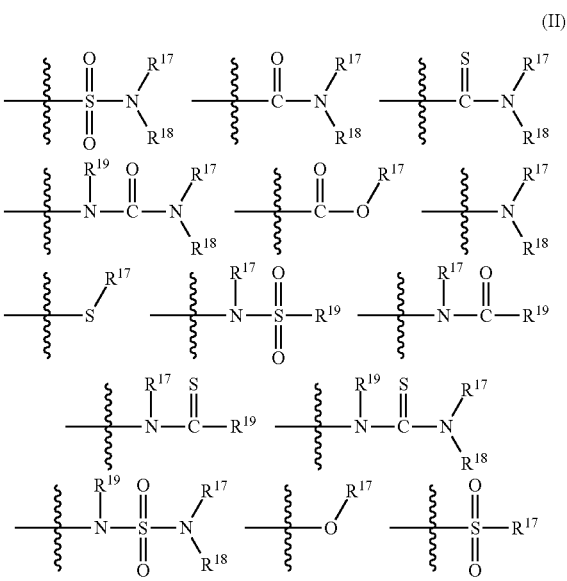

(wherein each of $R^{17}$, $R^{18}$ and $R^{19}$ is independently a hydrogen atom, a $C_{1-6}$ alkyl group, a $C_{2-6}$ alkenyl group, a $C_{2-6}$ alkynyl group, a $C_{2-9}$ heterocyclyl group or a $C_{2-14}$ aryl group (the $C_{1-6}$ alkyl group, the $C_{2-6}$ alkenyl group, the $C_{2-6}$ alkynyl group, the $C_{2-9}$ heterocyclyl group and the $C_{2-14}$ aryl group are unsubstituted or substituted with one or more identical different substituents selected from carboxy groups, carbamoyl groups, sulfamoyl groups, phosphono groups, sulfo groups, tetrazolyl groups, formyl groups, nitro groups, cyano groups, halogen atoms, $C_{1-6}$ alkyl groups, $C_{1-3}$ haloalkyl groups, $C_{1-6}$ alkoxy groups, $C_{1-3}$ haloalkoxy groups, hydroxy groups, amino groups, mono-$C_{1-6}$ alkylamino groups, di-$C_{1-6}$ alkylamino groups, mono-$C_{1-6}$ alkylaminocarbonyl groups, di-$C_{1-6}$ alkylaminocarbonyl groups, $C_{1-6}$ alkylcarbonylamino groups, $C_{1-6}$ alkylthio groups, $C_{1-6}$ alkylsulfonyl groups, $C_{2-14}$ aryl groups and $C_{2-9}$ heterocyclyl groups (the $C_{2-14}$ aryl groups and $C_{2-9}$ heterocyclyl groups are unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more $C_{1-6}$ alkyl groups, $C_{1-3}$ haloalkyl groups, one or more $C_{1-6}$ alkoxy groups, one or more $C_{1-3}$ haloalkoxy groups, one or more hydroxy groups, one or more amino groups, one or more mono-$C_{1-6}$ alkylamino groups, one or more di-$C_{1-6}$ alkylamino groups, one or more mono-$C_{1-6}$ alkylaminocarbonyl groups (the mono-$C_{1-6}$ alkylaminocarbonyl groups are unsubstituted or substituted with one or more substituents selected from hydroxy groups, $C_{2-14}$ aryl groups and $C_{2-6}$ heterocyclyl groups), one or more di-$C_{1-6}$ alkylaminocarbonyl groups, one or more $C_{1-6}$ alkylcarbonylamino groups, one or more $C_{1-6}$ alkylthio group or one or more $C_{1-6}$ alkylsulfonyl groups)), or $NR^{17}R^{18}$, as a whole, means a $C_{2-6}$ nitrogen-containing heterocyclyl group (the $C_{2-6}$ nitrogen-containing heterocyclyl group is unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more $C_{1-6}$ alkyl groups, one or more $C_{1-3}$ haloalkyl groups, one or more $C_{1-6}$ alkoxy groups, one or more $C_{1-3}$ haloalkoxy groups, one or more hydroxy groups, one or more amino groups, one or more mono-$C_{1-6}$ alkylamino groups, one or more di-$C_{1-6}$ alkylamino groups, one or more mono-$C_{1-6}$ alkylaminocarbonyl groups (the mono-$C_{1-6}$ alkylaminocarbonyl groups are unsubstituted or substituted with one or more substituents selected from hydroxy groups, $C_{2-14}$ aryl groups and $C_{2-9}$ heterocyclyl groups), di-$C_{1-6}$ alkylaminocarbonyl groups, one or more $C_{1-6}$ alkylcarbonylamino groups, one or more $C_{1-6}$ alkylthio group or one or more $C_{1-6}$ alkylsulfonyl groups)), a tautomer, prodrug or a pharmaceutically acceptable salt of the compound or a solvate thereof.

(2) The compound according to (1), wherein A is a nitrogen atom or $CR^4$ (wherein $R^4$ is a hydrogen atom, a halogen atom or a $C_{1-6}$ alkyl group (the $C_{1-6}$ alkyl group is unsubstituted or substituted with one or more halogen atoms)), and when A is a nitrogen atom, B is $NR^5$ (wherein $R^5$ is a $C_{1-6}$ alkyl group (the $C_{1-6}$ alkyl group is unsubstituted or substituted with one or more halogen atoms)) and when A is $CR^4$, B is a sulfur atom, $L^1$ and $L^2$ are single bonds, $L^3$ is $NR^8$ (wherein $R^8$ is a hydrogen atom or a $C_{1-6}$ alkyl group (the $C_{1-6}$ alkyl group is unsubstituted or substituted with one or more halogen atoms)), $L^4$ is a single bond or $NR^{13}$ (wherein $R^{13}$ is a hydrogen atom or a $C_{1-6}$ alkyl group (the $C_{1-6}$ alkyl group is unsubstituted or substituted with one or more halogen atoms)), $R^2$ is a hydrogen atom or a $C_{1-6}$ alkyl group (the $C_{1-6}$ alkyl group is unsubstituted or substituted with one or more halogen atoms), X is OH, Y is an oxygen atom or a sulfur atom, and $R^3$ is a $C_{2-9}$ heterocyclyl group or a $C_{2-14}$ aryl group (the $C_{2-9}$ heterocyclyl group and the $C_{2-14}$ aryl group are unsubstituted or substituted with one or more identical or different substituents selected from a substituent set $V^1$), a tautomer, prodrug or a pharmaceutically acceptable salt of the compound or a solvate thereof.

(3) The compound according to (2), wherein A is a nitrogen atom or CH, when A is a nitrogen atom, B is $NR^5$ (wherein $R^5$ is a $C_{1-6}$ alkyl group), and when A is CH, B is a sulfur atom, $L^3$ is NH, $L^4$ is a single bond or NH, $R^1$ is a phenyl group fused to a $C_{2-9}$ heterocyclyl group or a phenyl group fused to a $C_{3-10}$ cycloalkyl group, $R^2$ is a hydrogen atom or a $C_{1-6}$ alkyl group, Y is an oxygen atom or a sulfur atom, and $R^3$ is a $C_{4-6}$ nitrogen-containing heterocyclyl group or a $C_{4-6}$ aryl group (the $C_{4-5}$ nitrogen-containing heterocyclyl group and the $C_{4-6}$ aryl group are unsubstituted or substituted with one or two identical or different substituents selected from the group consisting of carboxy groups, nitro groups, halogen atoms, $C_{1-6}$ alkoxycarbonyl groups and $CONR^{14}R^{15}$ (wherein each of $R^{14}$ and $R^{15}$ is independently a hydrogen atom or a $C_{1-6}$ alkyl group (the $C_{1-6}$ alkyl group is unsubstituted or substituted with one or more $C_{4-6}$ aryl group) or $NR^{14}R^{15}$, as a whole, means a $C_{4-5}$ nitrogen-containing heterocyclyl group)), a tautomer, prodrug or a pharmaceutically acceptable salt of the compound or a solvate thereof.

(4) The compound according to (3), wherein $L^4$ is a single bond, Y is an oxygen atom, and $R^3$ is a thienyl group (the thienyl group is one substituent selected from the group consisting of a carboxy group, a $C_{1-6}$ alkoxycarbonyl group, a di-$C_{1-6}$ alkylaminocarbonyl group, a mono-$C_{1-6}$ alkylaminocarbonyl group (the mono-$C_{1-6}$ alkylaminocarbonyl group is substituted with a pyridyl group) and a pyrrolidine-1-carbonyl group) or a phenyl group (the phenyl group is substituted with a carboxy group or a $C_{1-6}$ alkoxycarbonyl group and may be further substituted with a nitro group), $L^4$ is a single bond, Y is a sulfur atom, and $R^3$ is a piperidinyl group (the piperidinyl group is unsubstituted or substituted with a carboxy group or a $C_{1-6}$ alkylcarbonyl group), or $L^4$ is NH, Y is a sulfur atom, and $R^3$ is a phenyl group (the phenyl group is a carboxy group or a $C_{1-6}$ alkoxycarbonyl group and may be further substituted with a halogen atom), a tautomer, prodrug or a pharmaceutically acceptable salt of the compound or a solvate thereof.

(5) The compound according to (2), wherein A is a nitrogen atom or CH, when A is a nitrogen atom, B is $NR^5$ (wherein $R^5$ is a $C_{1-6}$ alkyl group), and when A is CH, B is a sulfur atom, $L^3$ is NH, $L^4$ is a single bond or NH, $R^2$ is a hydrogen atom or a $C_{1-6}$ alkyl group, Y is an oxygen atom or a sulfur atom, and $R^3$ is a $C_{4-6}$ aryl group (the $C_{4-6}$ aryl group is substituted with one or two identical or different substituents selected from the group consisting of tetrazolyl groups and $CONR^{17}R^{18}$ (wherein $R^{17}$ is a hydrogen atom or a $C_{1-3}$ alkyl group, and $R^{18}$ is a $C_{1-6}$ alkyl group (the $C_{1-6}$ alkyl group is substituted with a $C_{4-6}$ aryl group (the $C_{4-6}$ aryl group is substituted with a mono-$C_{1-6}$ alkylaminocarbonyl group (the mono-$C_{1-6}$ alkylaminocarbonyl group is unsubstituted or substituted with a hydroxy group)))) and may be further substituted with one or two identical or different substituents selected from the group consisting of halogen atoms and nitro groups), a tautomer, prodrug or a pharmaceutically acceptable salt of the compound or a solvate thereof.

(6) The compound according to (5), wherein $L^4$ is a single bond, Y is an oxygen atom, and $R^3$ is a phenyl group (the phenyl group is substituted with a tetrazolyl group), or $L^4$ is NH, Y is a sulfur atom, and $R^3$ is a phenyl group (the phenyl group is substituted with a tetrazolyl group), a tautomer, prodrug or a pharmaceutically acceptable salt of the compound or a solvate thereof.

(7) The compound according to (5), wherein $L^4$ is a single bond, Y is an oxygen atom, and $R^3$ is a thienyl group (the thienyl group is substituted with a mono-$C_{1-6}$ alkylaminocarbonyl group (the mono-$C_{1-6}$ alkylaminocarbonyl group is substituted with a phenyl group (the phenyl group is substituted with a mono-$C_{1-6}$ alkylaminocarbonyl group (the mono-$C_{1-6}$ alkylaminocarbonyl group is substituted with a hydroxy group)))), a tautomer, prodrug or a pharmaceutically acceptable salt of the compound or a solvate thereof.

(8) The compound according to any one of (2) to (7), wherein $R^1$ is a phenyl group fused to a $C_{4-7}$ cycloalkyl group or a phenyl group fused to a $C_{3-5}$ oxygen-containing heterocyclyl group, a tautomer, prodrug or a pharmaceutically acceptable salt of the compound or a solvate thereof.

(9) The compound according to any one of (2) to (7), wherein $R^1$ is an indanyl group, a tetrahydronaphthyl group or a 2,3-dihydrobenzofuranyl group, a tautomer, prodrug or a pharmaceutically acceptable salt of the compound or a solvate thereof.

(10) The compound according to any one of (1) to (9), wherein A is a nitrogen atom, and B is $NR^5$ (wherein $R^5$ is a methyl group), a tautomer, prodrug or a pharmaceutically acceptable salt of the compound or a solvate thereof.

(11) The compound according to any one of (1) to (9), wherein A is CH, and B is a sulfur atom, a tautomer, prodrug or a pharmaceutically acceptable salt of the compound or a solvate thereof.

(12) A thrombopoietin receptor activator containing the compound as defined in any one of (1) to (11), a tautomer, prodrug or a pharmaceutically acceptable salt of the compound or a solvate thereof, as an active ingredient.

(13) A preventive, therapeutic or improving agent for diseases against which activation of the thrombopoietin receptor is effective, which contains the thrombopoietin receptor activator according to (12), as an active ingredient.

(14) A platelet increasing agent containing the thrombopoietin receptor activator according to (12), as an active ingredient.

(15) Medicament containing the compound according to any one of (1) to (11), a tautomer, prodrug or a pharmaceutically acceptable salt of the compound or a solvate thereof, as an active ingredient.

DESCRIPTION OF EMBODIMENT(S)

Now, the present invention will be described in further detail.

In the present invention, "n" denotes normal, "i" denotes iso, "s" denotes secondary, "t" or "tert" denotes tertiary, "c" denotes cyclo, "o" denotes ortho, "m" denotes meta, "p" denotes para, "Ph" denotes phenyl, "Py" denotes pyridyl, "Me" denotes methyl, "Et" denotes ethyl, "Pr" denotes propyl, "Bu" denotes butyl, "Boc" denotes tertiary-butoxycarbonyl, "Ms" denotes methanesulfonyl, "Tf" denotes trifluoromethanesulfonyl, and "MOM" denotes methoxymethyl.

First, the terms in the respective substituents in the present invention will be explained.

Herein, when the number of possible substituents on a certain moiety exceeds the number of the substitutable positions on the moiety, the number of substitutable positions defines the number of the upper limit of the number of substituents. When a heteroaryl group or a heterocyclyl group has a substituent, the substituent may be present on a ring-constituting carbon atom or a ring-constituting nitrogen atom.

As a halogen atom, fluorine, chlorine, bromine or iodine may be mentioned.

A $C_{1-3}$ alkyl group is an alkyl group containing one to three carbon atoms and may be linear, branched or a $C_3$ cycloalkyl group. As specific examples, a methyl group, an ethyl group, a n-propyl group, an i-propyl group and a c-propyl group may be mentioned.

A $C_{1-6}$ alkyl group is an alkyl group containing one to six carbon atoms and may be linear, branched or a $C_{3-6}$ cycloalkyl group. As specific examples, in addition to those mentioned above, a n-butyl group, an i-butyl group, a s-butyl group, a t-butyl group, a c-butyl group, a 1-methyl-c-propyl group, a 2-methyl-c-propyl group, a n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, a c-pentyl group, a 1-methyl-c-butyl group, a 2-methyl-c-butyl group, a 3-methyl-c-butyl group, a 1,2-dimethyl-c-propyl group, a 2,3-dimethyl-c-propyl group, a 1-ethyl-c-propyl group, a 2-ethyl-c-propyl group, a n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, a 1-ethyl-2-methyl-n-propyl group, a c-hexyl group, a 1-methyl-c-pentyl group, a 2-methyl-c-pentyl group, a 3-methyl-c-pentyl group, a 1-ethyl-c-butyl group, a 2-ethyl-c-butyl group, a 3-ethyl-c-butyl group, a 1,2-dimethyl-c-butyl group, a 1,3-dimethyl-c-butyl group, a 2,2-dimethyl-c-butyl group, a 2,3-dimethyl-c-butyl group, a 2,4-dimethyl-c-butyl group, a 3,3-dimethyl-c-butyl group, a 1-n-propyl-c-propyl group, a 2-n-propyl-c-propyl group, a 1-i-propyl-c-propyl group, a 2-i-propyl-c-propyl group, a 1,2,2-trimethyl-c-propyl group, a 1,2,3-trimethyl-c-propyl group, a 2,2,3-trimethyl-c-propyl group, a 1-ethyl-2-methyl-c-propyl group, a 2-ethyl-1-methyl-c-propyl group, a 2-ethyl-2-methyl-c-propyl group, a 2-ethyl-3-methyl-c-propyl group and the like may be mentioned.

A $C_{1-3}$ haloalkyl group is a $C_{1-3}$ alkyl group such as those mentioned above which is substituted with one or more halogen atoms. As specific examples, a chloromethyl group, a trifluoromethyl group, a difluoromethyl group and the like may be mentioned.

A $C_{1-6}$ alkylene group is a bivalent group obtained by removing a hydrogen atom from the above-mentioned $C_{1-6}$ alkyl group and may be a linear, branched or cyclic alkylene containing one to six carbon atoms. For example, a methylene group, an ethylene group, a propylene group, an isopropylene group, a c-propylene group, an ethylpropylene group, a butylene group, an isobutylene group, a c-butylene group, an ethylbutylene group, a pentylene group, a c-pentylene group, a hexylene group or a c-hexylene group may be mentioned.

A $C_{3-10}$ cycloalkyl group is a cycloalkyl group containing three to ten carbon atoms and may have a fused polycyclic structure, a bridged cyclic structure or a spirocyclic structure.

As specific examples, a c-propyl group, a c-butyl group, a 1-methyl-c-propyl group, a 2-methyl-c-propyl group, a c-pentyl group, a 1-methyl-c-butyl group, a 2-methyl-c-butyl group, a 3-methyl-c-butyl group, a 1,2-dimethyl-c-propyl group, a 2,3-dimethyl-c-propyl group, a 1-ethyl-c-propyl group, a 2-ethyl-c-propyl group, a c-hexyl group, a 1-methyl-c-pentyl group, a 2-methyl-c-pentyl group, a 3-methyl-c-pentyl group, a 1-ethyl-c-butyl group, a 2-ethyl-c-butyl group, a 3-ethyl-c-butyl group, a 1,2-dimethyl-c-butyl group, a 1,3-dimethyl-c-butyl group, a 2,2-dimethyl-c-butyl group, a 2,3-dimethyl-c-butyl group, a 2,4-dimethyl-c-butyl group, a 3,3-dimethyl-c-butyl group, a 1-n-propyl-c-propyl group, a 2-n-propyl-c-propyl group, a 1-i-propyl-c-propyl group, a 2-i-propyl-c-propyl group, a 1,2,2-trimethyl-c-propyl group, a 1,2,3-trimethyl-c-propyl group, a 2,2,3-trimethyl-c-propyl group, a 1-ethyl-2-methyl-c-propyl group, a 2-ethyl-1-methyl-c-propyl group, a 2-ethyl-2-methyl-c-propyl group, a 2-ethyl-3-methyl-c-propyl group, a c-heptyl group, a c-octyl group, a c-nonyl group, a c-decyl group, the structures shown below and the like may be mentioned.

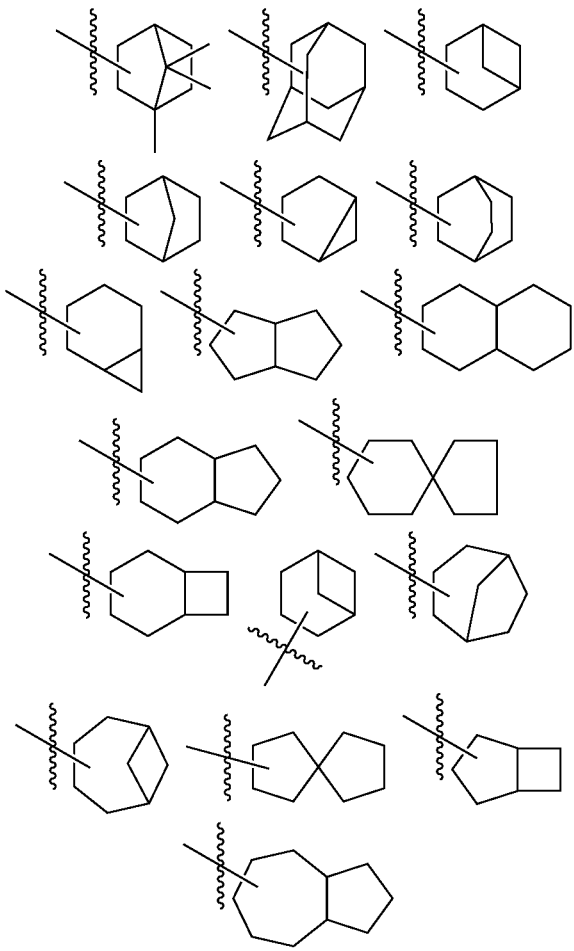

A $C_{4-7}$ cycloalkyl group means a cycloalkyl group containing four to seven carbon atoms. As specific examples, a c-butyl group, a c-pentyl group, a c-hexyl group, a c-heptyl group and the like may be mentioned.

A $C_{2-6}$ alkenyl group means a group obtained by converting arbitrary one, two or three bonds in the above-mentioned $C_{1-6}$ alkyl group (other than a methyl group) to double bonds, and may be linear, branched or a $C_{3-6}$ cycloalkenyl group. As specific examples, an ethenyl group, a 1-propenyl group, a 2-propenyl group, a 1-methyl-1-ethenyl group, a 1-butenyl group, a 2-butenyl group, a 3-butenyl group, a 2-methyl-1-propenyl group, a 2-methyl-2-propenyl group, a 1-ethylethenyl group, a 1-methyl-1-propenyl group, a 1-methyl-2-propenyl group, a 1-pentenyl group, a 2-pentenyl group, a 3-pentenyl group, a 4-pentenyl group, a 1-n-propylethenyl group, a 1-methyl-1-butenyl group, a 1-methyl-2-butenyl group, a 1-methyl-3-butenyl group, a 2-ethyl-2-propenyl group, a 2-methyl-1-butenyl group, a 2-methyl-2-butenyl group, a 2-methyl-3-butenyl group, a 3-methyl-1-butenyl group, a 3-methyl-2-butenyl group, a 3-methyl-3-butenyl group, a 1,1-dimethyl-2-propenyl group, a 1-i-propylethenyl group, a 1,2-dimethyl-1-propenyl group, a 1,2-dimethyl-2-propenyl group, a 1-c-pentenyl group, a 2-c-pentenyl group, a 3-c-pentenyl group, a 1-hexenyl group, a 2-hexenyl group, a 3-hexenyl group, a 4-hexenyl group, a 5-hexenyl group, a 1-methyl-1-pentenyl group, a 1-methyl-2-pentenyl group, a 1-methyl-3-pentenyl group, a 1-methyl-4-pentenyl group, a 1-n-butylethenyl group, a 2-methyl-1-pentenyl group, a 2-methyl-2-pentenyl group, a 2-methyl-3-pentenyl group, a 2-methyl-4-pentenyl group, a 2-n-propyl-2-propenyl group, a 3-methyl-1-pentenyl group, a 3-methyl-2-pentenyl group, a 3-methyl-3-pentenyl group, a 3-methyl-4-pentenyl group, a 3-ethyl-3-butenyl group, a 4-methyl-1-pentenyl group, a 4-methyl-2-pentenyl group, a 4-methyl-3-pentenyl group, a 4-methyl-4-pentenyl group, a 1,1-dimethyl-2-butenyl group, a 1,1-dimethyl-3-butenyl group, a 1,2-dimethyl-1-butenyl group, a 1,2-dimethyl-2-butenyl group, a 1,2-dimethyl-3-butenyl group, a 1-methyl-2-ethyl-2-propenyl group, a 1-s-butylethenyl group, a 1,3-dimethyl-1-butenyl group, a 1,3-dimethyl-2-butenyl group, a 1,3-dimethyl-3-butenyl group, a 1-i-butylethenyl group, a 2,2-dimethyl-3-butenyl group, a 2,3-dimethyl-1-butenyl group, a 2,3-dimethyl-2-butenyl group, a 2,3-dimethyl-3-butenyl group, a 2-i-propyl-2-propenyl group, a 3,3-dimethyl-1-butenyl group, a 1-ethyl-1-butenyl group, a 1-ethyl-2-butenyl group, a 1-ethyl-3-butenyl group, a 1-n-propyl-1-propenyl group, a 1-n-propyl-2-propenyl group, a 2-ethyl-1-butenyl group, a 2-ethyl-2-butenyl group, a 2-ethyl-3-butenyl group, a 1,1,2-trimethyl-2-propenyl group, a 1-t-butylethenyl group, a 1-methyl-1-ethyl-2-propenyl group, a 1-ethyl-2-methyl-1-propenyl group, a 1-ethyl-2-methyl-2-propenyl group, a 1-i-propyl-1-propenyl group, a 1-i-propyl-2-propenyl group, a 1-methyl-2-c-pentenyl group, a 1-methyl-3-c-pentenyl group, a 2-methyl-1-c-pentenyl group, a 2-methyl-2-c-pentenyl group, a 2-methyl-3-c-pentenyl group, a 2-methyl-4-c-pentenyl group, a 2-methyl-5-c-pentenyl group, a 2-methylene-c-pentyl group, a 3-methyl-1-c-pentenyl group, a 3-methyl-2-c-pentenyl group, a 3-methyl-3-c-pentenyl group, a 3-methyl-4-c-pentenyl group, a 3-methyl-5-c-pentenyl group, a 3-methylene-c-pentyl group, a 1-c-hexenyl group, a 2-c-hexenyl group, a 3-c-hexenyl and the like may be mentioned.

A $C_{2-6}$ alyklenylene group is a bivalent group obtained by removing a hydrogen atom from the above-mentioned $C_{2-6}$ alkenyl group and may be a linear, branched or cyclic alkenylene group. For example, an ethenylene group, a propenylene group, an isopropenylene group, a c-propenylene group, an ethylpropenylene group, a butenylene group, an isobutenylene group, a c-butenylene group, an ethylbutenylene group, a pentenylene group, a c-pentenylene group, a hexenylene group and a c-hexenylene group may be mentioned.

A $C_{3-10}$ cycloalkenyl group means a group obtained by converting arbitrary one, two or three bonds in the above-mentioned $C_{3-10}$ cycloalkyl group to double bonds and may have a fused polycyclic structure, a bridged cyclic structure or a spirocyclic structure. As specific examples, a c-propenyl group, a c-butenyl group, a c-pentenyl group, a c-hexenyl group, a c-hexa-1,3-dienyl group, a c-heptenyl group, a c-hepta-1,4-dienyl group, a c-octenyl group, a c-octa-1,3,5-trienyl group, a c-nonenyl group, a c-decenyl group, the structures shown below and the like may be mentioned.

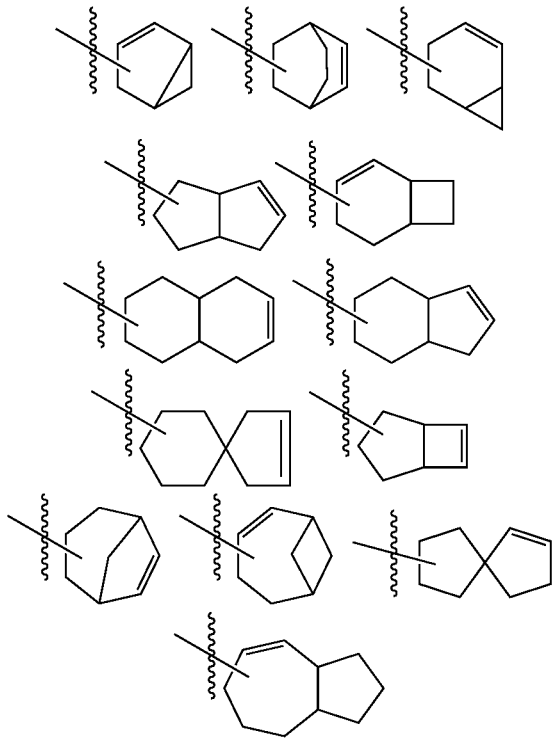

A $C_{2-6}$ alkynyl group is an alkynyl group having two to six carbon atoms and may be linear, branched or a $C_6$ cycloalkynyl group. As specific examples, an ethynyl group, a 1-propynyl group, a 2-propynyl group, a 1-butynyl group, a 2-butynyl group, a 3-butynyl group, a 1-methyl-2-propynyl group, a 1-pentynyl group, a 2-pentynyl group, a 3-pentynyl group, a 4-pentynyl group, a 1-methyl-2-butynyl group, a 1-methyl-3-butynyl group, a 2-methyl-3-butynyl group, a 3-methyl-1-butynyl group, a 1,1-dimethyl-2-propynyl group, a 1-hexynyl group, a 2-hexynyl group, a 3-hexynyl group, a 4-hexynyl group, a 5-hexynyl group, a 1-methyl-2-pentynyl group, a 1-methyl-3-pentynyl group, a 1-methyl-4-pentynyl group, a 2-methyl-3-pentynyl group, a 2-methyl-4-pentynyl group, a 3-methyl-1-pentynyl group, a 3-methyl-4-pentynyl group, a 4-methyl-1-pentynyl group, a 4-methyl-2-pentynyl group, a 1,1-dimethyl-2-butynyl group, a 1,1-dimethyl-3-butynyl group, a 1,2-dimethyl-3-butynyl group, a 2,2-dimethyl-3-butynyl group, a 3,3-dimethyl-1-butynyl group, a 1-ethyl-2-butynyl group, a 1-ethyl-3-butynyl group, a 1-n-propyl-2-propynyl group, a 2-ethyl-3-butynyl group, a 1-methyl-1-ethyl-2-propynyl group, a 1-c-propyl-2-propynyl group, a 1-i-propyl-2-propynyl group and the like may be mentioned.

A $C_{2-6}$ alkynylene group is a bivalent group obtained by removing a hydrogen atom from the above-mentioned $C_{2-6}$ alkynyl group and may be linear, branched or cyclic. For example, an ethynylene group, a propynylene group, an isopropynylene group, a c-propynylene group, an ethylpropynylene group, a butynylene group, an isobutynylene group, a c-butynylene group, an ethylbutynylene group, a pentynylene group, a c-pentynylene group, a hexynylene group and a c-hexynylene group may be mentioned.

A $C_{1-6}$ alkoxy group is an alkoxy group having one to six carbon atoms and may be linear, branched or a $C_{3-6}$ cycloalkoxy group. As specific examples, a methoxy group, an ethoxy group, a n-propoxy group, an i-propoxy group, a c-propoxy group, a n-butoxy group, an i-butoxy group, a s-butoxy group, a t-butoxy group, a c-butoxy group, a 1-methyl-c-propoxy group, a 2-methyl-c-propoxy group, a n-pentyloxy group, a 1-methyl-n-butoxy group, a 2-methyl-n-butoxy group, a 3-methyl-n-butoxy group, a 1,1-dimethyl-n-propoxy group, a 1,2-dimethyl-n-propoxy group, a 2,2-dimethyl-n-propoxy group, a 1-ethyl-n-propoxy group, a c-pentyloxy group, a 1-methyl-c-butoxy group, a 2-methyl-c-butoxy group, a 3-methyl-c-butoxy group, a 1,2-dimethyl-c-propoxy group, a 2,3-dimethyl-c-propoxy group, a 1-ethyl-c-propoxy group, a 2-ethyl-c-propoxy group, a n-hexyloxy group, a 1-methyl-n-pentyloxy group, a 2-methyl-n-pentyloxy group, a 3-methyl-n-pentyloxy group, a 4-methyl-n-pentyloxy group, a 1,1-dimethyl-n-butoxy group, a 1,2-dimethyl-n-butoxy group, a 1,3-dimethyl-n-butoxy group, a 2,2-dimethyl-n-butoxy group, a 2,3-dimethyl-n-butoxy group, a 3,3-dimethyl-n-butoxy group, a 1-ethyl-n-butoxy group, a 2-ethyl-n-butoxy group, a 1,1,2-trimethyl-n-propoxy group, a 1,2,2-trimethyl-n-propoxy group, a 1-ethyl-1-methyl-n-propoxy group, a 1-ethyl-2-methyl-n-propoxy group, a c-hexyloxy group, a 1-methyl-c-pentyloxy group, a 2-methyl-c-pentyloxy group, a 3-methyl-c-pentyloxy group, a 1-ethyl-c-butoxy group, a 2-ethyl-c-butoxy group, a 3-ethyl-c-butoxy group, a 1,2-dimethyl-c-butoxy group, a 1,3-dimethyl-c-butoxy group, a 2,2-dimethyl-c-butoxy group, a 2,3-dimethyl-c-butoxy group, a 2,4-dimethyl-c-butoxy group, a 3,3-dimethyl-c-butoxy group, a 1-n-propyl-c-propoxy group, a 2-n-propyl-c-propoxy group, a 1-i-propyl-c-propoxy group, a 2-i-propyl-c-propoxy group, a 1,2,2-trimethyl-c-propoxy group, a 1,2,3-trimethyl-c-propoxy group, a 2,2,3-trimethyl-c-propoxy group, a 1-ethyl-2-methyl-c-propoxy group, a 2-ethyl-1-methyl-c-propoxy group, a 2-ethyl-2-methyl-c-propoxy group, a 2-ethyl-3-methyl-c-propoxy group and the like may be mentioned.

A $C_{1-3}$ alkoxy group is an alkoxy group having one to three carbon atoms and may be linear, branched or a $C_3$ cycloalkoxy group. As specific examples, a methoxy group, an ethoxy group, a n-propoxy group, an i-propoxy group, a c-propoxy group and the like may be mentioned.

A $C_{1-3}$ haloalkoxy group is a $C_{1-3}$ alkoxy group such as those mentioned above in which the alkoxy group is substituted with one or more halogen atoms. As specific examples, a chloromethoxy group, a trifluoromethoxy group, a difluoromethoxy group, a monofluoromethoxy group and the like may be mentioned.

A $C_{2-14}$ aryl group means a $C_{6-14}$ aryl group containing no hetero atoms as ring constituting atoms or a $C_{2-9}$ aromatic heterocyclic group.

A $C_{6-14}$ aryl group containing no hetero atoms is an aryl group containing six to fourteen carbon atoms, and as specific examples, a phenyl group, an α-naphthyl group, a β-naphthyl group, an o-biphenylyl group, a m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group and the like may be mentioned.

A $C_{2-9}$ aromatic heterocyclic group means a 5 to 7-membered $C_{2-6}$ heteromonocyclic group or a 8 to 10-membered $C_{6-9}$ fused heterobicyclic group containing from 1 to 3 oxygen atoms, nitrogen atoms or sulfur atoms singly or in combination, and, if contains one or more nitrogen atoms, may be in the form of an N-oxide.

As specific examples of 5 to 7-membered $C_{2-6}$ heteromonocyclic groups, a 2-thienyl group, a 3-thienyl group, a 2-furyl group, a 3-furyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 5-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group, a 3-1,2,5-thiadiazolyl group, 3-4H-1,2,4-triazolyl group, 3-1H-1,2,4-triazolyl group, 5-1H-1,2,4-triazolyl group, 4-2H-1,2,3-triazolyl group, 5-2H-1,2,3-triazolyl group, 4-1H-1,2,3-triazolyl group and 5-1H-1,2,3-triazolyl group and the like may be mentioned.

A 8 to 10-membered $C_{5-9}$ fused heterobicyclic group may be a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 2-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, a 1-indazolyl group, a 2-indazolyl group, a 3-indazolyl group, a 4-indazolyl group, a 5-indazolyl group, a 6-indazolyl group, a 7-indazolyl group, a 2-(7-aza)indazolyl group, a 3-(7-aza)indazolyl group, a 4-(7-aza)indazolyl group, a 5-(7-aza)indazolyl group, a 6-(7-aza)indazolyl group, a 2-(4-aza) indazolyl group, a 3-(4-aza)indazolyl group, a 5-(4-aza)indazolyl group, a 6-(4-aza)indazolyl group, a 7-(4-aza)indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 1-2,7-naphthyridinyl group, a 3-2,7-naphthyridinyl group, a 4-2,7-naphthyridinyl group, a 1-2,6-naphthyridinyl group, a 3-2,6-naphthyridinyl group, a 4-2,6-naphthyridinyl group, a 2-1,8-naphthyridinyl group, a 3-1,8-naphthyridinyl group, a 4-1,8-naphthyridinyl group, a 2-1,7-naphthyridinyl group, a 3-1,7-naphthyridinyl group, a 4-1,7-naphthyridinyl group, a 5-1,7-naphthyridinyl group, a 6-1,7-naphthyridinyl group, a 8-1,7-naphthyridinyl group, 2-1,6-naphthyridinyl group, a 3-1,6-naphthyridinyl group, a 4-1,6-naphthyridinyl group, a 5-1,6-naphthyridinyl group, a 7-1,6-naphthyridinyl group, a 8-1,6-naphthyridinyl group, a 2-1,5-naphthyridinyl group, a 3-1,5-naphthyridinyl group, a 4-1,5-naphthyridinyl group, a 6-1,5-naphthyridinyl group, a 7-1,5-naphthyridinyl group, a 8-1,5-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pteridinyl group, a 4-pteridinyl group, a 6-pteridinyl group, a 7-pteridinyl group or the like.

A $C_{4-6}$ aryl group means an aromatic group constituted by four to six carbon atoms and zero to one hetero atom selected from the group consisting of a nitrogen atom, an oxygen atom and a sulfur atom (provided that when there are no hetero atoms, the number of carbon atoms is six). As specific examples, a phenyl group, a pyridyl group, a thienyl group, a pyrrolyl group, a furyl group or the like may be mentioned.

A $C_{2-9}$ heterocyclyl group is a heteromonocyclic or fused heterobicyclic group consisting of at least one atom arbitrarily selected from nitrogen atoms, oxygen atoms and sulfur atoms and two to nine carbon atoms, and carbon atoms constituting the ring may be carbonyl or thiocarbonyl. As specific examples,

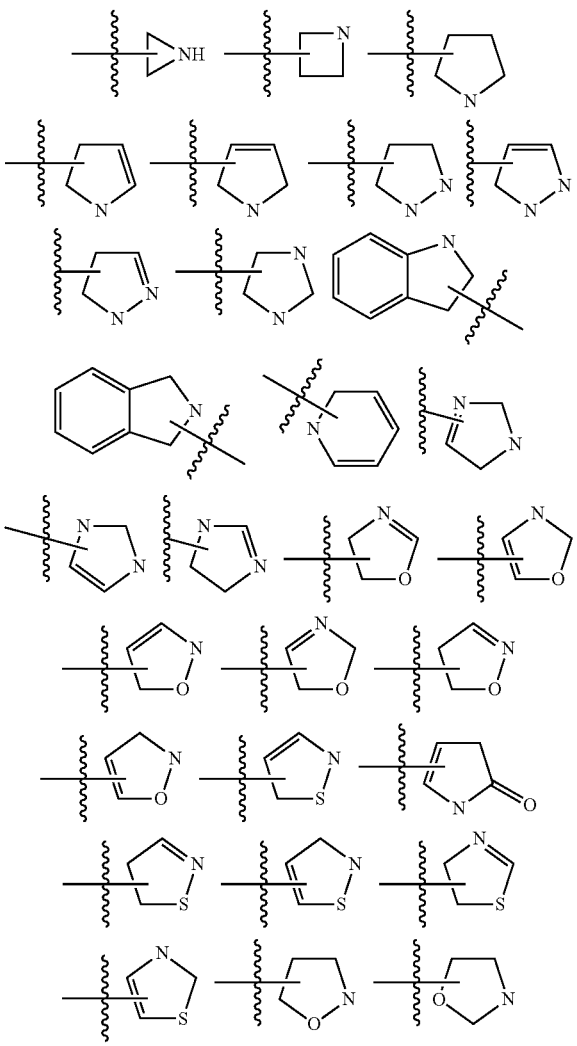

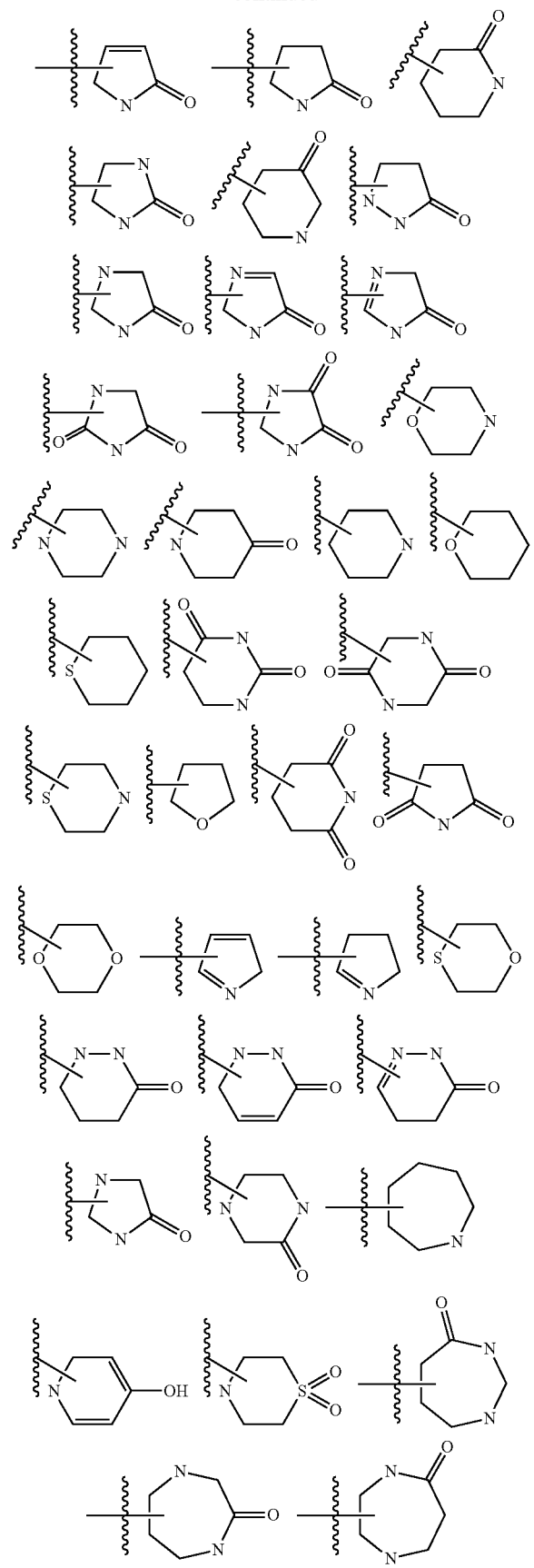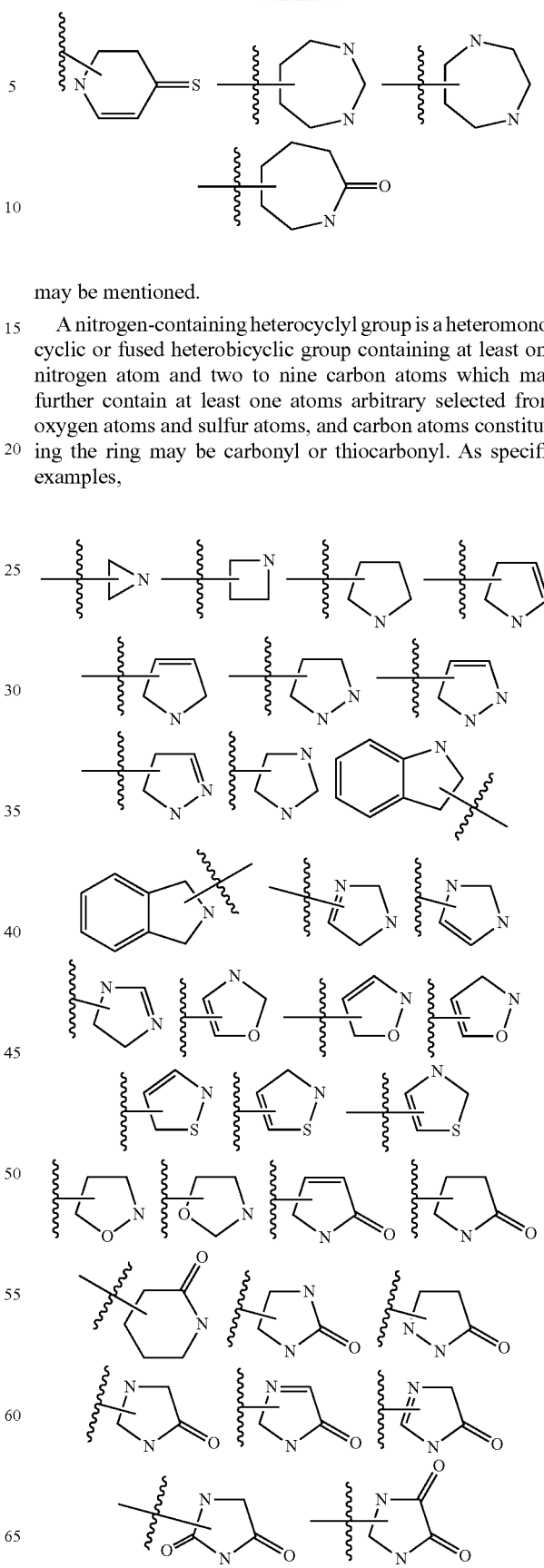

may be mentioned.

A nitrogen-containing heterocyclyl group is a heteromonocyclic or fused heterobicyclic group containing at least one nitrogen atom and two to nine carbon atoms which may further contain at least one atoms arbitrary selected from oxygen atoms and sulfur atoms, and carbon atoms constituting the ring may be carbonyl or thiocarbonyl. As specific examples,

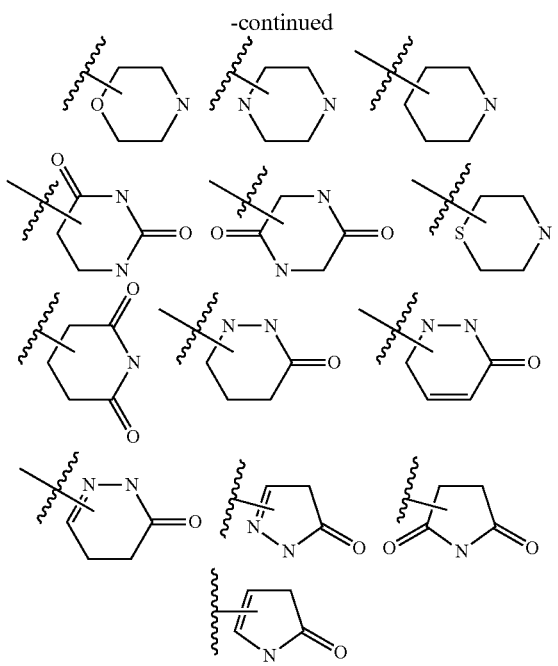

may be mentioned.

A $C_{4-5}$ nitrogen-containing heterocyclyl group means a group having a ring structure consisting of one to two nitrogen or oxygen atoms and four to five carbon atoms and having no unsaturated bonds. As specific examples, a piperazinyl group, a piperidinyl group, a pyrrolidinyl group, a morpholinyl group and the like may be mentioned. Preferably, it is a group having a ring structure consisting of one to two nitrogen atoms and four to five carbon atoms and having no saturated bonds.

A $C_{3-5}$ oxygen-containing heterocyclyl group means a group having a ring structure consisting of one to two oxygen atoms and three to five carbon atoms and having no unsaturated bonds. As specific examples, a tetrahydrofuranyl group, a tetrahydro-2H-pyranyl group, a 1,3-dioxolanyl group, a 1,4-dioxanyl group and the like may be mentioned.

A mono-$C_{1-6}$ alkylamino group is an amino group containing one $C_{1-6}$ alkyl group and may be linear, branched or a $C_{3-6}$ cycloalkylamino group, and as specific examples, a methylamino group, an ethylamino group, a n-propylamino group, an i-propylamino group, a c-propylamino group, a n-butylamino group, an i-butylamino group, a s-butylamino group, a t-butylamino group, a c-butylamino group, a 1-methyl-c-propylamino group, a 2-methyl-c-propylamino group, a n-pentylamino group, a 1-methyl-n-butylamino group, a 2-methyl-n-butylamino group, a 3-methyl-n-butylamino group, a 1,1-dimethyl-n-propylamino group, a 1,2-dimethyl-n-propylamino group, a 2,2-dimethyl-n-propylamino group, a 1-ethyl-n-propylamino group, a c-pentylamino group, a 1-methyl-c-butylamino group, a 2-methyl-c-butylamino group, a 3-methyl-c-butylamino group, a 1,2-dimethyl-c-propylamino group, a 2,3-dimethyl-c-propylamino group, a 1-ethyl-c-propylamino group, a 2-ethyl-c-propylamino group, a n-hexylamino group, a 1-methyl-n-pentylamino group, a 2-methyl-n-pentylamino group, a 3-methyl-n-pentylamino group, a 4-methyl-n-pentylamino group, a 1,1-dimethyl-n-butylamino group, a 1,2-dimethyl-n-butylamino group, a 1,3-dimethyl-n-butylamino group, a 2,2-dimethyl-n-butylamino group, a 2,3-dimethyl-n-butylamino group, a 3,3-dimethyl-n-butylamino group, a 1-ethyl-n-butylamino group, a 2-ethyl-n-butylamino group, a 1,1,2-trimethyl-n-propylamino group, a 1,2,2-trimethyl-n-propylamino group, a 1-ethyl-1-methyl-n-propylamino group, a 1-ethyl-2-methyl-n-propylamino group, a c-hexylamino group, a 1-methyl-c-pentylamino group, a 2-methyl-c-pentylamino group, a 3-methyl-c-pentylamino group, a 1-ethyl-c-butylamino group, a 2-ethyl-c-butylamino group, a 3-ethyl-c-butylamino group, a 1,2-dimethyl-c-butylamino group, a 1,3-dimethyl-c-butylamino group, a 2,2-dimethyl-c-butylamino group, a 2,3-dimethyl-c-butylamino group, a 2,4-dimethyl-c-butylamino group, a 3,3-dimethyl-c-butylamino group, a 1-n-propyl-c-propylamino group, a 2-n-propyl-c-propylamino group, a 1-i-propyl-c-propylamino group, a 2-i-propyl-c-propylamino group, a 1,2,2-trimethyl-c-propylamino group, a 1,2,3-trimethyl-c-propylamino group, a 2,2,3-trimethyl-c-propylamino group, a 1-ethyl-2-methyl-c-propylamino group, a 2-ethyl-1-methyl-c-propylamino group, a 2-ethyl-2-methyl-c-propylamino group, a 2-ethyl-3-methyl-c-propylamino group or the like may be mentioned.

A di-$C_{1-6}$ alkylamino group is an amino group having two $C_{1-6}$ alkyl groups and may be symmetric or asymmetric. A symmetric $C_{1-6}$ dialkylamino group may be linear, branched or a $C_{3-6}$ cycloalkylamino group, and as specific examples, a dimethylamino group, a diethylamino group, a di-n-propylamino group, a di-i-propylamino group, a di-c-propylamino group, a di-n-butylamino group, a di-i-butylamino group, a di-s-butylamino group, a di-t-butylamino group, a di-c-butylamino group, a di-(1-methyl-c-propyl)amino group, a di-(2-methyl-c-propyl)amino group, a di-n-pentylamino group, a di-(1-methyl-n-butyl)amino group, a di-(2-methyl-n-butyl)amino group, a di-(3-methyl-n-butyl)amino group, a di-(1,1-dimethyl-n-propyl)amino group, a di-(1,2-dimethyl-n-propyl)amino group, a di-(2,2-dimethyl-n-propyl)amino group, a di-(1-ethyl-n-propyl)amino group, a di-c-pentylamino group, a di-(1-methyl-c-butyl)amino group, a di-(2-methyl-c-butyl)amino group, a di-(3-methyl-c-butyl)amino group, a di-(1,2-dimethyl-c-propyl)amino group, a di-(2,3-dimethyl-c-propyl)amino group, a di-(1-ethyl-c-propyl)amino group, a di-(2-ethyl-c-propyl)amino group, a di-n-hexylamino group, a di-(1-methyl-n-pentyl)amino group, a di-(2-methyl-n-pentyl)amino group, a di-(3-methyl-n-pentyl)amino group, a di-(4-methyl-n-pentyl)amino group, a di-(1,1-dimethyl-n-butyl)amino group, a di-(1,2-dimethyl-n-butyl)amino group, a di-(1,3-dimethyl-n-butyl)amino group, a di-(2,2-dimethyl-n-butyl)amino group, a di-(2,3-dimethyl-n-butyl)amino group, a di-(3,3-dimethyl-n-butyl)amino group, a di-(1-ethyl-n-butyl)amino group, a di-(2-ethyl-n-butyl)amino group, a di-(1,1,2-trimethyl-n-propyl)amino group, a di-(1,2,2-trimethyl-n-propyl)amino group, a di-(1-ethyl-1-methyl-n-propyl)amino group, a di-(1-ethyl-2-methyl-n-propyl)amino group, a di-c-hexylamino group, a di-(1-methyl-c-pentyl)amino group, a di-(2-methyl-c-pentyl)amino group, a di-(3-methyl-c-pentyl)amino group, a di-(1-ethyl-c-butyl)amino group, a di-(2-ethyl-c-butyl)amino group, a di-(3-ethyl-c-butyl)amino group, a di-(1,2-dimethyl-c-butyl)amino group, a di-(1,3-dimethyl-c-butyl)amino group, a di-(2,2-dimethyl-c-butyl)amino group, a di-(2,3-dimethyl-c-butyl)amino group, a di-(2,4-dimethyl-c-butyl)amino group, a di-(3,3-dimethyl-c-butyl)amino group, a di-(1-n-propyl-c-propyl)amino group, a di-(2-n-propyl-c-propyl)amino group, a di-(1-i-propyl-c-propyl)amino group, a di-(2-i-propyl-c-propyl)amino group, a di-(1,2,2-trimethyl-c-propyl)amino group, a di-(1,2,3-trimethyl-c-propyl)amino group, a di-(2,2,3-trimethyl-c-propyl)amino group, a di-(1-ethyl-2-methyl-c-propyl)amino group, a di-(2-ethyl-1-methyl-c-propyl)amino group, a di-(2-ethyl-2-methyl-c-propyl)amino group, a di-(2-ethyl-3-methyl-c-propyl)amino group and the like may be mentioned.

An asymmetric di-$C_{1-6}$ alkylamino group may be linear, branched or a $C_{3-6}$ cycloalkylamino group, and as specific examples, a (methyl, ethyl)amino group, a (methyl, n-propyl)amino group, a (methyl, i-propyl)amino group, a (methyl, c-propyl)amino group, a (methyl, n-butyl)amino group, a (methyl, i-butyl)amino group, a (methyl, s-butyl)amino group, a (methyl, t-butyl)amino group, a (methyl, n-pentyl)amino group, a (methyl, c-pentyl)amino group, a (methyl, n-hexyl)amino group, a (methyl, c-hexyl)amino group, a (ethyl, n-propyl)amino group, a (ethyl, i-propyl)amino group, a (ethyl, c-propyl)amino group, a (ethyl, n-butyl)amino group, a (ethyl, i-butyl)amino group, a (ethyl, s-butyl)amino group, a (ethyl, t-butyl)amino group, a (ethyl, n-pentyl)amino group, a (ethyl, c-pentyl)amino group, a (ethyl, n-hexyl)amino group, a (ethyl, c-hexyl)amino group, a (n-propyl, i-propyl)amino group, a (n-propyl, c-propyl)amino group, a (n-propyl, n-butyl)amino group, a (n-propyl, i-butyl)amino group, a (n-propyl, s-butyl)amino group, a (n-propyl, t-butyl)amino group, a (n-propyl, n-pentyl)amino group, a (n-propyl, c-pentyl)amino group, a (n-propyl, n-hexyl)amino group, a (n-propyl, c-hexyl)amino group, an (i-propyl, c-propyl)amino group, an (i-propyl, n-butyl)amino group, an (i-propyl, i-butyl)amino group, an (i-propyl, s-butyl)amino group, an (i-propyl, t-butyl)amino group, an (i-propyl, n-pentyl)amino group, an (i-propyl, c-pentyl)amino group, an (i-propyl, n-hexyl)amino group, an (i-propyl, c-hexyl)amino group, a (c-propyl, n-butyl)amino group, a (c-propyl, i-butyl)amino group, a (c-propyl, s-butyl)amino group, a (c-propyl, t-butyl)amino group, a (c-propyl, n-pentyl)amino group, a (c-propyl, c-pentyl)amino group, a (c-propyl, n-hexyl)amino group, a (c-propyl, c-hexyl)amino group, a (n-butyl, i-butyl)amino group, a (n-butyl, s-butyl)amino group, a (n-butyl, t-butyl)amino group, a (n-butyl, n-pentyl)amino group, a (n-butyl, c-pentyl)amino group, a (n-butyl, n-hexyl)amino group, a (n-butyl, c-hexyl)amino group, an (i-butyl, s-butyl)amino group, an (i-butyl, t-butyl)amino group, an (i-butyl, n-pentyl)amino group, an (i-butyl, c-pentyl)amino group, an (i-butyl, n-hexyl)amino group, an (i-butyl, c-hexyl)amino group, a (s-butyl, t-butyl)amino group, a (s-butyl, n-pentyl)amino group, a (s-butyl, c-pentyl)amino group, a (s-butyl, n-hexyl)amino group, a (s-butyl, c-hexyl)amino group, a (t-butyl, n-pentyl)amino group, a (t-butyl, c-pentyl)amino group, a (t-butyl, n-hexyl)amino group, a (t-butyl, c-hexyl)amino group, a (n-pentyl, c-pentyl)amino group, a (n-pentyl, n-hexyl)amino group, a (n-pentyl, c-hexyl)amino group, a (c-pentyl, n-hexyl)amino group, a (c-pentyl, c-hexyl)amino group, a (n-hexyl, c-hexyl)amino group and the like may be mentioned.

A $C_{1-6}$ alkylthio group is a thio group having a $C_{1-6}$ alkyl group and may be linear, branched or a $C_{3-6}$ cycloalkylthio group. As specific examples, a methylthio group, an ethylthio group, a n-propylthio group, an i-propylthio group, a c-propylthio group, a n-butylthio group, an i-butylthio group, a s-butylthio group, a t-butylthio group, a c-butylthio group, a 1-methyl-c-propylthio group, a 2-methyl-c-propylthio group, a n-pentylthio group, a 1-methyl-n-butylthio group, a 2-methyl-n-butylthio group, a 3-methyl-n-butylthio group, a 1,1-dimethyl-n-propylthio group, a 1,2-dimethyl-n-propylthio group, a 2,2-dimethyl-n-propylthio group, a 1-ethyl-n-propylthio group, a c-pentylthio group, a 1-methyl-c-butylthio group, a 2-methyl-c-butylthio group, a 3-methyl-c-butylthio group, a 1,2-dimethyl-c-propylthio group, a 2,3-dimethyl-c-propylthio group, a 1-ethyl-c-propylthio group, a 2-ethyl-c-propylthio group, a n-hexylthio group, a 1-methyl-n-pentylthio group, a 2-methyl-n-pentylthio group, a 3-methyl-n-pentylthio group, a 4-methyl-n-pentylthio group, a 1,1-dimethyl-n-butylthio group, a 1,2-dimethyl-n-butylthio group, a 1,3-dimethyl-n-butylthio group, a 2,2-dimethyl-n-butylthio group, a 2,3-dimethyl-n-butylthio group, a 3,3-dimethyl-n-butylthio group, a 1-ethyl-n-butylthio group, a 2-ethyl-n-butylthio group, a 1,1,2-trimethyl-n-propylthio group, a 1,2,2-trimethyl-n-propylthio group, a 1-ethyl-1-methyl-n-propylthio group, a 1-ethyl-2-methyl-n-propylthio group, a c-hexylthio group, a 1-methyl-c-pentylthio group, a 2-methyl-c-pentylthio group, a 3-methyl-c-pentylthio group, a 1-ethyl-c-butylthio group, a 2-ethyl-c-butylthio group, a 3-ethyl-c-butylthio group, a 1,2-dimethyl-c-butylthio group, a 1,3-dimethyl-c-butylthio group, a 2,2-dimethyl-c-butylthio group, a 2,3-dimethyl-c-butylthio group, a 2,4-dimethyl-c-butylthio group, a 3,3-dimethyl-c-butylthio group, a 1-n-propyl-c-propylthio group, a 2-n-propyl-c-propylthio group, a 1-i-propyl-c-propylthio group, a 2-i-propyl-c-propylthio group, a 1,2,2-trimethyl-c-propylthio group, a 1,2,3-trimethyl-c-propylthio group, a 2,2,3-trimethyl-c-propylthio group, a 1-ethyl-2-methyl-c-propylthio group, a 2-ethyl-1-methyl-c-propylthio group, a 2-ethyl-2-methyl-c-propylthio group, a 2-ethyl-3-methyl-c-propylthio group and the like may be mentioned.

A $C_{1-6}$ alkylsulfonyl group is a sulfonyl group having a $C_{1-6}$ alkyl group and may be linear, branched or a $C_{3-6}$ cycloalkylsulfonyl group. As specific examples, a methylsulfonyl group, an ethylsulfonyl group, a n-propylsulfonyl group, an i-propylsulfonyl group, a c-propylsulfonyl group, a n-butylsulfonyl group, an i-butylsulfonyl group, a s-butylsulfonyl group, a t-butylsulfonyl group, a c-butylsulfonyl group, a 1-methyl-c-propylsulfonyl group, a 2-methyl-c-propylsulfonyl group, a n-pentylsulfonyl group, a 1-methyl-n-butylsulfonyl group, a 2-methyl-n-butylsulfonyl group, a 3-methyl-n-butylsulfonyl group, a 1,1-dimethyl-n-propylsulfonyl group, a 1,2-dimethyl-n-propylsulfonyl group, a 2,2-dimethyl-n-propylsulfonyl group, a 1-ethyl-n-propylsulfonyl group, a c-pentylsulfonyl group, a 1-methyl-c-butylsulfonyl group, a 2-methyl-c-butylsulfonyl group, a 3-methyl-c-butylsulfonyl group, a 1,2-dimethyl-c-propylsulfonyl group, a 2,3-dimethyl-c-propylsulfonyl group, a 1-ethyl-c-propylsulfonyl group, a 2-ethyl-c-propylsulfonyl group, a n-hexylsulfonyl group, a 1-methyl-n-pentylsulfonyl group, a 2-methyl-n-pentylsulfonyl group, a 3-methyl-n-pentylsulfonyl group, a 4-methyl-n-pentylsulfonyl group, a 1,1-dimethyl-n-butylsulfonyl group, a 1,2-dimethyl-n-butylsulfonyl group, a 1,3-dimethyl-n-butylsulfonyl group, a 2,2-dimethyl-n-butylsulfonyl group, a 2,3-dimethyl-n-butylsulfonyl group, a 3,3-dimethyl-n-butylsulfonyl group, a 1-ethyl-n-butylsulfonyl group, a 2-ethyl-n-butylsulfonyl group, a 1,1,2-trimethyl-n-propylsulfonyl group, a 1,2,2-trimethyl-n-propylsulfonyl group, a 1-ethyl-1-methyl-n-propylsulfonyl group, a 1-ethyl-2-methyl-n-propylsulfonyl group, a c-hexylsulfonyl group, a 1-methyl-c-pentylsulfonyl group, a 2-methyl-c-pentylsulfonyl group, a 3-methyl-c-pentylsulfonyl group, a 1-ethyl-c-butylsulfonyl group, a 2-ethyl-c-butylsulfonyl group, a 3-ethyl-c-butylsulfonyl group, a 1,2-dimethyl-c-butylsulfonyl group, a 1,3-dimethyl-c-butylsulfonyl group, a 2,2-dimethyl-c-butylsulfonyl group, a 2,3-dimethyl-c-butylsulfonyl group, a 2,4-dimethyl-c-butylsulfonyl group, a 3,3-dimethyl-c-butylsulfonyl group, a 1-n-propyl-c-propylsulfonyl group, a 2-n-propyl-c-propylsulfonyl group, a 1-i-propyl-c-propylsulfonyl group, a 2-i-propyl-c-propylsulfonyl group, a 1,2,2-trimethyl-c-propylsulfonyl group, a 1,2,3-trimethyl-c-propylsulfonyl group, a 2,2,3-trimethyl-c-propylsulfonyl group, a 1-ethyl-2-methyl-c-propylsulfonyl group, a 2-ethyl-1-methyl-c-propylsulfonyl group, a 2-ethyl-2-methyl-c-propylsulfonyl group, a 2-ethyl-3-methyl-c-propylsulfonyl group and the like may be mentioned.

A mono-$C_{1-6}$ alkylaminocarbonyl group is an aminocarbonyl group having a $C_{1-6}$ alkyl group and may be linear, branched or a $C_{3-6}$ cycloalkylaminocarbonyl group. As specific example, a methylaminocarbonyl group, an ethylaminocarbonyl group, a n-propylaminocarbonyl group, an i-propylaminocarbonyl group, a c-propylaminocarbonyl group, a n-butylaminocarbonyl group, an i-butylaminocarbonyl group, a s-butylaminocarbonyl group, a t-butylaminocarbonyl group, a c-butylaminocarbonyl group, a 1-methyl-c-propylaminocarbonyl group, a 2-methyl-c-propylaminocarbonyl group, a n-pentylaminocarbonyl group, a 1-methyl-n-butylaminocarbonyl group, a 2-methyl-n-butylaminocarbonyl group, a 3-methyl-n-butylaminocarbonyl group, a 1,1-dimethyl-n-propylaminocarbonyl group, a 1,2-dimethyl-n-propylaminocarbonyl group, a 2,2-dimethyl-n-propylaminocarbonyl group, a 1-ethyl-n-propylaminocarbonyl group, a c-pentylaminocarbonyl group, a 1-methyl-c-butylaminocarbonyl group, a 2-methyl-c-butylaminocarbonyl group, a 3-methyl-c-butylaminocarbonyl group, a 1,2-dimethyl-c-propylaminocarbonyl group, a 2,3-dimethyl-c-propylaminocarbonyl group, a 1-ethyl-c-propylaminocarbonyl group, a 2-ethyl-c-propylaminocarbonyl group, a n-hexylaminocarbonyl group, a 1-methyl-n-pentylaminocarbonyl group, a 2-methyl-n-pentylaminocarbonyl group, a 3-methyl-n-pentylaminocarbonyl group, a 4-methyl-n-pentylaminocarbonyl group, a 1,1-dimethyl-n-butylaminocarbonyl group, a 1,2-dimethyl-n-butylaminocarbonyl group, a 1,3-dimethyl-n-butylaminocarbonyl group, a 2,2-dimethyl-n-butylaminocarbonyl group, a 2,3-dimethyl-n-butylaminocarbonyl group, a 3,3-dimethyl-n-butylaminocarbonyl group, a 1-ethyl-n-butylaminocarbonyl group, a 2-ethyl-n-butylaminocarbonyl group, a 1,1,2-trimethyl-n-propylaminocarbonyl group, a 1,2,2-trimethyl-n-propylaminocarbonyl group, a 1-ethyl-1-methyl-n-propylaminocarbonyl group, a 1-ethyl-2-methyl-n-propylaminocarbonyl group, a c-hexylaminocarbonyl group, a 1-methyl-c-pentylaminocarbonyl group, a 2-methyl-c-pentylaminocarbonyl group, a 3-methyl-c-pentylaminocarbonyl group, a 1-ethyl-c-butylaminocarbonyl group, a 2-ethyl-c-butylaminocarbonyl group, a 3-ethyl-c-butylaminocarbonyl group, a 1,2-dimethyl-c-butylaminocarbonyl group, a 1,3-dimethyl-c-butylaminocarbonyl group, a 2,2-dimethyl-c-butylaminocarbonyl group, a 2,3-dimethyl-c-butylaminocarbonyl group, a 2,4-dimethyl-c-butylaminocarbonyl group, a 3,3-dimethyl-c-butylaminocarbonyl group, a 1-n-propyl-c-propylaminocarbonyl group, a 2-n-propyl-c-propylaminocarbonyl group, a 1-i-propyl-c-propylaminocarbonyl group, a 2-i-propyl-c-propylaminocarbonyl group, a 1,2,2-trimethyl-c-propylaminocarbonyl group, a 1,2,3-trimethyl-c-propylaminocarbonyl group, a 2,2,3-trimethyl-c-propylaminocarbonyl group, a 1-ethyl-2-methyl-c-propylaminocarbonyl group, a 2-ethyl-1-methyl-c-propylaminocarbonyl group, a 2-ethyl-2-methyl-c-propylaminocarbonyl group, a 2-ethyl-3-methyl-c-propylaminocarbonyl group or the like may be mentioned.

A di-$C_{1-6}$ alkylaminocarbonyl group is an aminocarbonyl group having two $C_{1-6}$ alkyl groups and may be symmetric or asymmetric. A symmetric $C_{1-6}$ dialkylaminocarbonyl group may be linear, branched or a $C_{3-6}$ cycloalkylaminocarbonyl group, and as specific examples, a dimethylaminocarbonyl group, a diethylaminocarbonyl group, a di-n-propylaminocarbonyl group, a di-i-propylaminocarbonyl group, a di-c-propylaminocarbonyl group, a di-n-butylaminocarbonyl group, a di-1-butylaminocarbonyl group, a di-s-butylaminocarbonyl group, a di-t-butylaminocarbonyl group, a di-c-butylaminocarbonyl group, a di-(1-methyl-c-propyl)aminocarbonyl group, a di-(2-methyl-c-propyl)aminocarbonyl group, a di-n-pentylaminocarbonyl group, a di-(1-methyl-n-butyl)aminocarbonyl group, a di-(2-methyl-n-butyl)aminocarbonyl group, a di-(3-methyl-n-butyl)aminocarbonyl group, a di-(1,1-dimethyl-n-propyl)aminocarbonyl group, a di-(1,2-dimethyl-n-propyl)aminocarbonyl group, a di-(2,2-dimethyl-n-propyl)aminocarbonyl group, a di-(1-ethyl-n-propyl)aminocarbonyl group, a di-c-pentylaminocarbonyl group, a di-(1-methyl-c-butyl)aminocarbonyl group, a di-(2-methyl-c-butyl)aminocarbonyl group, a di-(3-methyl-c-butyl)aminocarbonyl group, a di-(1,2-dimethyl-c-propyl)aminocarbonyl group, a di-(2,3-dimethyl-c-propyl)aminocarbonyl group, a di-(1-ethyl-c-propyl)aminocarbonyl group, a di-(2-ethyl-c-propyl)aminocarbonyl group, a di-n-hexylaminocarbonyl group, a di-(1-methyl-n-pentyl)aminocarbonyl group, a di-(2-methyl-n-pentyl)aminocarbonyl group, a di-(3-methyl-n-pentyl)aminocarbonyl group, a di-(4-methyl-n-pentyl)aminocarbonyl group, a di-(1,1-dimethyl-n-butyl)aminocarbonyl group, a di-(1,2-dimethyl-n-butyl)aminocarbonyl group, a di-(1,3-dimethyl-n-butyl)aminocarbonyl group, a di-(2,2-dimethyl-n-butyl)aminocarbonyl group, a di-(2,3-dimethyl-n-butyl)aminocarbonyl group, a di-(3,3-dimethyl-n-butyl)aminocarbonyl group, a di-(1-ethyl-n-butyl)aminocarbonyl group, a di-(2-ethyl-n-butyl)aminocarbonyl group, a di-(1,1,2-trimethyl-n-propyl)aminocarbonyl group, a di-(1,2,2-trimethyl-n-propyl)aminocarbonyl group, a di-(1-ethyl-1-methyl-n-propyl)aminocarbonyl group, a di-(1-ethyl-2-methyl-n-propyl)aminocarbonyl group, a di-c-hexylaminocarbonyl group, a di-(1-methyl-c-pentyl)aminocarbonyl group, a di-(2-methyl-c-pentyl)aminocarbonyl group, a di-(3-methyl-c-pentyl)aminocarbonyl group, a di-(1-ethyl-c-butyl)aminocarbonyl group, a di-(2-ethyl-c-butyl)aminocarbonyl group, a di-(3-ethyl-c-butyl)aminocarbonyl group, a di-(1,2-dimethyl-c-butyl)aminocarbonyl group, a di-(1,3-dimethyl-c-butyl)aminocarbonyl group, a di-(2,2-dimethyl-c-butyl)aminocarbonyl group, a di-(2,3-dimethyl-c-butyl)aminocarbonyl group, a di-(2,4-dimethyl-c-butyl)aminocarbonyl group, a di-(3,3-dimethyl-c-butyl)aminocarbonyl group, a di-(1-n-propyl-c-propyl)aminocarbonyl group, a di-(2-n-propyl-c-propyl)aminocarbonyl group, a di-(1-i-propyl-c-propyl)aminocarbonyl group, a di-(2-i-propyl-c-propyl)aminocarbonyl group, a di-(1,2,2-trimethyl-c-propyl)aminocarbonyl group, a di-(1,2,3-trimethyl-c-propyl)aminocarbonyl group, a di-(2,2,3-trimethyl-c-propyl)aminocarbonyl group, a di-(1-ethyl-2-methyl-c-propyl)aminocarbonyl group, a di-(2-ethyl-1-methyl-c-propyl)aminocarbonyl group, a di-(2-ethyl-2-methyl-c-propyl)aminocarbonyl group, a di-(2-ethyl-3-methyl-c-propyl)aminocarbonyl group and the like may be mentioned.

An asymmetric di-$C_{1-6}$ alkylaminocarbonyl group may be linear, branched or a $C_{3-6}$ cycloalkylaminocarbonyl group. As specific examples, a (methyl, ethyl)aminocarbonyl group, a (methyl, n-propyl)aminocarbonyl group, a (methyl, i-propyl)aminocarbonyl group, a (methyl, c-propyl)aminocarbonyl group, a (methyl, n-butyl)aminocarbonyl group, a (methyl, i-butyl)aminocarbonyl group, a (methyl, s-butyl)aminocarbonyl group, a (methyl, t-butyl)aminocarbonyl group, a (methyl, n-pentyl)aminocarbonyl group, a (methyl, c-pentyl)aminocarbonyl group, a (methyl, n-hexyl)aminocarbonyl group, a (methyl, c-hexyl)aminocarbonyl group, a (ethyl, n-propyl)aminocarbonyl group, a (ethyl, i-propyl)aminocarbonyl group, a (ethyl, c-propyl)aminocarbonyl group, a (ethyl, n-butyl)aminocarbonyl group, a (ethyl, i-butyl)aminocarbonyl group, a (ethyl, s-butyl)aminocarbonyl group, a (ethyl, t-butyl)aminocarbonyl group, a (ethyl, n-pentyl)aminocarbonyl group, a (ethyl, c-pentyl)aminocarbonyl group, a (ethyl, n-hexyl)aminocarbonyl group, a (ethyl, c-hexyl)aminocarbonyl group, a (n-propyl, i-propyl)aminocarbonyl group, a (n-propyl, c-propyl)aminocarbonyl group, a (n-propyl, n-butyl)aminocarbonyl group, a (n-propyl, i-butyl)aminocarbonyl group, a (n-propyl, s-butyl)aminocarbonyl group, a (n-propyl, t-butyl)aminocarbonyl group, a (n-propyl, n-pentyl)aminocarbonyl group, a (n-propyl, c-pentyl)aminocarbonyl group, a (n-propyl, n-hexyl)aminocarbonyl group, a (n-propyl, c-hexyl)aminocarbonyl group, an (i-propyl, c-propyl)aminocarbonyl group, an (i-propyl, n-butyl)aminocarbonyl group, an (i-propyl, i-butyl)aminocarbonyl group, an (i-propyl, s-butyl)aminocarbonyl group, an (i-propyl, t-butyl)aminocarbonyl group, an (i-propyl, n-pentyl)aminocarbonyl group, an (i-propyl, c-pentyl)aminocarbonyl group, an (i-propyl, n-hexyl)aminocarbonyl group, an (i-propyl, c-hexyl)aminocarbonyl group, a (c-propyl, n-butyl)aminocarbonyl group, a (c-propyl, i-butyl)aminocarbonyl group, a (c-propyl, s-butyl)aminocarbonyl group, a (c-propyl, t-butyl)aminocarbonyl group, a (c-propyl, n-pentyl)aminocarbonyl group, a (c-propyl, c-pentyl)aminocarbonyl group, a (c-propyl, n-hexyl)aminocarbonyl group, a (c-propyl, c-hexyl)aminocarbonyl group, a (n-butyl, i-butyl)aminocarbonyl group, a (n-butyl, s-butyl)aminocarbonyl group, a (n-butyl, t-butyl)aminocarbonyl group, a (n-butyl, n-pentyl)aminocarbonyl group, a (n-butyl, c-pentyl)aminocarbonyl group, a (n-butyl, n-hexyl)aminocarbonyl group, a (n-butyl, c-hexyl)aminocarbonyl group, an (i-butyl, s-butyl)aminocarbonyl group, an (i-butyl, t-butyl)aminocarbonyl group, an (i-butyl, n-pentyl)aminocarbonyl group, an (i-butyl, c-pentyl)aminocarbonyl group, an (i-butyl, n-hexyl)aminocarbonyl group, an (i-butyl, c-hexyl)aminocarbonyl group, a (s-butyl, t-butyl)aminocarbonyl group, a (s-butyl, n-pentyl)aminocarbonyl group, a (s-butyl, c-pentyl)aminocarbonyl group, a (s-butyl, n-hexyl)aminocarbonyl group, a (s-butyl, c-hexyl)aminocarbonyl group, a (t-butyl, n-pentyl)aminocarbonyl group, a (t-butyl, c-pentyl)aminocarbonyl group, a (t-butyl, n-hexyl)aminocarbonyl group, a (t-butyl, c-hexyl)aminocarbonyl group, a (n-pentyl, c-pentyl)aminocarbonyl group, a (n-pentyl, n-hexyl)aminocarbonyl group, a (n-pentyl, c-hexyl)aminocarbonyl group, a (c-pentyl, n-hexyl)aminocarbonyl group, a (c-pentyl, c-hexyl)aminocarbonyl group, a (n-hexyl, c-hexyl)aminocarbonyl group and the like may be mentioned.

A $C_{1-6}$ alkylcarbonyl group is a carbonyl group having a $C_{1-6}$ alkyl group and may be linear, branched or a $C_{3-6}$ cycloalkylcarbonyl group. As specific examples, a methylcarbonyl group, an ethylcarbonyl group, a n-propylcarbonyl group, an i-propylcarbonyl group, a c-propylcarbonyl group, a n-butylcarbonyl group, an i-butylcarbonyl group, a s-butylcarbonyl group, a t-butylcarbonyl group, a c-butylcarbonyl group, a 1-methyl-c-propylcarbonyl group, a 2-methyl-c-propylcarbonyl group, a n-pentylcarbonyl group, a 1-methyl-n-butylcarbonyl group, a 2-methyl-n-butylcarbonyl group, a 3-methyl-n-butylcarbonyl group, a 1,1-dimethyl-n-propylcarbonyl group, a 1,2-dimethyl-n-propylcarbonyl group, a 2,2-dimethyl-n-propylcarbonyl group, a 1-ethyl-n-propylcarbonyl group, a c-pentylcarbonyl group, a 1-methyl-c-butylcarbonyl group, a 2-methyl-c-butylcarbonyl group, a 3-methyl-c-butylcarbonyl group, a 1,2-dimethyl-c-propylcarbonyl group, a 2,3-dimethyl-c-propylcarbonyl group, a 1-ethyl-c-propylcarbonyl group, a 2-ethyl-c-propylcarbonyl group, a n-hexylcarbonyl group, a 1-methyl-n-pentylcarbonyl group, a 2-methyl-n-pentylcarbonyl group, a 3-methyl-n-pentylcarbonyl group, a 4-methyl-n-pentylcarbonyl group, a 1,1-dimethyl-n-butylcarbonyl group, a 1,2-dimethyl-n-butylcarbonyl group, a 1,3-dimethyl-n-butylcarbonyl group, a 2,2-dimethyl-n-butylcarbonyl group, a 2,3-dimethyl-n-butylcarbonyl group, a 3,3-dimethyl-n-butylcarbonyl group, a 1-ethyl-n-butylcarbonyl group, a 2-ethyl-n-butylcarbonyl group, a 1,1,2-trimethyl-n-propylcarbonyl group, a 1,2,2-trimethyl-n-propylcarbonyl group, a 1-ethyl-1-methyl-n-propylcarbonyl group, a 1-ethyl-2-methyl-n-propylcarbonyl group, a c-hexylcarbonyl group, a 1-methyl-c-pentylcarbonyl group, a 2-methyl-c-pentylcarbonyl group, a 3-methyl-c-pentylcarbonyl group, a 1-ethyl-c-butylcarbonyl group, a 2-ethyl-c-butylcarbonyl group, a 3-ethyl-c-butylcarbonyl group, a 1,2-dimethyl-c-butylcarbonyl group, a 1,3-dimethyl-c-butylcarbonyl group, a 2,2-dimethyl-c-butylcarbonyl group, a 2,3-dimethyl-c-butylcarbonyl group, a 2,4-dimethyl-c-butylcarbonyl group, a 3,3-dimethyl-c-butylcarbonyl group, a 1-n-propyl-c-propylcarbonyl group, a 2-n-propyl-c-propylcarbonyl group, a 1-i-propyl-c-propylcarbonyl group, a 2-i-propyl-c-propylcarbonyl group, a 1,2,2-trimethyl-c-propylcarbonyl group, a 1,2,3-trimethyl-c-propylcarbonyl group, a 2,2,3-trimethyl-c-propylcarbonyl group, a 1-ethyl-2-methyl-c-propylcarbonyl group, a 2-ethyl-1-methyl-c-propylcarbonyl group, a 2-ethyl-2-methyl-c-propylcarbonyl group, a 2-ethyl-3-methyl-c-propylcarbonyl group and the like may be mentioned.

A $C_{1-6}$ alkloxycarbonyl group is a carbonyl group having a $C_{1-6}$ alkoxy group and may be linear, branched or a $C_{3-6}$ cycloalkoxycarbonyl group. As specific examples, a methoxycarbonyl group, an ethoxycarbonyl group, a n-propoxycarbonyl group, an i-propoxycarbonyl group, a c-propoxycarbonyl group, a n-butoxycarbonyl group, an i-butoxycarbonyl group, a s-butoxycarbonyl group, a t-butoxycarbonyl group, a c-butoxycarbonyl group, a 1-methyl-c-propoxycarbonyl group, a 2-methyl-c-propoxycarbonyl group, a n-pentyloxycarbonyl group, a 1-methyl-n-butoxycarbonyl group, a 2-methyl-n-butoxycarbonyl group, a 3-methyl-n-butoxycarbonyl group, a 1,1-dimethyl-n-propoxycarbonyl group, a 1,2-dimethyl-n-propoxycarbonyl group, a 2,2-dimethyl-n-propoxycarbonyl group, a 1-ethyl-n-propoxycarbonyl group, a c-pentyloxycarbonyl group, a 1-methyl-c-butoxycarbonyl group, a 2-methyl-c-butoxycarbonyl group, a 3-methyl-c-butoxycarbonyl group, a 1,2-dimethyl-c-propoxycarbonyl group, a 2,3-dimethyl-c-propoxycarbonyl group, a 1-ethyl-c-propoxycarbonyl group, a 2-ethyl-c-propoxycarbonyl group, a n-hexyloxycarbonyl group, a 1-methyl-n-pentyloxycarbonyl group, a 2-methyl-n-pentyloxycarbonyl group, a 3-methyl-n-pentyloxycarbonyl group, a 4-methyl-n-pentyloxycarbonyl group, a 1,1-dimethyl-n-butoxycarbonyl group, a 1,2-dimethyl-n-butoxycarbonyl group, a 1,3-dimethyl-n-butoxycarbonyl group, a 2,2-dimethyl-n-butoxycarbonyl group, a 2,3-dimethyl-n-butoxycarbonyl group, a 3,3-dimethyl-n-butoxycarbonyl group, a 1-ethyl-n-butoxycarbonyl group, a 2-ethyl-n-butoxycarbonyl group, a 1,1,2-trimethyl-n-propoxycarbonyl group, a 1,2,2-trimethyl-n-propoxycarbonyl group, a 1-ethyl-1-methyl-n-propoxycarbonyl group, a 1-ethyl-2-methyl-n-propoxycarbonyl group, a c-hexyloxycarbonyl group, a 1-methyl-c-pentyloxycarbonyl group, a 2-methyl-c-pentyloxycarbonyl group, a 3-methyl-c-pentyloxycarbonyl group, a 1-ethyl-c-butoxycarbonyl group, a 2-ethyl-c-butoxycarbonyl group, a 3-ethyl-c-butoxycarbonyl group, a 1,2-dimethyl-c-butoxycarbonyl group, a 1,3-dimethyl-c-butoxycarbonyl group, a 2,2-dimethyl-c-butoxycarbonyl group, a 2,3-dimethyl-c-butoxycarbonyl group, a 2,4-dimethyl-c-butoxycarbonyl group, a 3,3-dimethyl-c-butoxycarbonyl group, a 1-n-propyl-c-propoxycarbonyl group, a 2-n-propyl-c-propoxycarbonyl group, a 1-i-propyl-c-propoxycarbonyl group, a 2-i-propyl-c-propoxycarbonyl group, a 1,2,2-trimethyl-c-propoxycarbonyl group, a 1,2,3-trimethyl-c-propoxycarbonyl group, a 2,2,3-trimethyl-c-propoxycarbonyl group, a 1-ethyl-2-methyl-c-propoxycarbonyl group, a 2-ethyl-1-methyl-c-propoxycarbonyl group, a 2-ethyl-2-methyl-c-propoxycarbonyl group, a 2-ethyl-3-methyl-c-propoxycarbonyl and the like may be mentioned.

A $C_{1-6}$ alkylcarbonylamino group is an amino group having a $C_{1-6}$ alkylcarbonyl group and may be linear or branched or may contain a $C_{3-6}$ cycloalkylcarbonylamino group. As specific examples, a methylcarbonylamino group, an ethylcarbonylamino group, a n-propylcarbonylamino group, an i-propylcarbonylamino group, a c-propylcarbonylamino group, a n-butylcarbonylamino group, an i-butylcarbonylamino group, a s-butylcarbonylamino group, a t-butylcarbonylamino group, a c-butylcarbonylamino group, a 1-methyl-c-propylcarbonylamino group, a 2-methyl-c-propylcarbonylamino group, a n-pentylcarbonylamino group, a 1-methyl-n-butylcarbonylamino group, a 2-methyl-n-butylcarbonylamino group, a 3-methyl-n-butylcarbonylamino group, a 1,1-dimethyl-n-propylcarbonylamino group, a 1,2-dimethyl-n-propylcarbonylamino group, a 2,2-dimethyl-n-propylcarbonylamino group, a 1-ethyl-n-propylcarbonylamino group, a c-pentylcarbonylamino group, a 1-methyl-c-butylcarbonylamino group, a 2-methyl-c-butylcarbonylamino group, a 3-methyl-c-butylcarbonylamino group, a 1,2-dimethyl-c-propylcarbonylamino group, a 2,3-dimethyl-c-propylcarbonylamino group, a 1-ethyl-c-propylcarbonylamino group, a 2-ethyl-c-propylcarbonylamino group, a n-hexylcarbonylamino group, a 1-methyl-n-pentylcarbonylamino group, a 2-methyl-n-pentylcarbonylamino group, a 3-methyl-n-pentylcarbonylamino group, a 4-methyl-n-pentylcarbonylamino group, a 1,1-dimethyl-n-butylcarbonylamino group, a 1,2-dimethyl-n-butylcarbonylamino group, a 1,3-dimethyl-n-butylcarbonylamino group, a 2,2-dimethyl-n-butylcarbonylamino group, a 2,3-dimethyl-n-butylcarbonylamino group, a 3,3-dimethyl-n-butylcarbonylamino group, a 1-ethyl-n-butylcarbonylamino group, a 2-ethyl-n-butylcarbonylamino group, a 1,1,2-trimethyl-n-propylcarbonylamino group, a 1,2,2-trimethyl-n-propylcarbonylamino group, a 1-ethyl-1-methyl-n-propylcarbonylamino group, a 1-ethyl-2-methyl-n-propylcarbonylamino group, a c-hexylcarbonylamino group, a 1-methyl-c-pentylcarbonylamino group, a 2-methyl-c-pentylcarbonylamino group, a 3-methyl-c-pentylcarbonylamino group, a 1-ethyl-c-butylcarbonylamino group, a 2-ethyl-c-butylcarbonylamino group, a 3-ethyl-c-butylcarbonylamino group, a 1,2-dimethyl-c-butylcarbonylamino group, a 1,3-dimethyl-c-butylcarbonylamino group, a 2,2-dimethyl-c-butylcarbonylamino group, a 2,3-dimethyl-c-butylcarbonylamino group, a 2,4-dimethyl-c-butylcarbonylamino group, a 3,3-dimethyl-c-butylcarbonylamino group, a 1-n-propyl-c-propylcarbonylamino group, a 2-n-propyl-c-propylcarbonylamino group, a 1-i-propyl-c-propylcarbonylamino group, a 2-i-propyl-c-propylcarbonylamino group, a 1,2,2-trimethyl-c-propylcarbonylamino group, a 1,2,3-trimethyl-c-propylcarbonylamino group, a 2,2,3-trimethyl-c-propylcarbonylamino group, a 1-ethyl-2-methyl-c-propylcarbonylamino group, a 2-ethyl-1-methyl-c-propylcarbonylamino group, a 2-ethyl-2-methyl-c-propylcarbonylamino group, a 2-ethyl-3-methyl-c-propylcarbonylamino group and the like may be mentioned.

A $C_{2-14}$ aryl group fused to a $C_{2-9}$ heterocyclyl group means a structure consisting of a $C_{2-9}$ heterocyclyl group and a $C_{2-14}$ aryl group fused together.

Herein, the $C_{2-9}$ heterocyclyl group is restricted so as to exclude $C_{2-9}$ heterocyclyl groups which aromatize upon fusion to the aryl group, such as a dihydropyrrolyl group, which forms an indole ring upon fusion to a phenyl group.

As specific examples of the $C_{2-14}$ aryl group fused to a $C_{2-9}$ heterocyclyl group, the following structures may be mentioned.

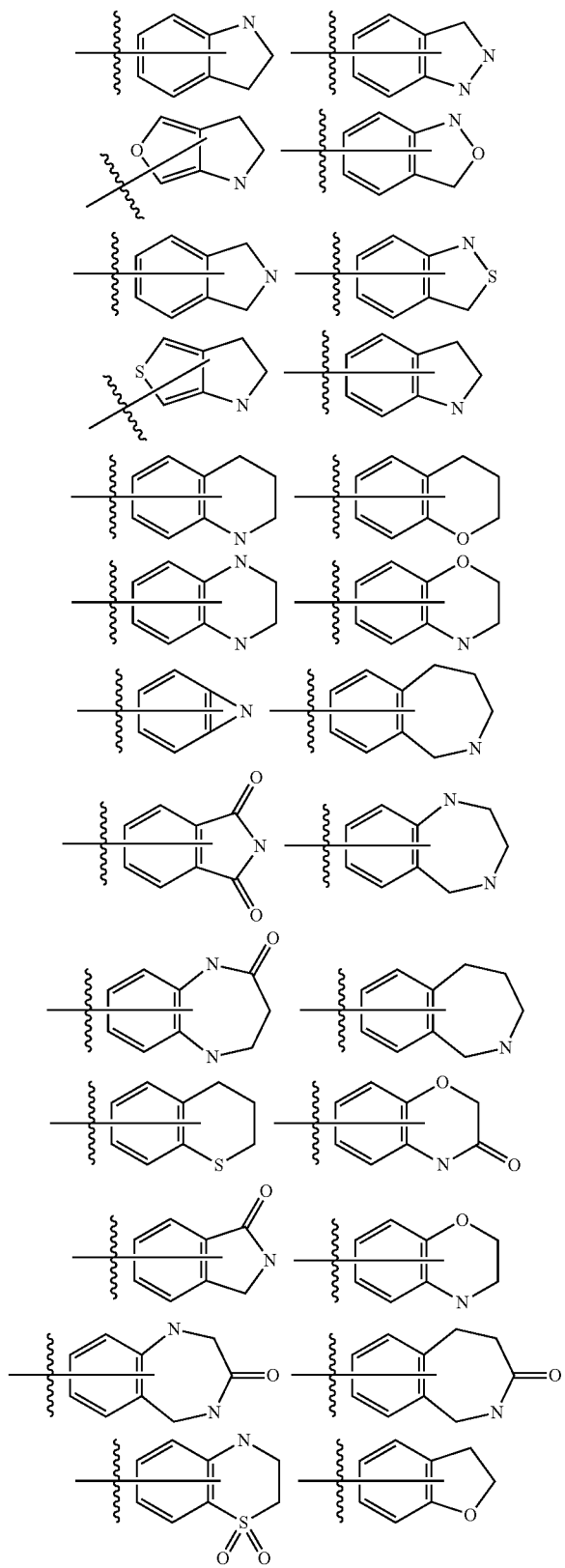

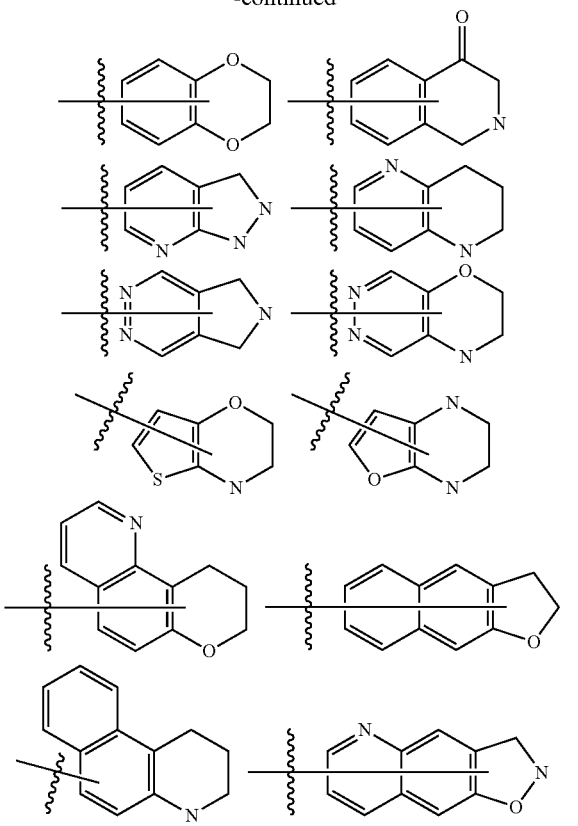

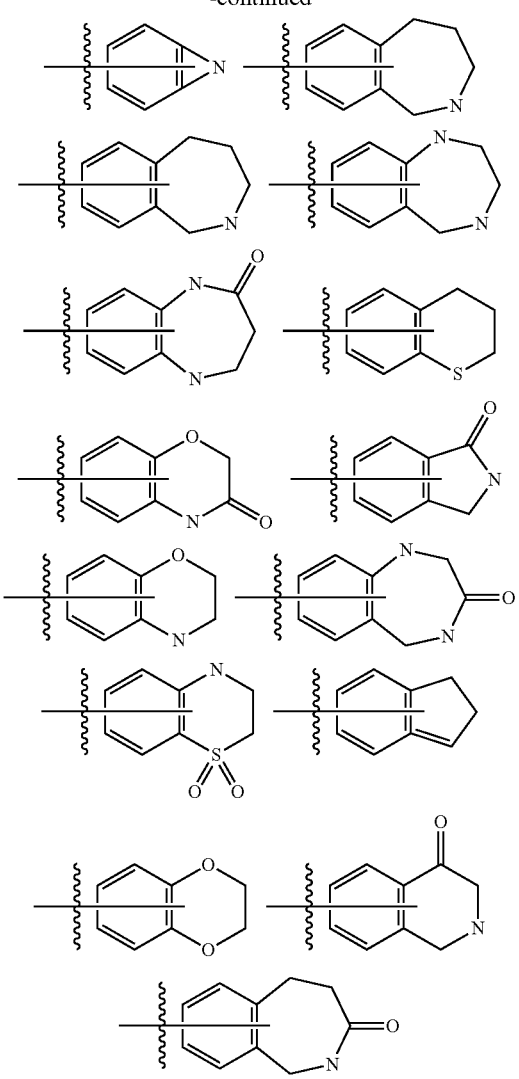

A phenyl group fused to a $C_{2-9}$ heterocyclyl group means a structure consisting of the above-mentioned $C_{2-9}$ heterocyclyl group and a phenyl group fused together, sharing two carbon atoms.

Herein, the $C_{2-9}$ heterocyclyl group is restricted so as to exclude $C_{2-9}$ heterocyclyl groups which aromatize upon fusion to the phenyl group, such as a dihydropyrrolyl group, which forms an indole ring upon fusion to a phenyl group.

As specific examples of the phenyl group fused to a $C_{2-9}$ heterocyclyl group, the following structures may be mentioned.

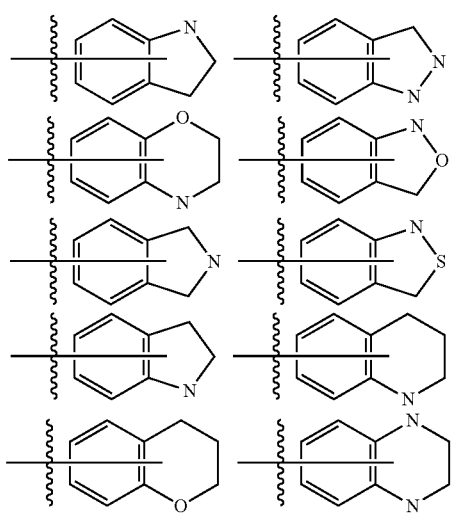

A $C_{2-14}$ aryl group fused to a $C_{3-10}$ cycloalkyl group means a structure consisting of a $C_{3-10}$ cycloalkyl group and the above-mentioned $C_{2-14}$ aryl group fused together, and as specific example, the following structures may be mentioned.

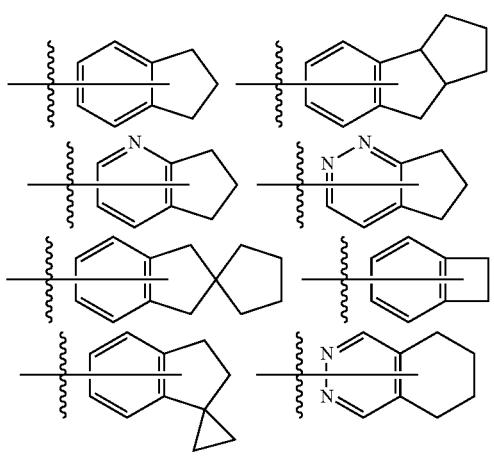

-continued

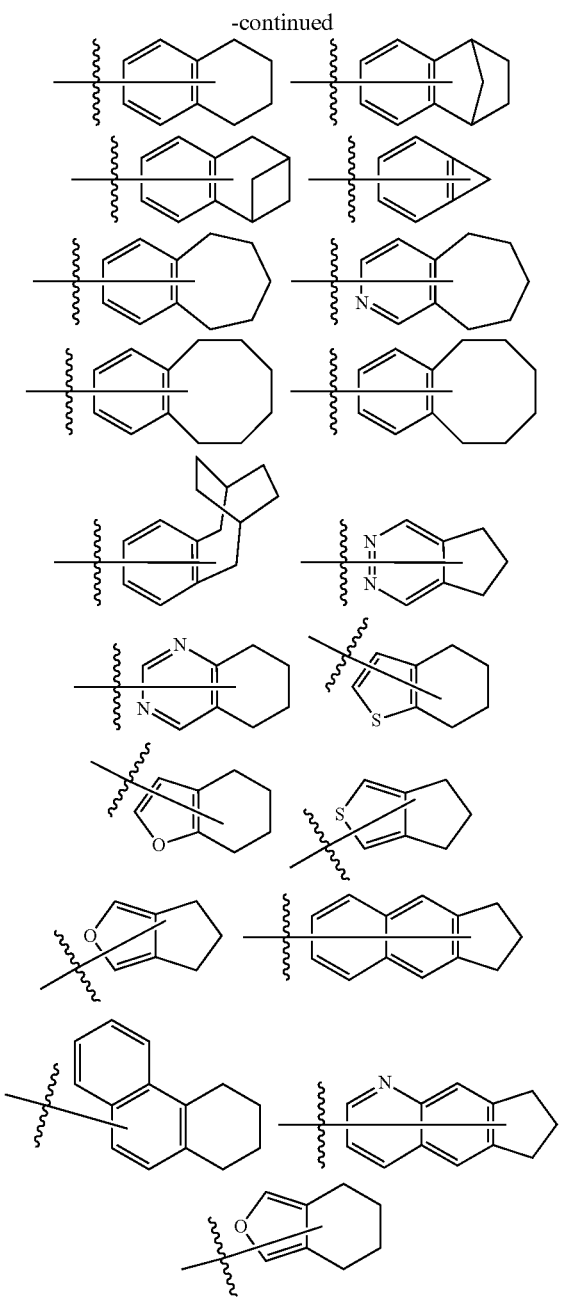

A phenyl group fused to a $C_{3-10}$ cycloalkyl group means a structure consisting of a $C_{3-10}$ cycloalkyl group and a phenyl group fused together, sharing two carbon atoms, and as specific example, the following structures may be mentioned.

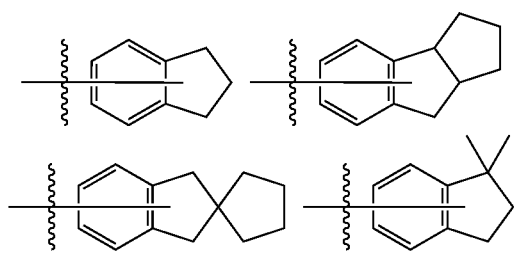

-continued

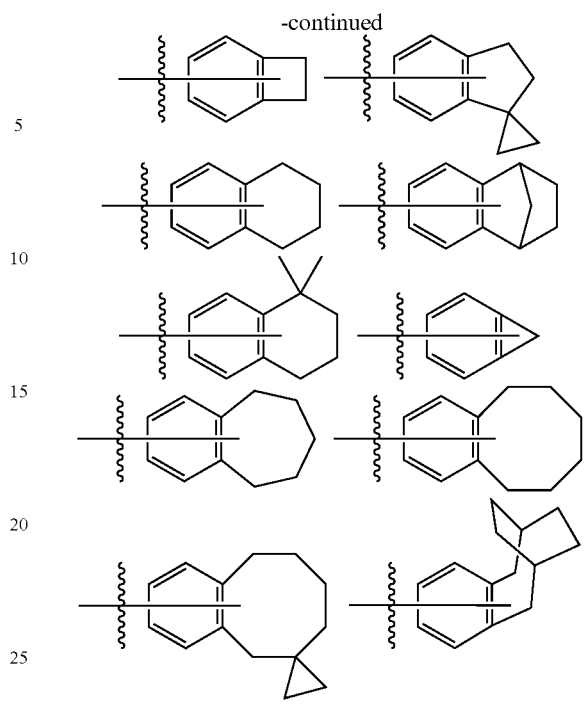

A phenyl group fused to a $C_{4-7}$ cycloalkyl group means a structure consisting of a $C_{4-7}$ cycloalkyl group and a phenyl group fused together, sharing two carbon atoms, and as specific example, the following structures may be mentioned.

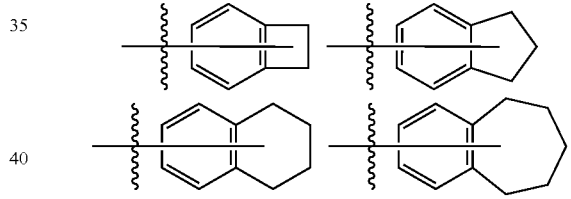

A phenyl group fused to a $C_{3-5}$ oxygen-containing heterocyclyl group means a structure consisting of the above-mentioned $C_{3-5}$ oxygen-containing heterocyclyl group and a phenyl group fused together, sharing two carbon atoms, and the $C_{3-5}$ oxygen-containing heterocyclyl group constituting the ring is a non-aromatic heterocyclic group. As specific example, the following structures may be mentioned.

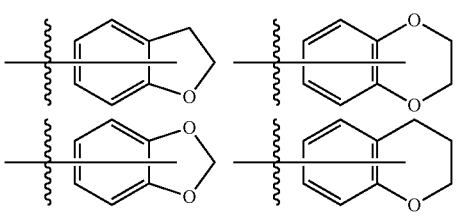

A $C_{2-14}$ aryl group fused to a $C_{3-10}$ cycloalkenyl group means a structure consisting of the above-mentioned $C_{3-10}$ cycloalkenyl group and the above-mentioned $C_{2-14}$ aryl group fused together, and as specific example, the following structures may be mentioned.

Herein, the $C_{3-10}$ cycloalkenyl group is restricted to exclude $C_{3-10}$ cycloalkenyl groups which aromatize upon fusion to the $C_{2-14}$ aryl group, such as a c-hexa-1,3-dienyl group, which forms a napthalene ring upon fusion to a phenyl group.

As specific examples the $C_{2-14}$ aryl group fused to a $C_{3-10}$ cycloalkenyl group, the following structures may be mentioned.

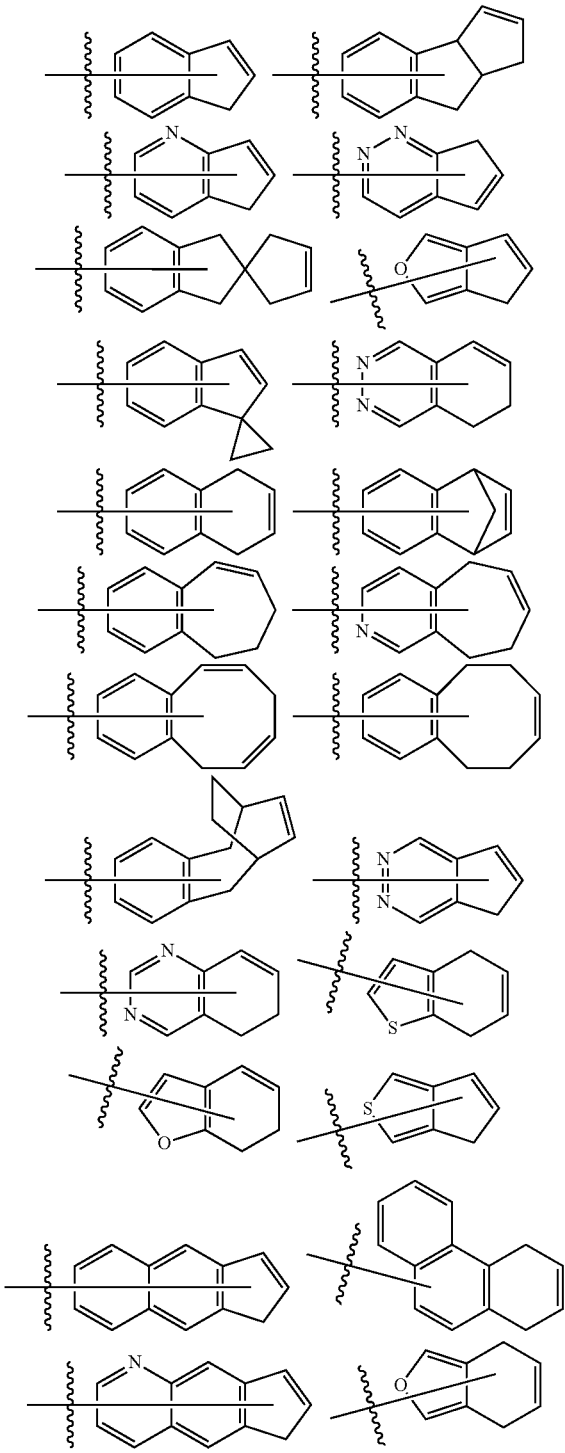

Next, preferred structures of the respective substituents will be mentioned.

A preferred embodiment of the substituents A and B is such that A is a nitrogen atom or $CR^4$ (wherein $R^4$ is a hydrogen atom, a halogen atom or a $C_{1-6}$ alkyl group (the $C_{1-6}$ alkyl group is unsubstituted or substituted with one or more halogen atoms)), and B is $NR^5$ (wherein $R^5$ is a $C_{1-6}$ alkyl group (the $C_{1-6}$ alkyl group is unsubstituted or substituted with one or more halogen atoms)) or a sulfur atom.

A more preferred embodiment of the substituents A and B is such that A is a nitrogen atom, B is $NR^5$ (wherein $R^5$ is a $C_{1-6}$ alkyl group (the $C_{1-6}$ alkyl group is unsubstituted or substituted with one or more halogen atoms)).

Another more preferred embodiment of the substituents A and B is such that A is $CR^4$ (wherein $R^4$ is a hydrogen atom, a halogen atom or a $C_{1-6}$ alkyl group (the $C_{1-6}$ alkyl group is unsubstituted or substituted with one or more halogen atoms)), and B is a sulfur atom.

A more particularly preferred embodiment of the substituents A and B is such that A is a nitrogen atom, and B is $NR^5$ (wherein $R^5$ is a $C_{1-3}$ alkyl group).

Another more particularly preferred embodiment of the substituents A and B is such that A is $CR^4$ (wherein $R^4$ is a hydrogen atom), and B is a sulfur atom.

A preferred embodiment of the substituent $R^1$ is a $C_{2-14}$ aryl group fused to a $C_{3-10}$ cycloalkenyl group (the $C_{2-14}$ aryl group fused to a $C_{3-10}$ cycloalkenyl group is unsubstituted or substituted with one or more substituents selected from the group consisting of carboxy groups, carbamoyl groups, sulfamoyl groups, phosphono groups, sulfo groups, tetrazolyl groups, formyl groups, hydroxy groups, nitro groups, cyano groups, halogen atoms, $C_{1-6}$ alkyl groups, $C_{1-3}$ haloalkyl groups, $C_{1-3}$ haloalkoxy groups, alkenyl groups, $C_{2-9}$ heterocyclyl groups, mono-$C_{1-6}$ alkylaminocarbonyl groups, di-$C_{1-6}$ alkylaminocarbonyl groups and $C_{1-6}$ alkylsulfonyl groups).

Another preferred embodiment of the substituent $R^1$ is a phenyl group fused to a $C_{3-10}$ cycloalkyl group (the phenyl group fused to a $C_{3-10}$ cycloalkenyl group is unsubstituted or substituted with one or more substituents selected from the group consisting of carboxy groups, carbamoyl groups, sulfamoyl groups, phosphono groups, sulfo groups, tetrazolyl groups, formyl groups, hydroxy groups, nitro groups, cyano groups, halogen atoms, $C_{1-6}$ alkyl groups, $C_{1-3}$ haloalkyl groups, $C_{1-3}$ haloalkoxy groups, $C_{2-6}$ alkenyl groups, $C_{2-9}$ heterocyclyl groups, mono-$C_{1-6}$ alkylaminocarbonyl groups, di-$C_{1-6}$ alkylaminocarbonyl groups and $C_{1-6}$ alkylsulfonyl groups).

Another preferred embodiment of the substituent $R^1$ is a phenyl group fused to a $C_{2-9}$ heterocyclyl group (the phenyl group fused to a $C_{2-9}$ heterocyclyl group is unsubstituted or substituted with one or more substituents selected from the group consisting of carboxy groups, carbamoyl groups, sulfamoyl groups, phosphono groups, sulfo groups, tetrazolyl groups, formyl groups, hydroxy groups, nitro groups, cyano groups, halogen atoms, $C_{1-6}$ alkyl groups, $C_{1-3}$ haloalkyl groups, $C_{1-3}$ haloalkoxy groups, alkenyl groups, $C_{2-9}$ heterocyclyl groups, mono-$C_{1-6}$ alkylaminocarbonyl groups, di-$C_{1-6}$ alkylaminocarbonyl groups and $C_{1-6}$ alkylsulfonyl groups).

A more preferred embodiment of the substituent $R^1$ is a phenyl group fused to a $C_{2-9}$ heterocyclyl group.

Another more preferred embodiment of the substituent $R^1$ is a phenyl group fused to a $C_{3-10}$ cycloalkyl group.

A particularly preferred embodiment of the substituent $R^1$ is a phenyl group fused to a $C_{3-5}$ oxygen-containing heterocyclyl group.

Another particularly preferred embodiment of the substituent $R^1$ is a phenyl group fused to a $C_{4-7}$ cycloalkyl group.

Another particularly preferred embodiment of the substituent R¹ is any of the following structures.

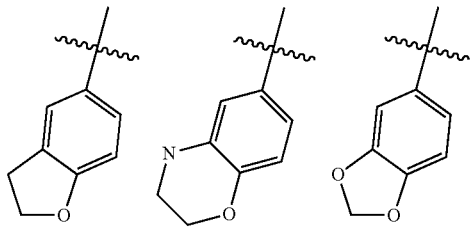

Another particularly preferred embodiment of the substituent R¹ is any of the following structures.

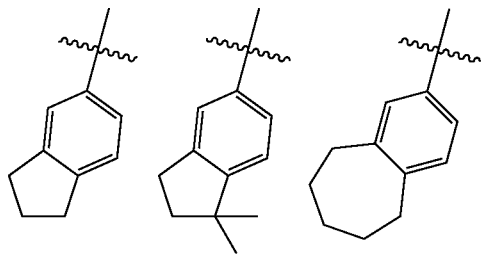

Another particularly preferred embodiment of the substituent R¹ is any of the following structures.

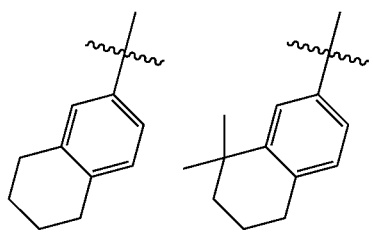

A more particularly preferred embodiment of the substituent R¹ is an indanyl group.

Another particularly preferred embodiment of the substituent R¹ is a tetrahydronaphthyl group.

Another particularly preferred embodiment of the substituent R¹ is a 2,3-dihydrobenzofuranyl group.

Preferred embodiments of the substituents $L^1$ and $L^2$ are single bonds.

A preferred embodiment of X is OH.

A preferred embodiment of the substituent $R^2$ is preferably a hydrogen atom, a $C_{1-6}$ alkyl group or a $C_{2-6}$ alkenyl group (the $C_{1-6}$ alkyl group and the $C_{2-6}$ alkenyl group are unsubstituted or substituted with one or more halogen atoms).

Another preferred embodiment of the substituent $R^2$ is a hydrogen atom, a $C_{1-6}$ alkyl group (the $C_{1-6}$ alkyl group is unsubstituted or substituted with one or more halogen atoms).

A more particularly preferred embodiment of the substituent $R^2$ is a methyl group.

A preferred embodiment of $L^3$ is $NR^8$ (wherein $R^8$ is a hydrogen atom or a $C_{1-6}$ alkyl group (the $C_{1-6}$ alkyl group is unsubstituted or substituted with one or more halogen atoms)).

A more preferred embodiment of $L^3$ is NH.

A preferred embodiment of $L^4$ is a single bond or $NR^8$ (wherein $R^8$ is a hydrogen atom or a $C_{1-6}$ alkyl group (the $C_{1-6}$ alkyl group is unsubstituted or substituted with one or more halogen atoms)).

A more preferred embodiment of $L^4$ is a single bond or NH.

A preferred embodiment of Y is an oxygen atom or a sulfur atom.

A preferred embodiment of $R^3$ is a $C_{4-6}$ aryl group substituted with a carboxy group or a $C_{1-6}$ alkoxycarbonyl group.

Another preferred embodiment of $R^3$ is a $C_{4-6}$ aryl group substituted with a carboxy group or a $C_{1-6}$ alkoxycarbonyl group and with a substituent selected from the group consisting of a halogen atom, a cyano group and a nitro group.

Another preferred embodiment of $R^3$ is a $C_{4-6}$ aryl group substituted with a $CONR^{14}R^{15}$ (wherein $R^{14}$ is a hydrogen atom or a $C_{1-6}$ alkyl group, and $R^{15}$ is a $C_{1-6}$ alkyl group (the $C_{1-6}$ alkyl group is unsubstituted or substituted with one or more $C_{4-6}$ aryl groups), or $NR^{14}R^{15}$, as a whole, means a $C_{4-6}$ nitrogen-containing heterocyclyl group (the $C_{4-6}$ nitrogen-containing heterocyclyl group is unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more hydroxy groups, one or more $C_{1-6}$ alkyl groups, one or more $C_{1-3}$ haloalkyl groups, one or more $C_{1-3}$ haloalkoxy groups, one or more $C_{2-6}$ alkenyl groups, one or more $C_{2-9}$ heterocyclyl groups, one or more mono-$C_{1-6}$ alkylaminocarbonyl groups, one or more di-$C_{1-6}$ alkylaminocarbonyl groups or one or more $C_{1-6}$ alkylsulfonyl groups)).

Another preferred embodiment of $R^3$ is a $C_{4-6}$ nitrogen-containing heterocyclyl group substituted with a substituent selected from the group consisting of a carboxy group, a $C_{1-6}$ alkoxycarbonyl group, a $C_{1-6}$ alkylcarbonyl group, a mono-$C_{1-6}$ alkylaminocarbonyl group and a di-$C_{1-6}$ alkylaminocarbonyl group.

Another preferred embodiment of $R^3$ is a $C_{4-6}$ aryl group (the $C_{4-6}$ aryl group is substituted with a tetrazolyl group).

Another preferred embodiment of $R^3$ is a $C_{4-6}$ aryl group (the $C_{4-6}$ aryl group is substituted with a mono-$C_{1-6}$ alkylaminocarbonyl group (the mono-$C_{1-6}$ alkylaminocarbonyl group is substituted with a $C_{4-6}$ aryl group (the $C_{4-6}$ aryl group is substituted with a mono-$C_{1-6}$ alkylaminocarbonyl group (the mono-$C_{1-6}$ alkylaminocarbonyl group is substituted with a hydroxy group))))).

A more preferred embodiment of $R^3$ is a phenyl group substituted with a carboxy group or a $C_{1-6}$ alkoxycarbonyl group and with a substituent selected from a halogen atom, a cyano group and a nitro group.

Another more preferred embodiment of $R^3$ is a $C_{4-6}$ aryl group substituted with a carboxy group or a $C_{1-6}$ alkoxycarbonyl group.

Another more preferred embodiment of $R^3$ is a $C_{4-6}$ aryl group substituted with a $CONR^{14}R^{15}$ (wherein $R^{14}$ is a hydrogen atom or a $C_{1-3}$ alkyl group, and $R^{15}$ is a $C_{1-3}$ alkyl group (the $C_{1-3}$ alkyl group is unsubstituted or substituted with one or more $C_{4-6}$ aryl groups), or $NR^{14}R^{15}$, as a whole, means a $C_{4-5}$ nitrogen-containing heterocyclyl group).

Another more preferred embodiment of $R^3$ is a $C_{4-5}$ nitrogen-containing heterocyclyl group substituted with a carboxy group or a $C_{1-6}$ alkoxycarbonyl group.

A more particularly preferred embodiment of $R^3$ is a phenyl group substituted with a carboxy group.

Another more particularly preferred embodiment of $R^3$ is a phenyl group substituted with a carboxy group and with a substituent selected from the group consisting of a nitro group and a halogen atom.

Another more particularly preferred embodiment of $R^3$ is a thienyl group substituted with a carboxy group.

Another more particularly preferred embodiment of $R^3$ is a thienyl group substituted with a $CONR^{14}R^{15}$ (wherein $R^{14}$ is a hydrogen atom or a $C_{1-3}$ alkyl group, and $R^{15}$ is a $C_{1-3}$ alkyl group (the $C_{1-3}$ alkyl group is unsubstituted or substituted with one or more $C_{4-6}$ aryl groups)).

Another more particularly preferred embodiment of $R^3$ is a thienyl group substituted with a $CONR^{14}R^{15}$ (wherein $NR^{14}R^{15}$, as a whole, means a $C_{4-5}$ nitrogen-containing heterocyclyl group).

Another more particularly preferred embodiment of $R^3$ is a thienyl group substituted with a substituent selected from the group consisting of a di-$C_{1-6}$ alkylaminocarbonyl group, a mono-$C_{1-6}$ alkylaminocarbonyl group (the mono-$C_{1-6}$ alkylaminocarbonyl group is substituted with a pyridyl group) and a pyrrolidine-1-carbonyl group.

Another more particularly preferred embodiment of $R^3$ is a piperidinyl group or a piperazinyl group substituted with a carboxy group.

Another more particularly preferred embodiment of $R^3$ is a phenyl group substituted with a tetrazolyl group.

Another more particularly preferred embodiment of $R^3$ is a thienyl group (the thienyl group is substituted with a mono-$C_{1-6}$ alkylaminocaronyl group (the mono-$C_{1-6}$ alkylaminocaronyl group is substituted with a phenyl group (the phenyl group is substituted with a mono-$C_{1-6}$ alkylaminocaronyl group (the mono-$C_{1-6}$ alkylaminocaronyl group is substituted with a hydroxy group)))).

Favorable compounds of the present invention for use in the preventive, therapeutic and improving agent for diseases against which a thrombopoietin receptor activator is effective are as follows.

(1) Compounds represented by the formula (I) wherein A is $CR^4$ (wherein $R^4$ is a hydrogen atom, a halogen atom or a $C_{1-6}$ alkyl group (the $C_{1-6}$ alkyl group is unsubstituted or substituted with one or more halogen atoms)) or a nitrogen atom, B is a sulfur atom or $NR^5$ (wherein $R^5$ is a $C_{1-6}$ alkyl group (the $C_{1-6}$ alkyl group is unsubstituted or substituted with one or more halogen atoms)), The substituent $R^1$ is a $C_{2-14}$ aryl group fused to a $C_{3-10}$ cycloalkyl group or a $C_{2-14}$ aryl group fused to a $C_{2-9}$ heterocyclyl group (wherein the $C_{2-14}$ aryl group fused to a $C_{3-10}$ cycloalkyl group and the $C_{2-14}$ aryl group fused to a $C_{2-9}$ heterocyclyl group are unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more $C_{1-6}$ alkyl groups, one or more $C_{2-6}$ alkenyl groups, one or more $C_{2-9}$ heterocyclyl groups, one or more mono-$C_{1-6}$ alkylaminocarbonyl groups, one or more di-$C_{1-6}$ alkylaminocarbonyl groups or one or more $C_{1-6}$ alkylsulfonyl groups), the substituents $L^1$ and $L^2$ are single bonds, X is OH, the substituent $R^2$ is a hydrogen atom, a $C_{1-6}$ alkyl group or a $C_{2-6}$ alkenyl group (the $C_{1-6}$ alkyl group and the $C_{2-6}$ alkenyl group are unsubstituted or substituted with one or more halogen atoms), $L^3$ is $NR^8$ (wherein $R^8$ is a hydrogen atom or a $C_{1-6}$ alkyl group (the $C_{1-6}$ alkyl group is unsubstituted or substituted with one or more halogen atoms)), $L^4$ is a single bond or $NR^8$ (wherein $R^8$ is a hydrogen atom or a $C_{1-6}$ alkyl group (the $C_{1-6}$ alkyl group is unsubstituted or substituted with one or more halogen atoms)), Y is an oxygen atom or a sulfur atom, $R^3$ is a $C_{2-14}$ aryl group (the $C_{2-14}$ aryl group is substituted with a carboxy group), a $C_{2-14}$ aryl group (the $C_{2-14}$ aryl group is substituted with a carboxy group and with a substituent selected from the group consisting of a halogen atom, a cyano group and a nitro group), a $C_{2-14}$ aryl group (the $C_{2-14}$ aryl group is substituted with a $CONR^{14}R^{15}$ (wherein $R^{14}$ is a hydrogen atom, and $R^{15}$ is a $C_{1-6}$ alkyl group (the $C_{1-6}$ alkyl group is unsubstituted or substituted with one or more $C_{2-14}$ aryl groups), or $NR^{14}R^{15}$, as a whole, means a nitrogen-containing heterocyclyl group (the nitrogen-containing heterocyclyl group is unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more hydroxy groups, one or more $C_{1-6}$ alkyl groups, one or more $C_{1-3}$ haloalkyl groups, one or more $C_{1-3}$ haloalkoxy groups, one or more $C_{2-6}$ alkenyl groups, one or more $C_{2-9}$ heterocyclyl groups, one or more mono-$C_{1-6}$ alkylaminocarbonyl groups, one or more di-$C_{1-6}$ alkylaminocarbonyl groups or one or more $C_{1-6}$ alkylsulfonyl groups))) or a $C_{2-9}$ heterocyclyl group (the $C_{2-9}$ heterocyclyl group is substituted with a carboxy group, a $C_{1-6}$ alkylcarbonyl group, a mono-$C_{1-6}$ alkylaminocarbonyl group or a di-$C_{1-6}$ alkylaminocarbonyl group), tautomers, prodrugs or pharmaceutically acceptable salts of the compounds or solvates thereof.

(2) The compounds according to (1), wherein A is $CR^4$ (wherein $R^4$ is a hydrogen atom, a halogen atom or a $C_{1-6}$ alkyl group (the $C_{1-6}$ alkyl group is unsubstituted or substituted with one or more halogen atoms)), and B is a sulfur atom, tautomers, prodrugs or pharmaceutically acceptable salts of the compounds or solvates thereof.

(3) The compounds according to (2), wherein A is $CR^4$ (wherein $R^4$ is a hydrogen atom), and B is a sulfur atom, tautomers, prodrugs or pharmaceutically acceptable salts of the compounds or solvates thereof.

(4) The compounds according to (1), wherein A is a nitrogen atom, B is $NR^5$ (wherein $R^5$ is a $C_{1-6}$ alkyl group (the $C_{1-6}$ alkyl group is unsubstituted or substituted with one or more halogen atoms)), tautomers, prodrugs or pharmaceutically acceptable salts of the compounds or solvates thereof.

(5) The compounds according to (4), wherein A is a nitrogen atom, and B is $NR^5$ (wherein $R^5$ is a $C_{1-3}$ alkyl group), tautomers, prodrugs or pharmaceutically acceptable salts of the compounds or solvates thereof.

(6) The compounds according to any one of (1) to (5), wherein $R^1$ is a phenyl group fused to a $C_{3-10}$ cycloalkyl group or a phenyl group fused to a $C_{2-9}$ heterocyclyl group (the phenyl group fused to a $C_{3-10}$ cycloalkyl group and the phenyl group fused to a $C_{2-9}$ heterocyclyl group are unsubstituted or substituted with one or more carboxy groups, one or more carbamoyl groups, one or more sulfamoyl groups, one or more phosphono groups, one or more sulfo groups, one or more tetrazolyl groups, one or more formyl groups, one or more nitro groups, one or more cyano groups, one or more halogen atoms, one or more $C_{1-6}$ alkyl groups, one or more $C_{2-6}$ alkenyl groups, one or more $C_{2-9}$ heterocyclyl groups, one or more mono-$C_{1-6}$ alkylaminocarbonyl groups, one or more di-$C_{1-6}$ alkylaminocarbonyl groups or one or more $C_{1-6}$ alkylsulfonyl groups), tautomers, prodrugs or pharmaceutically acceptable salts of the compounds or solvates thereof.

(7) The compounds according to (6), wherein $R^1$ is a phenyl group fused to a $C_{3-5}$ oxygen-containing heterocyclyl group, tautomers, prodrugs or pharmaceutically acceptable salts of the compounds or solvates thereof.

(8) The compounds according to (6), wherein $R^1$ is a phenyl group fused to a $C_{4-7}$ cycloalkyl group, tautomers, prodrugs or pharmaceutically acceptable salts of the compounds or solvates thereof.

(9) The compounds according to (6), wherein $R^1$ is any of the following structures, tautomers, prodrugs or pharmaceutically acceptable salts of the compounds or solvates thereof.

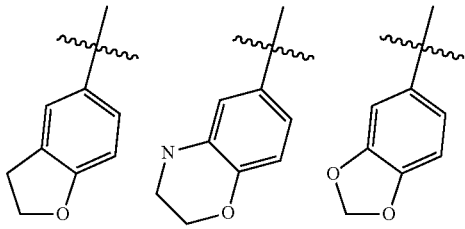

(10) The compounds according to (6), wherein $R^1$ is any of the following structures, tautomers, prodrugs or pharmaceutically acceptable salts of the compounds or solvates thereof.

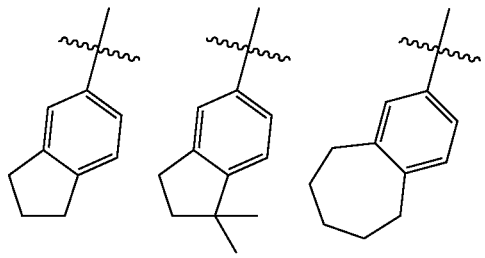

(11) The compounds according to (6), wherein $R^1$ is any of the following structures, tautomers, prodrugs or pharmaceutically acceptable salts of the compounds or solvates thereof.

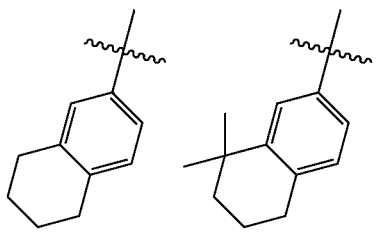

(12) The compounds according to (6), wherein $R^1$ is an indanyl group, tautomers, prodrugs or pharmaceutically acceptable salts of the compounds or solvates thereof.

(13) The compounds according to (6), wherein $R^1$ is a tetrahydronaphthyl group, tautomers, prodrugs or pharmaceutically acceptable salts of the compounds or solvates thereof.

(14) The compounds according to (6), wherein $R^1$ is a 2,3-dihydrobenzofuranyl group, tautomers, prodrugs or pharmaceutically acceptable salts of the compounds or solvates thereof.

(15) The compounds according to (1) to (14), wherein $R^2$ is a hydrogen atom or a $C_{1-6}$ alkyl group (the $C_{1-6}$ alkyl group is unsubstituted or substituted with one or more halogen atoms), tautomers, prodrugs or pharmaceutically acceptable salts of the compounds or solvates thereof.

(16) The compounds according to (15), wherein $R^2$ is a hydrogen atom or a methyl group, tautomers, prodrugs or pharmaceutically acceptable salts of the compounds or solvates thereof.

(17) The compounds according to any one of (1) to (16), wherein $L^3$ is $NR^8$ (wherein $R^8$ is a hydrogen atom or a $C_{1-6}$ alkyl group (the $C_{1-6}$ alkyl group is unsubstituted or substituted with one or more halogen atoms)), tautomers, prodrugs or pharmaceutically acceptable salts of the compounds or solvates thereof.

(18) The compounds according to (17), wherein $L^3$ is NH, tautomers, prodrugs or pharmaceutically acceptable salts of the compounds or solvates thereof.

(19) The compounds according to any of any one of (1) to (18), wherein $L^4$ is a single bond, Y is an oxygen atom, and $R^3$ is a $C_{4-6}$ aryl group substituted with a carboxy group or a $C_{1-6}$ alkoxycarbonyl group and with a substituent selected from the group consisting of a halogen atom, a cyano group and a nitro group, tautomers, prodrugs or pharmaceutically acceptable salts of the compounds or solvates thereof.

(20) The compounds according to (19), wherein $R^3$ is a phenyl group substituted with a carboxy group or a $C_{1-6}$ alkoxycarbonyl group and with a substituent selected from the group consisting of a halogen atom, a cyano group and a nitro group, tautomers, prodrugs or pharmaceutically acceptable salts of the compounds or solvates thereof.

(21) The compounds according to (20), wherein $R^3$ is a phenyl group substituted with a carboxy group and with a halogen atom, tautomers, prodrugs or pharmaceutically acceptable salts of the compounds or solvates thereof.

(22) The compounds according to any one of (1) to (18), wherein $L^4$ is a single bond, Y is an oxygen atom, and $R^3$ is a $C_{4-6}$ aryl group substituted with a $CONR^{14}R^{15}$ (wherein $R^{14}$ is a hydrogen atom or a $C_{1-6}$ alkyl group, and $R^{15}$ is a $C_{1-6}$ alkyl group (the $C_{1-6}$ alkyl group is unsubstituted or substituted with one or more $C_{2-9}$ heteroaryl groups), or $NR^{14}R^{15}$, as a whole, means a nitrogen-containing heterocyclyl group), tautomers, prodrugs or pharmaceutically acceptable salts of the compounds or solvates thereof.

(23) The compounds according to any one of (1) to (18), wherein $L^4$ is a single bond, Y is an oxygen atom, and $R^3$ is a thienyl group substituted with a $CONR^{14}R^{15}$ (wherein $R^{14}$ is a hydrogen atom or a $C_{1-3}$ alkyl group, and $R^{15}$ is a $C_{1-3}$ alkyl group (the $C_{1-3}$ alkyl group is unsubstituted or substituted with a $C_{4-6}$ aryl group), or $NR^{14}R^{15}$, as a whole, means a $C_{4-6}$ nitrogen-containing heterocyclyl group), tautomers, prodrugs or pharmaceutically acceptable salts of the compounds or solvates thereof.

(24) The compounds according to (22), wherein $R^3$ is a thienyl group substituted with a di-$C_{1-6}$ alkylaminocarbonyl group, a mono-$C_{1-6}$ alkylaminocarbonyl group (the mono-$C_{1-6}$ alkylaminocarbonyl group is substituted with a pyridyl group) or a pyrrolidine-1-carbonyl group, tautomers, prodrugs or pharmaceutically acceptable salts of the compounds or solvates thereof.

(25) The compounds according to any one of (1) to (18), wherein $L^4$ is a single bond, Y is an oxygen atom, and $R^3$ is a $C_{4-6}$ aryl group substituted with a carboxy group or a $C_{1-6}$ alkoxycarbonyl group, tautomers, prodrugs or pharmaceutically acceptable salts of the compounds or solvates thereof.

(26) The compounds according to (25), wherein $R^3$ is a phenyl group or a thienyl group substituted with a carboxy group, tautomers, prodrugs or pharmaceutically acceptable salts of the compounds or solvates thereof.

(27) The compounds according to any one of (1) to (18), wherein $L^4$ is $NR^8$ (wherein $R^8$ is a hydrogen atom or a $C_{1-6}$ alkyl group (the $C_{1-6}$ alkyl group is unsubstituted or substituted with one or more halogen atoms)), Y is a sulfur atom, and $R^3$ is a $C_{4-6}$ aryl group substituted with a carboxy group or a $C_{1-6}$ alkoxycarbonyl group, tautomers, prodrugs or pharmaceutically acceptable salts of the compounds or solvates thereof.

(28) The compounds according to (27), wherein $R^3$ is a phenyl group substituted with a carboxy group, tautomers, prodrugs or pharmaceutically acceptable salts of the compounds or solvates thereof.

(29) The compounds according to (27) or (28), wherein $L^4$ is NH, tautomers, prodrugs or pharmaceutically acceptable salts of the compounds or solvates thereof.

(30) The compounds according to any one of (1) to (18), wherein $L^4$ is a single bond, Y is a sulfur atom, and $R^3$ is a $C_{4-6}$ nitrogen-containing heterocyclyl group substituted with a substituent selected from the group consisting of a carboxy group, a $C_{1-6}$ alkoxycarbonyl group, a $C_{1-6}$ alkylcarbonyl group, a mono-$C_{1-6}$ alkylaminocarbonyl group and a di-$C_{1-6}$ alkylaminocarbonyl group, tautomers, prodrugs or pharmaceutically acceptable salts of the compounds or solvates thereof.

(31) The compounds according to any one of (1) to (18), wherein $L^4$ is a single bond, Y is a sulfur atom, and $R^3$ is any of the following structures substituted with a substituent selected from the group consisting of a carboxy group, a $C_{1-6}$ alkoxycarbonyl group, a $C_{1-6}$ alkylcarbonyl group, a mono-$C_{1-6}$ alkylaminocarbonyl group and a di-$C_{1-6}$ alkylaminocarbonyl group, tautomers, prodrugs or pharmaceutically acceptable salts of the compounds or solvates thereof.

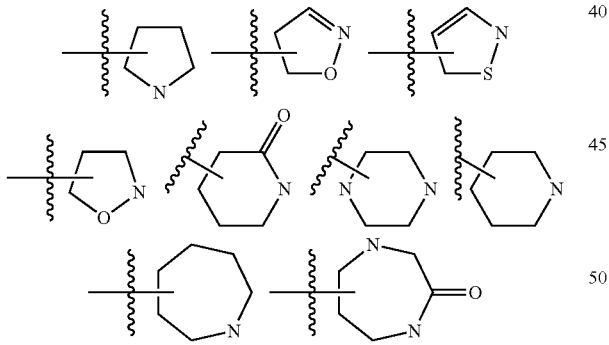

(32) The compounds according to (30) or (31), wherein $R^3$ is a piperidinyl group substituted with a carboxy group, tautomers, prodrugs or pharmaceutically acceptable salts of the compounds or solvates thereof.

(33) Compounds represented by the formula (I) wherein $R^2$ is a methyl group, $L^1$, $L^2$ and $L^4$ are single bonds, $L^3$ is NH, X is OH, A is a nitrogen atom, B is NMe, Y is an oxygen atom, and $R^1$ and $R^3$ are any of the following combinations in Table 1, tautomers, prodrugs or pharmaceutically acceptable salts of the compounds or solvates thereof.

The symbols in Table 1 denote the following substituents.

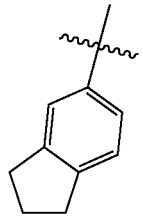
D1

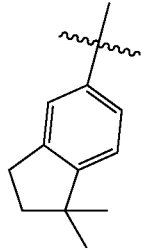
D2

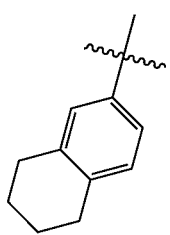
D3

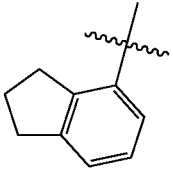
D4

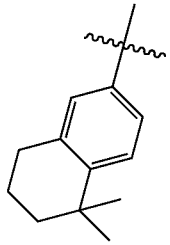
D5

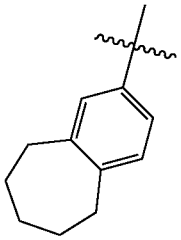
D6

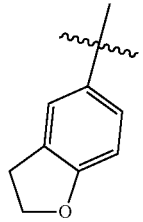
D7

D8 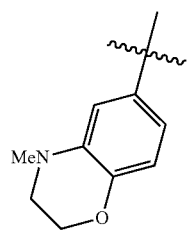
D9 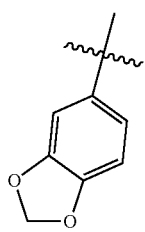
D10 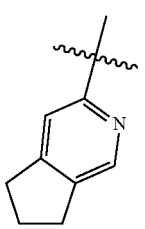
D11 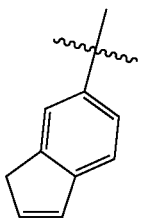
E1 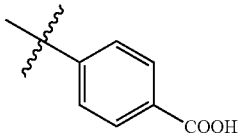
E2 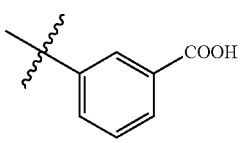
E3 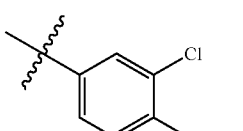
E4 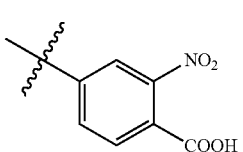
E5 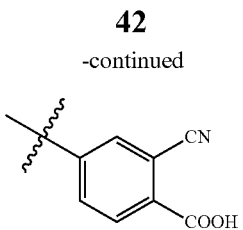
E6 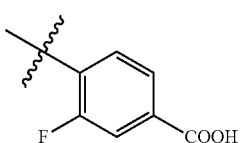
E7 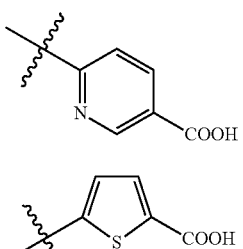
E8 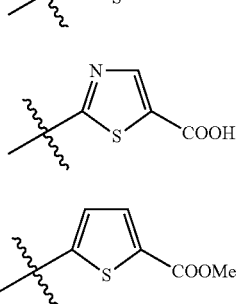
E9 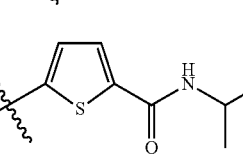
E10 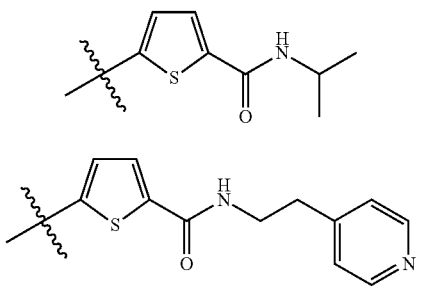
E11 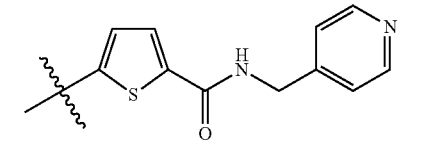
E12 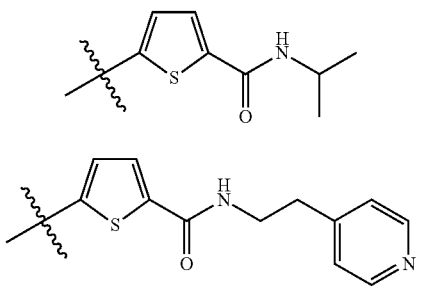
E13 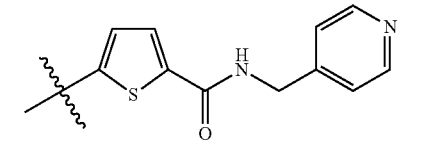
E14 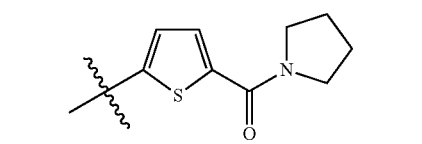
E15 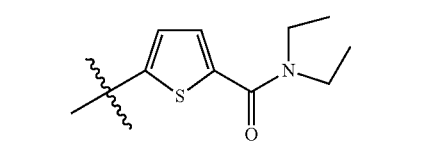

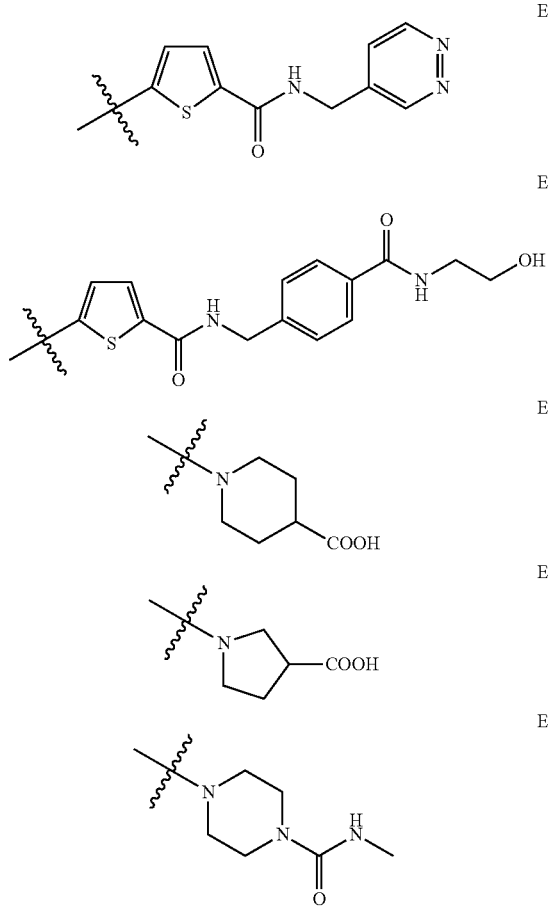

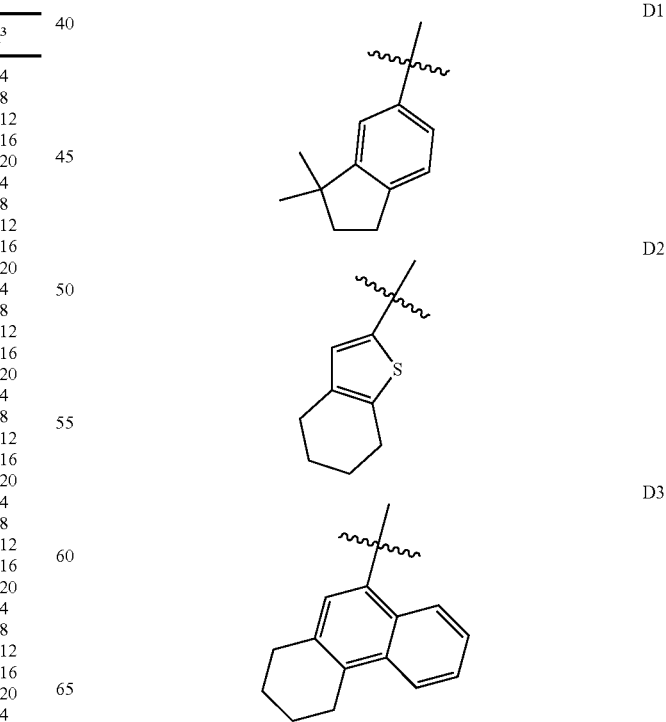

(34) Compounds represented by the formula (I) wherein $R^2$ is a methyl group, $L^1$, $L^2$ and $L^4$ are single bonds, $L^3$ is NH, X is OH, A is a nitrogen atom, B is NMe, Y is an oxygen atom, and $R^1$ and $R^3$ are any of the following combinations in Table 1 (provided that in the case of (34), D1 to D10 and E1 to E20 in the table denote the following substituents), tautomers, prodrugs or pharmaceutically acceptable salts of the compounds or solvates thereof.

TABLE 1

| $R^1$ | $R^3$ | $R^1$ | $R^3$ | $R^1$ | $R^3$ | $R^1$ | $R^3$ |
|---|---|---|---|---|---|---|---|
| D1 | E1 | D1 | E2 | D1 | E3 | D1 | E4 |
| D1 | E5 | D1 | E6 | D1 | E7 | D1 | E8 |
| D1 | E9 | D1 | E10 | D1 | E11 | D1 | E12 |
| D1 | E13 | D1 | E14 | D1 | E15 | D1 | E16 |
| D1 | E17 | D1 | E18 | D1 | E19 | D1 | E20 |
| D2 | E1 | D2 | E2 | D2 | E3 | D2 | E4 |
| D2 | E5 | D2 | E6 | D2 | E7 | D2 | E8 |
| D2 | E9 | D2 | E10 | D2 | E11 | D2 | E12 |
| D2 | E13 | D2 | E14 | D2 | E15 | D2 | E16 |
| D2 | E17 | D2 | E18 | D2 | E19 | D2 | E20 |
| D3 | E1 | D3 | E2 | D3 | E3 | D3 | E4 |
| D3 | E5 | D3 | E6 | D3 | E7 | D3 | E8 |
| D3 | E9 | D3 | E10 | D3 | E11 | D3 | E12 |
| D3 | E13 | D3 | E14 | D3 | E15 | D3 | E16 |
| D3 | E17 | D3 | E18 | D3 | E19 | D3 | E20 |
| D4 | E1 | D4 | E2 | D4 | E3 | D4 | E4 |
| D4 | E5 | D4 | E6 | D4 | E7 | D4 | E8 |
| D4 | E9 | D4 | E10 | D4 | E11 | D4 | E12 |
| D4 | E13 | D4 | E14 | D4 | E15 | D4 | E16 |
| D4 | E17 | D4 | E18 | D4 | E19 | D4 | E20 |
| D5 | E1 | D5 | E2 | D5 | E3 | D5 | E4 |
| D5 | E5 | D5 | E6 | D5 | E7 | D5 | E8 |
| D5 | E9 | D5 | E10 | D5 | E11 | D5 | E12 |
| D5 | E13 | D5 | E14 | D5 | E15 | D5 | E16 |
| D5 | E17 | D5 | E18 | D5 | E19 | D5 | E20 |
| D6 | E1 | D6 | E2 | D6 | E3 | D6 | E4 |
| D6 | E5 | D6 | E6 | D6 | E7 | D6 | E8 |
| D6 | E9 | D6 | E10 | D6 | E11 | D6 | E12 |
| D6 | E13 | D6 | E14 | D6 | E15 | D6 | E16 |
| D6 | E17 | D6 | E18 | D6 | E19 | D6 | E20 |
| D7 | E1 | D7 | E2 | D7 | E3 | D7 | E4 |
| D7 | E5 | D7 | E6 | D7 | E7 | D7 | E8 |
| D7 | E9 | D7 | E10 | D7 | E11 | D7 | E12 |
| D7 | E13 | D7 | E14 | D7 | E15 | D7 | E16 |
| D7 | E17 | D7 | E18 | D7 | E19 | D7 | E20 |
| D8 | E1 | D8 | E2 | D8 | E3 | D8 | E4 |
| D8 | E5 | D8 | E6 | D8 | E7 | D8 | E8 |
| D8 | E9 | D8 | E10 | D8 | E11 | D8 | E12 |
| D8 | E13 | D8 | E14 | D8 | E15 | D8 | E16 |
| D8 | E17 | D8 | E18 | D8 | E19 | D8 | E20 |
| D9 | E1 | D9 | E2 | D9 | E3 | D9 | E4 |
| D9 | E5 | D9 | E6 | D9 | E7 | D9 | E8 |
| D9 | E9 | D9 | E10 | D9 | E11 | D9 | E12 |
| D9 | E13 | D9 | E14 | D9 | E15 | D9 | E16 |
| D9 | E17 | D9 | E18 | D9 | E19 | D9 | E20 |
| D10 | E1 | D10 | E2 | D10 | E3 | D10 | E4 |
| D10 | E5 | D10 | E6 | D10 | E7 | D10 | E8 |
| D10 | E9 | D10 | E10 | D10 | E11 | D10 | E12 |
| D10 | E13 | D10 | E14 | D10 | E15 | D10 | E16 |
| D10 | E17 | D10 | E18 | D10 | E19 | D10 | E20 |
| D11 | E1 | D11 | E2 | D11 | E3 | D11 | E4 |
| D11 | E5 | D11 | E6 | D11 | E7 | D11 | E8 |
| D11 | E9 | D11 | E10 | D11 | E11 | D11 | E12 |
| D11 | E13 | D11 | E14 | D11 | E15 | D11 | E16 |
| D11 | E17 | D11 | E18 | D11 | E19 | D11 | E20 |

-continued
D4 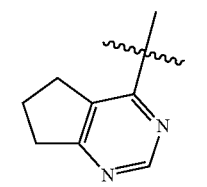
D5 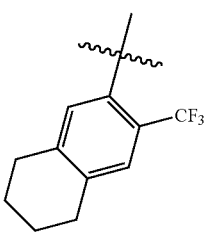
D6 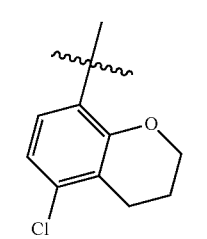
D7 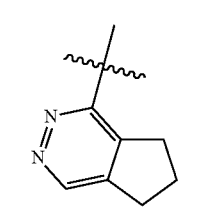
D8 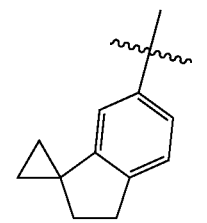
D9 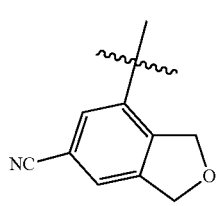
D10 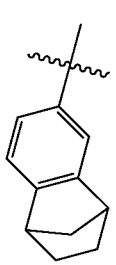
-continued
E1 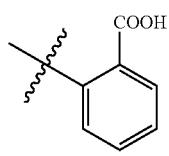
E2 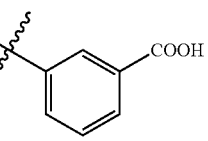
E3 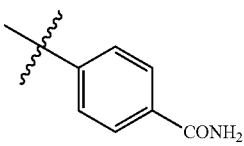
E4 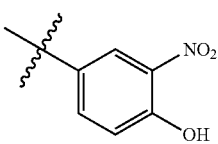
E5 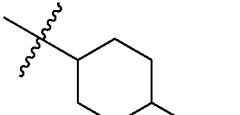
E6 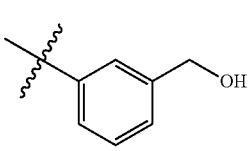
E7 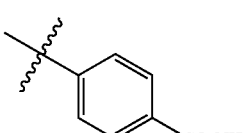
E8 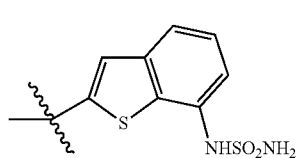
E9 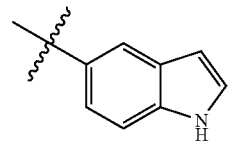
E10 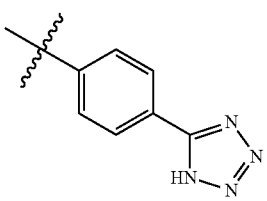

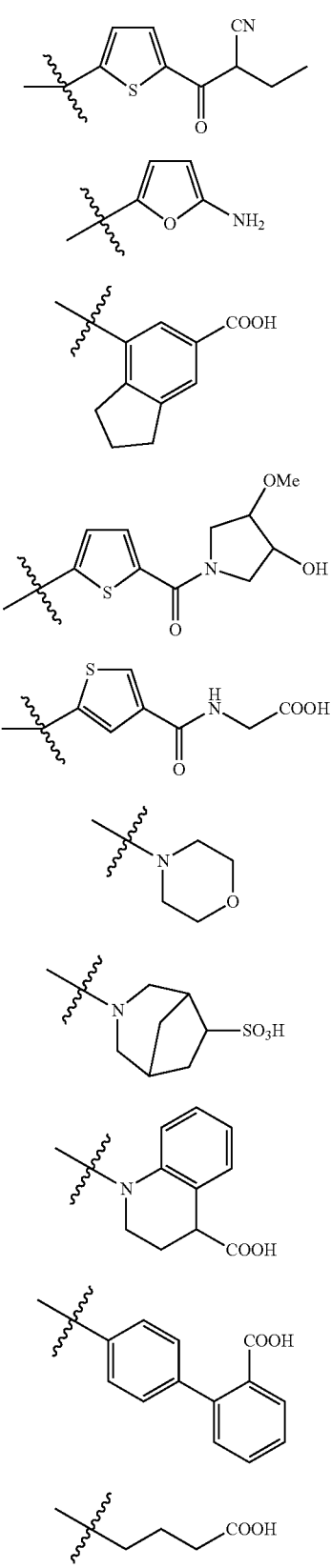

(35) The compounds with the combination of substituents as defined in (33) or (34), wherein $L^4$ is converted to NH, tautomers, prodrugs or pharmaceutically acceptable salts of the compounds or solvates thereof.

(36) The compounds with the combination of substituents as defined in (33) or (34), wherein $L^4$ is converted to NMe, tautomers, prodrugs or pharmaceutically acceptable salts of the compounds or solvates thereof.

(37) The compounds with the combinations of substituents as defined in (33) to (36), wherein Y is converted to a sulfur atom, tautomers, prodrugs or pharmaceutically acceptable salts of the compounds or solvates thereof.

(38) The compounds with the combinations of substituents as defined in (33) to (36), wherein Y is converted to N—CN, tautomers, prodrugs or pharmaceutically acceptable salts of the compounds or solvates thereof.

(39) The compounds with the combinations of substituents as defined in (33) to (36), wherein $R^2$ is converted to $CF_3$, tautomers, prodrugs or pharmaceutically acceptable salts of the compounds or solvates thereof.

(40) The compounds with the combinations of substituents as defined in (33) to (38), wherein $R^2$ is converted to a hydrogen atom, tautomers, prodrugs or pharmaceutically acceptable salts of the compounds or solvates thereof.

(41) The compounds with the combinations of substituents as defined in (33) to (38), wherein $R^2$ is converted to a c-propyl group, tautomers, prodrugs or pharmaceutically acceptable salts of the compounds or solvates thereof.

(42) The compounds with the combinations of substituents as defined in (33) to (41), wherein X is converted to $NH_2$, tautomers, prodrugs or pharmaceutically acceptable salts of the compounds or solvates thereof.

(43) The compounds with the combinations of substituents as defined in (33) to (41), wherein X is converted to SH, tautomers, prodrugs or pharmaceutically acceptable salts of the compounds or solvates thereof.

(44) The compounds with the combinations of substituents as defined in (33) to (43), wherein $L^3$ is converted to NMe, tautomers, prodrugs or pharmaceutically acceptable salts of the compounds or solvates thereof.

(45) The compounds with the combinations of substituents as defined in (33) to (44), wherein $L^1$ is converted to an ethenylene group, tautomers, prodrugs or pharmaceutically acceptable salts of the compounds or solvates thereof.

(46) The compounds with the combinations of substituents as defined in (33) to (45), wherein $L^2$ is converted to an oxygen atom, tautomers, prodrugs or pharmaceutically acceptable salts of the compounds or solvates thereof.

(47) The compounds with the combinations of substituents as defined in (33) to (46), wherein A is converted to a nitrogen atom, and B is converted to $NCF_3$, tautomers, prodrugs or pharmaceutically acceptable salts of the compounds or solvates thereof.

(48) The compounds with the combinations of substituents as defined in (33) to (46), wherein A is converted to a nitrogen atom, and B is converted to a sulfur atom, tautomers, prodrugs or pharmaceutically acceptable salts of the compounds or solvates thereof.

(49) The compounds with the combinations of substituents as defined in (33) to (46), wherein A is converted to a nitrogen atom, and B is converted to an oxygen atom, tautomers, prodrugs or pharmaceutically acceptable salts of the compounds or solvates thereof.

(50) The compounds with the combinations of substituents as defined in (33) to (46), wherein A is converted to CH, and B is converted to an oxygen atom, tautomers, prodrugs or pharmaceutically acceptable salts of the compounds or solvates thereof.

(51) The compounds with the combinations of substituents as defined in (33) to (46), wherein A is converted to CH, and B is converted to a sulfur atom, tautomers, prodrugs or pharmaceutically acceptable salts of the compounds or solvates thereof.

(52) The compounds with the combinations of substituents as defined in (33) to (46), wherein A is converted to CH, and B is converted to NMe, tautomers, prodrugs or pharmaceutically acceptable salts of the compounds or solvates thereof.

(53) The compounds with the combinations of substituents as defined in (50) to (52), wherein A is converted to CMe, tautomers, prodrugs or pharmaceutically acceptable salts of the compounds or solvates thereof.

(54) The compounds with the combinations of substituents as defined in (50) to (52), wherein A is converted to CCl, tautomers, prodrugs or pharmaceutically acceptable salts of the compounds or solvates thereof.

(55) Thrombopoietin receptor activators containing the compounds according to (1) to (54), tautomers, prodrugs or pharmaceutically acceptable salts of the compounds or solvates thereof, as an active ingredient.

(56) Preventive, therapeutic and improving agents for diseases against which activation of the thrombopoietin receptor is effective, which contain the thrombopoietin receptor activators according to (55), as an active ingredient.

(57) Platelet increasing agents containing the thrombopoietin receptor activators according to (55), as an active ingredient.

In the present invention, the compounds of the present invention represented by the formula (I) may be present in the form of tautomers or geometrical isomers which undergo endocyclic or exocyclic isomerization, mixtures of tautomers or geometric isomers or mixtures of thereof. When the compounds of the present invention have an asymmetric center, whether or not resulting from an isomerization, the compounds of the present invention may be in the form of resolved optical isomers or in the form of mixtures containing them in certain ratios. Further, when the compounds of the present invention have two or more asymmetric centers, the compounds of the present invention can be in the form of diastereomers dues to optical isomerism about them.

The compounds of the present invention may be in the form of a mixture of all these isomers in certain ratios. For example, diastereomer can be separated by techniques known well to those skilled in the art such as fractional crystallization, and optical isomers can be obtained by techniques well known in the field of organic chemistry for this purpose.

The compounds of the present invention represented by the formula (I) or pharmaceutically acceptable salts thereof may be in the form of arbitrary crystals or arbitrary hydrates, depending on the production conditions. The present invention covers these crystals, hydrates and mixtures. They may be in the form of solvates with organic solvents such as acetone, ethanol and tetrahydrofuran, and the present invention covers any of these forms.

The compounds of the present invention represented by the formula (I) may be converted to pharmaceutically acceptable salts or may be liberated from the resulting salts, if necessary. The pharmaceutically acceptable salts of the present invention may be, for example, salts with alkali metals (such as lithium, sodium and potassium), alkaline earth metals (such as magnesium and calcium), ammonium, organic bases and amino acids. They may be salts with inorganic acids (such as hydrochloric acid, hydrobromic acid, phosphoric acid and sulfuric acid) and organic acids (such as acetic acid, citric acid, maleic acid, fumaric acid, tartaric acid, benzenesulfonic acid, methanesulfonic acid and p-toluenesulfonic acid).

The compounds which serve as prodrugs are derivatives of the present invention having chemically or metabolically degradable groups which give pharmacologically active compounds of the present invention upon solvolysis or under physiological conditions in vivo. Methods for selecting or producing appropriate prodrugs are disclosed, for example, in Design of Prodrugs (Elsevier, Amsterdam 1985).

In the present invention, when the compound has a hydroxy group, acyloxy derivatives obtained by reacting the compound with appropriate acyl halides or appropriate acid anhydrides may, for example, be mentioned as prodrugs. Acyloxys particularly preferred as prodrugs include —$OCOC_2H_5$, —OCO(t-Bu), —$OCOC_{15}H_{31}$, —$OCO(m-CO_2Na-Ph)$, —$OCOCH_2CH_2CO_2Na$, —$OCOCH(NH_2)CH_3$, —$OCOCH_2N(CH_3)_2$ and the like.

When the compound of the present invention has an amino group, amide derivatives obtained by reacting the compound having an amino group with appropriate acid halides or appropriate mixed acid anhydrides may, for example, be mentioned as prodrugs. Amides particularly preferred as prodrugs include —$NHCO(CH_2)_{20}OCH_3$, —$NHCOCH(NH_2)CH_3$ and the like.

The preventive, therapeutic and improving agents for diseases against which activation of the thrombopoietin receptor is effective which contain the thrombopoietin receptor activators of the present invention, as an active ingredient may usually be administered as oral medicines such as tablets, capsules, powder, granules, pills and syrup, as rectal medicines, percutaneous medicines or injections. The agents of the present invention may be administered as a single therapeutic agent or as a mixture with other therapeutic agents. Though they may be administered as they are, they are usually administered in the form of medical compositions. These pharmaceutical preparations can be obtained by adding pharmacologically and pharmaceutically acceptable additives by conventional methods. Namely, for oral medicines, ordinary additives such as excipients, lubricants, binders, disintegrants, humectants, plasticizers and coating agents may be used. Oral liquid preparations may be in the form of aqueous or oily suspensions, solutions, emulsions, syrups or elixirs or may be supplied as dry syrups to be mixed with water or other appropriate solvents before use. Such liquid preparations may contain ordinary additives such as suspending agents, perfumes, diluents and emulsifiers. In the case of rectal administration, they may be administered as suppositories. Suppositories may use an appropriate substance such as cacao butter, laurin tallow, Macrogol, glycerogelatin, Witepsol, sodium stearate and mixtures thereof as the base and may, if necessary, contain an emulsifier, a suspending agent, a preservative and the like. For injections, pharmaceutical ingredients such as distilled water for injection, physiological saline, 5% glucose solution, propylene glycol and other solvents or solubilizing agents, a pH regulator, an isotonizing agent and a stabilizer may be used to form aqueous dosage forms or dosage forms which need dissolution before use.

The dose of the agents of the present invention for administration to human is usually about from 0.1 to 1000 mg/human/day in the case of oral drugs or rectal administration and about from 0.05 mg to 500 mg/human/day in the case of injections, though it depends on the age and conditions of the patient. The above-mentioned ranges are mere examples, and the dose should be determined from the conditions of the patient.

The present invention is used when the use of compounds which have thrombopoietin receptor affinity and act as thrombopoietin receptor agonists are expected to improve pathological conditions. For example, hematological disorders accompanied by abnormal platelet count may be mentioned. Specifically, it is effective for therapy or prevention of human and mammalian diseases caused by abnormal megakaryopoiesis, especially those accompanied by thrombocytopenia. Examples of such diseases include thrombocytopenia accompanying chemotherapy or radiotherapy of cancer, thrombocytopenia accompanying antiviral therapy for diseases such as hepatitis C, thrombocytopenia caused by bone marrow transplantation, surgery and serious infections, or gastrointestinal bleeding, but such diseases are not restricted to those mentioned. Typical thrombocytopenias such as aplastic anemia, idiopathic thrombocytopenic purpura, myelodysplastic syndrome, hepatic disease, HIV infection and thrombopoietin deficiency are also targets of the agents of the present invention. The present invention may be used as a peripheral stem cell mobilizer, a megakaryoblastic or megakaryocytic leukemia cell differentiation inducer and a platelet increasing agent for platelet donors. In addition, potential applications include therapeutic angiogenesis based on differentiation and proliferation of vascular endothelial cells and endothelial progenitor cells, prevention and therapy of arteriosclerosis, myocardial infarction, unstable angina, peripheral artery occlusive disease, but there is no restriction.

The compounds of the present invention can be synthesized by the processes mentioned later, but the production of the compounds of the present invention is not restricted to these general examples.

The compounds of the present invention can usually be purified by column chromatography, thin layer chromatography, high performance liquid chromatography (HPLC) or high performance liquid chromatography-mass spectrometry (LC-MS) and, if necessary, they may be obtained with high purity by recrystallization or washing with solvents.

As bases commonly used in the production of the compounds of the present invention, alkali metal salts such as sodium carbonate, potassium carbonate, cesium carbonate, sodium hydrogen carbonate, potassium hydrogen carbonate, potassium hydroxide, sodium hydroxide, sodium hydride, lithium hydride, sodium amide, t-butoxypotassium, t-butoxysodium, n-butyllithium, lithium diisopropylamide and amines such as pyridine, triethylamine, N,N-diisopropylethylamine, pyrrolidine and N-methylpiperidine, silane reagents such as hexamethyldisilazane, sodium acetate and potassium acetate may be mentioned.

In general, in the production of the compounds of the present invention, any solvents that are stable and inert under the reaction conditions and do not hinder the reactions may be used without any particular restrictions, and sulfoxide solvents represented by dimethyl sulfoxide, amide solvents represented by dimethylformamide or dimethylacetamide, ether solvents represented by diethyl ether, dimethoxyethane, tetrahydrofuran, 1,4-dioxane or cyclopenthyl methyl ether, halogenated solvents represented by dichloromethane, chloroform or 1,2-dichloroethane, nitrile solvents represented by acetonitrile or propionitrile, aromatic hydrocarbon solvents represented by benzene or toluene, hydrocarbon solvents represented by hexane or heptane, ester solvents represented by ethyl acetate, alcohol solvents represented by methanol, ethanol, 1-propanol, 2-propanol or ethylene glycol and water may be mentioned. The reactions may be carried out in an arbitrary mixture of solvents mentioned above or in the absence of a solvent.

In general, in the production of the compounds of the present invention, the reaction temperature is chosen appropriately within the range of from −78° C. to the boiling point of the solvent used for the reaction, and the production of the compounds of the present invention may be carried out at ordinary pressure or under pressure or with microwave irradiation.

General processes for production of the compounds of the present invention are shown below, and the formulae of the intermediate and the end product in each step therein cover their precursors, too. Herein, precursors are defined as compounds which can be converted to the desired product, if necessary, through hydrolysis, deprotection, reduction, oxidation, alkylation or the like and include compounds protected with chemically acceptable protective groups. Protection and deprotection may be carried out by generally known protection and deprotection reactions (Protective Groups in Organic Synthesis, Fourth edition, T. W. Greene, John Wiley & Sons Inc. (2006)).

Compounds having a tetrazolyl group as intermediates of the present invention may be synthesized by generally known reactions (Synthesis, (6), 910-914, 1998).

Among the compounds represented by the formula (I), the compounds having $NR^8$ as $L^3$ or its precursor can be obtained from the following intermediate (1) or (2) by a reaction with the intermediate (3) or (4) by referring to WO2004108683, WO2006062240 or WO2007010954.

Hereinafter, an intermediate represented by the formula (1) is referred to as an intermediate (1). The same applies to other intermediates.

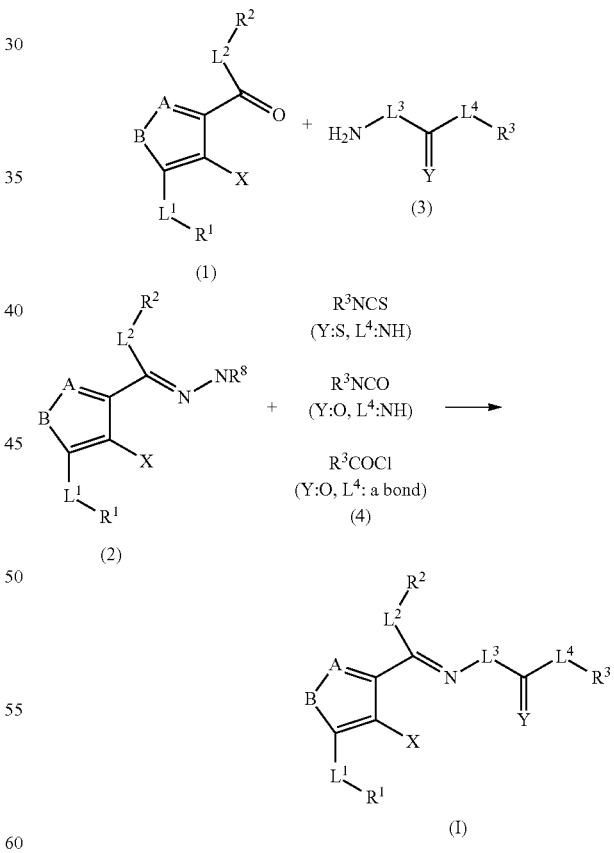

intermediates (1), (2), (3) and (4) can be obtained as commercial reagents or by referring to the WO2004108683, WO2006062240, WO2007010954 or WO2009107799.

Among intermediates (1), those having a single bond as $L^1$ or their precursors can be obtained by reacting a compound (5) with an organic metal compound represented by the formula (6) such as an organic boronic acid, an organic boronate, an organic tin compound or an organic magnesium compound in a solvent with heating, if necessary in the presence of a transition metal catalyst such as tetrakistriphenylphosphinopalladium or (1,1'-bis(diphenylphosphino)ferrocene)dichloropalladium and/or a base such as potassium carbonate, triethylamine or sodium carbonate, if necessary with heating and stirring (for example, by referring to Sen-i Kinzoku ga Maneku Yuki Gosei, Jiro Tsuji, 1997, KAGAKUDOJIN, and Cross-Coupling Reactions, A Practical Guide, Series: Topics in Current Chemistry, Vol. 219. Miyaura Norio, Springer).

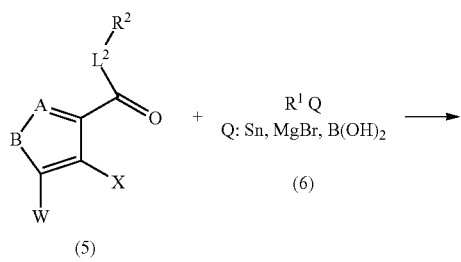

W: Halogen atom, OTf

Intermediates (1) can also be obtained by referring to J. Chem. Soc., Chem. Commun., 22, 1643 (1992). For example, intermediates (1) wherein A is a carbon atom, B is a sulfur atom, X is a hydroxy group, and $L^1$ and $L^2$ are single bonds, which are referred to as intermediates (14), can be synthesized as shown below through intermediates (7), (8), (9), (10), (11), (12) and (13). For example, it is possible to convert a 2-thioacetate intermediate (7) as the starting material to an intermediate (8) in a solvent by using acrylonitrile and a base such as sodium methoxide, if necessary with heating and stirring, then convert the intermediate (8) to an intermediate (9) by using an alkylating agent such as dimethyl sulfate or an alkyl halide and, if necessary, a base, if necessary with heating and stirring, and convert the intermediate (9) to an intermediate (10) by using an oxidizing agent such as sulfuryl chloride or hydrogen peroxide, if necessary with heating and stirring. It is possible to further convert the intermediate (10) to an intermediate (11) by using a halogenating agent such as bromine or iodine, if necessary with heating and stirring, and convert the intermediate (11) to an intermediate (12) in a solvent by using an organic metal compound such as an organic boronic acid, an organic boronate, an organic tin compound or an organic magnesium compound, if necessary in the presence of a transition metal catalyst such as tetrakistriphenylphosphinopalladium or (1,1'-bis(diphenylphosphino)ferrocene)dichloropalladium and/or a base such as potassium carbonate, triethylamine or sodium carbonate, if necessary with heating and stirring. It is possible to further convert the intermediate (12) to an intermediate (13) by using an alkylating agent such as an organic magnesium compound, an organic lithium compound or an organic aluminum compound, if necessary with heating and stirring, and then convert the intermediate (13) to an intermediate (14) by using an dealkylating agent such as boron tribromide.

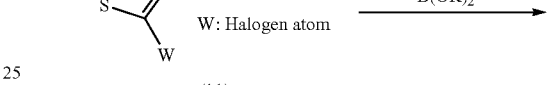

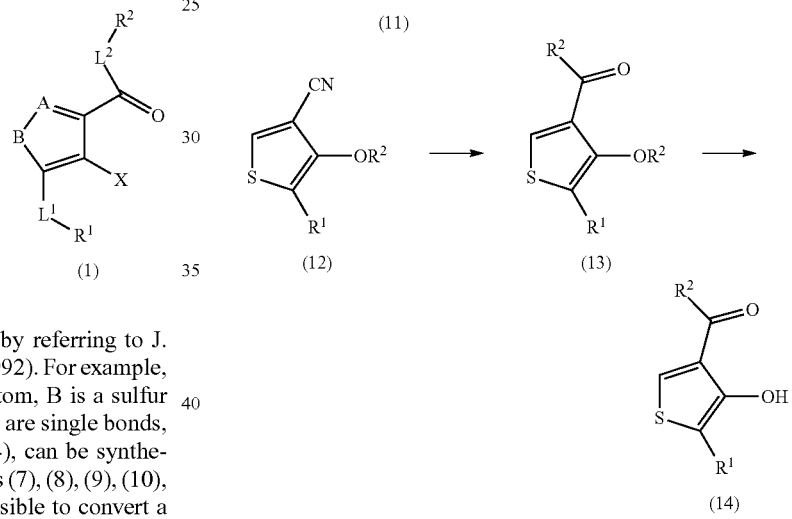

Intermediates (1) and (2) wherein A is $CR^4$, B is a sulfur atom, and $L^1$ and $L^2$ are single bonds can be synthesized by referring to WO2004108683, WO2006062240 or WO2007010954.

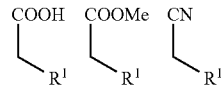

(wherein $R^1$ is a $C_{2-14}$ aryl group fused to a $C_{2-9}$ heterocyclyl group or a $C_{2-14}$ aryl group fused to a $C_{3-10}$ cycloalkyl group (the $C_{2-14}$ aryl group fused to a $C_{2-9}$ heterocyclyl group and the $C_{2-14}$ aryl group fused to a $C_{3-10}$ cycloalkyl group are unsubstituted or substituted with one or more identical or different substituents selected from the substituent set $V^1$)).

Intermediates (1) and (2) wherein A is a nitrogen atom, B is $NR^5$, and $L^1$ and $L^2$ are single bonds can be synthesized from the following compounds by referring to WO2004108683 or WO2006062240.

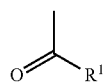

(wherein $R^1$ is a $C_{2-14}$ aryl group fused to a $C_{2-9}$ heterocyclyl group or a $C_{2-14}$ aryl group fused to a $C_{3-10}$ cycloalkyl group (the $C_{2-14}$ aryl group fused to a $C_{2-9}$ heterocyclyl group and the $C_{2-14}$ aryl group fused to a $C_{3-10}$ cycloalkyl group are unsubstituted or substituted with one or more identical or different substituents selected from the substituent set $V^1$)).

EXAMPLES

Now, the present invention will be described in further detail with reference to Reference Synthetic Examples, Synthetic Examples, Assay Examples and Formulation Examples. However, it should be understood that the present invention is by no means restricted by these specific Examples. In the Examples, NMR denotes nuclear magnetic resonance, LC/MS denotes liquid chromatography mass spectrometry, v/v means volume ratio, Ref. Ex. denotes Reference Synthetic Example, Ex. denotes Synthetic Example, and the figures following Ref. Ex. or Ex. means a Reference Synthetic Example or Synthetic Example number.

The $^1$H-NMR analysis was carried out at 300 MHz or 700 MHz, and LC/MS was measured under the following conditions.

The compositions of the eluents used in silica gel column chromatography for purification were expressed by volume ratio.

LC/MS condition 1
Column: Waters SunFire C18 (3.5 μm, 2.1×20 mm)
Eluent: acetonitrile/0.1% aqueous formic acid (10/90→85/15, v/v)

Reference Synthetic Example 1

1-[5-(2,3-Dihydro-1H-inden-5-yl)-4-hydroxy-1-methyl-1H-pyrazol-3-yl]ethanone

Synthesis was carried out in accordance with WO2004108683 by using 1-(2,3-dihydro-1H-inden-5-yl) ethanone.
Morphology: yellow solid
LC/MS: condition 1 Retention time 4.25 (min)
LC/MS (ESI$^+$) m/z; 257 [M+1]$^+$
$^1$H-NMR (CDCl$_3$) δ: 2.12 (quint, J=7.5 Hz, 2H), 2.58 (s, 3H), 2.91-3.00 (m, 4H), 3.88 (s, 3H), 7.19 (d, J=7.8 Hz, 1H), 7.29 (s, 1H), 7.32 (d, J=7.8 Hz, 1H), 8.11 (s, 1H).

Reference Synthetic Example 2

5-(2,3-Dihydro-1H-indene-5-yl)-3-(1-hydrazonoethyl)-1-methyl-1H-pyrazol-4-ol

Synthesis was carried out in accordance with WO2006062240 by using 1-[5-(2,3-dihydro-1H-inden-5-yl)-4-hydroxy-1-methyl-1H-pyrazol-3-yl]ethanone.
Morphology: pale yellow oil
LC/MS: condition 1 Retention time 3.94 (min)
LC/MS (ESI$^+$) m/z; 271 [M+1]$^+$
$^1$H-NMR (CDCl$_3$) δ: 2.11 (quint, J=7.5 Hz, 2H), 2.23 (s, 3H), 2.94 (q, J=7.5 Hz, 4H), 3.81 (s, 3H), 5.20 (s, 2H), 7.22 (d, J=7.2 Hz, 1H), 7.29-7.34 (m, 2H), 8.81 (s, 1H).

Reference Synthetic Example 3

1-[4-Hydroxy-5-(5,6,7,8-tetrahydronaphthalen-2-yl)thiophen-3-yl]ethanone

Synthesis was carried out by the following synthesis methods 1 and 2.
Synthesis Method 1
Synthesis was carried out in accordance with WO2009107799 by using 2-(5,6,7,8-tetrahydronaphthalen-2-yl)acetic acid.
Morphology: pale yellow solid
LC/MS: condition 1 Retention time 4.97 (min)
LC/MS (ESI$^+$) m/z; 273 [M+1]$^+$
LC/MS (ESI$^-$) m/z; 271 [M−1]$^-$
$^1$H-NMR (CDCl$_3$) δ: 1.79-1.83 (m, 4H), 2.56 (s, 3H), 2.77-2.81 (m, 4H), 7.09 (d, J=7.9 Hz, 1H), 7.47-7.51 (m, 2H), 7.85 (s, 1H), 10.26 (s, 1H).
Synthesis Method 2

(1) Synthesis of
7-bromo-3,4-dihydronaphthalen-1(2H)-one

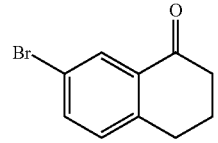 [SMILES: O=C1CCCc2ccc(Br)cc21]

10.1 g of 4-(4-bromophenyl)butanoic acid was added in portions to 100 g of polyphosphoric acid heated to 90° C. with stirring. After 1 hour of reaction, the reaction mixture was poured into 300 ml of ice-cold water with stirring, and the precipitated yellow solid was collected by filtration, washed with water and dissolved in a solvent mixture of 300 ml of ether and 100 ml of water. The ether layer was collected, and the aqueous layer was extracted with 75 ml of ether, and the extract was combined with the ether layer, washed with 30 ml of saturated aqueous sodium carbonate twice and with 50 ml of water twice, dried over anhydrous magnesium sulfate and concentrated under reduced pressure. The resulting residue was recrystallized from hexane to obtain 7.9 g of the desired product (yield 84%).
Morphology: light brown crystals (2) Synthesis of
6-bromo-1,2,3,4-tetrahydronaphthalene

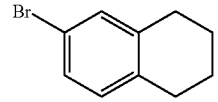 [SMILES: Brc1ccc2c(c1)CCCC2]

To 7.50 g of 7-bromo-3,4-dihydronaphthalen-1(2H)-one in trifluoroacetic acid (60 ml), 15.5 g of triethylsilane was added dropwise over 30 minutes at room temperature (the temperature of the reaction solution exothermically elevated from 27° C. to 50° C.). After the dropwise addition, the reaction solution was allowed to react at room temperature for 2 hours and then on a water bath at 50° C. for 1.5 hours. The reaction mixture was concentrated under reduced pressure, and the residue was poured into 400 ml of saturated aqueous sodium hydrogen carbonate, extracted with ethyl acetate (200 ml×1, 100 ml×1). The organic layer was washed with saturated aqueous sodium chloride, dried over anhydrous magnesium sulfate and concentrated under reduced pressure. The residue was purified by silica gel column chromatography (eluent: hexane) to obtain 6.63 g of the desired product (yield 94%).

Morphology: pale yellow oil (3) Synthesis of 5,6,7,8-tetrahydronaphthalen-2-yl boronic acid

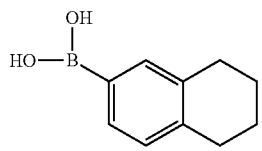 [SMILES: OB(O)c1ccc2c(c1)CCCC2]

To 6.60 g of 6-bromo-1,2,3,4-tetrahydronaphthalene in THF (60 ml) cooled on a dry ice-acetone bath, 25 ml of n-butyllithium (1.60 M/hexane solution) was added dropwise over 30 minutes in an argon stream, and after the dropwise addition, the reaction mixture was stirred for 1 hour under the same conditions. Then, 6.47 g of triisopropyl borate was added dropwise over 20 minutes, and after the dropwise addition, the reaction mixture was allowed to react for 3.5 hours. The reaction mixture was poured into ice-cold water and brought to almost neutral (pH 8) with ammonium chloride and then extracted with ethyl acetate (400 ml×1, 100 ml×2), and the organic layer was washed with saturated aqueous sodium chloride, dried over anhydrous magnesium sulfate and concentrated under reduced pressure. The resulting residue was purified by silica gel column chromatography (eluent: methanol/chloroform=1/30), and the resulting solid was washed with a small amount of cold hexane to obtain 5.11 g of the desired product (yield 93%).

Morphology: white crystals (4) Synthesis of 4-methoxy-5-(5,6,7,8-tetrahydronaphthalen-2-yl)thiophene-3-carbonitrile

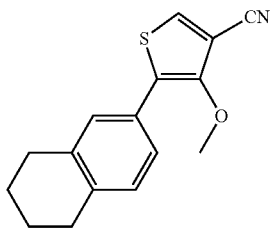 [SMILES: COc1c(C#N)csc1-c1ccc2c(c1)CCCC2]

3.53 g of 5-bromo-4-metoxythiophene-3-carbonitrile synthesized in accordance with WO2006062247, 3.13 g of 5,6,7,8-tetrahydronaphthalen-2-yl boronic acid synthesized above in (3), 0.21 g of palladium acetate, 6.70 g of anhydrous potassium carbonate and 5.10 g of tetrabutylammonium bromide were mixed with 30 ml of 1,2-dimethoxyethane and 30 ml of water and allowed to react at room temperature for 19 hours with stirring. After addition of 200 ml of ethyl acetate and 150 ml of saturated aqueous sodium chloride, the reaction mixture was stirred at room temperature for 1 hour. The precipitated black solid was removed by suction filtration (through Celite). The filtrate was allowed to separate, and the ethyl acetate layer was withdrawn, washed with saturated aqueous sodium chloride, dried over anhydrous sodium sulfate and concentrated under reduced pressure. The resulting residue was purified by silica gel column chromatography (eluent: ethyl acetate/hexane=1/15) to obtain 3.56 g of the desired product (yield 82%).

Morphology: orange yellow oil $^1$H-NMR (CDCl$_3$) δ: 3.26 (t, J=8.7 Hz, 2H), 3.90 (s, 3H), 4.63 (t, J=8.7 Hz, 2H), 6.82 (d, J=8.1 Hz, 1H), 7.39 (d, J=8.1 Hz, 1H), 7.48 (br.s, 1H), 7.66 (s, 1H).

(5) Synthesis of 1-[4-methoxy-5-(5,6,7,8-tetrahydronaphthalen-2-yl)thiophen-3-yl]ethanone

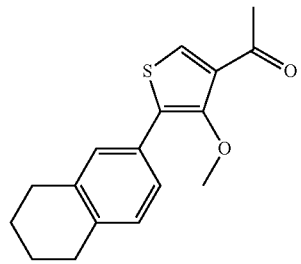 [SMILES: COc1c(C(C)=O)csc1-c1ccc2c(c1)CCCC2]

To 3.51 g of 4-methoxy-5-(5,6,7,8-tetrahydronaphthalen-2-yl)thiophene-3-carbonitrile in diethyl ether (45 ml) cooled with water, 43.3 ml of methylmagnesium bromide (3.0 M diethyl ether solution) was added dropwise at room temperature over 5 minutes (exothemically). The reaction mixture was allowed to react at room temperature for 3 days and poured into 30 ml of concentrated hydrochloric acid diluted with 300 ml of ice-cold water and stirred at room temperature for 1 hour then on a water bath at 35° C. for 1 hour. After addition of 200 ml of ethyl acetate, the reaction mixture was allowed to separate, and the organic layer was collected. The aqueous layer was extracted with 100 ml of ethyl acetate three times, and the extracts were combined with the organic layer. The organic layer was washed with saturated aqueous sodium chloride, dried over anhydrous sodium sulfate and concentrated under reduced pressure. The resulting residue (dark brown oil) was purified by silica gel column chromatography (eluent: ethyl acetate/hexane=1/20→1/15) to obtain 2.44 g of the desired product (yield 65%).

Morphology: light brown oil $^1$H-NMR (CDCl$_3$) δ: 2.56 (s, 3H), 3.27 (t, J=8.7 Hz, 2H), 3.69 (s, 3H), 4.63 (t, J=8.7 Hz, 2H), 6.83 (d, J=8.4 Hz, 1H), 7.44 (d, J=8.4 Hz, 1H), 7.53 (br.s, 1H), 7.83 (s, 1H).

(6) Synthesis of 1-[4-hydroxy-5-(5,6,7,8-tetrahydronaphthalen-2-yl)thiophen-3-yl]ethanone To 2.4 g of 1-[4-methoxy-5-(5,6,7,8-tetrahydronaphthalen-2-yl)thiophen-3-yl]ethanone in chloroform (25 ml) cooled with ice, 9.4 ml of boron tribromide (1.0 M dichloromethane solution) was added dropwise, and then the reaction mixture was allowed to react for 1.5 hours. The reaction mixture was poured into 300 ml of ice-cold water and extracted with 250 ml of chloroform. The aqueous layer was extracted with 100 ml of chloroform once, and the extract was combined with the previously chloroform extract, washed with 150 ml of saturated aqueous sodium chloride twice, dried over anhydrous sodium sulfate and concentrated under reduced pressure. The resulting residue (dark brown oil) was purified by silica gel column chromatography (eluent: ethyl acetate/hexane=1/20), and the resulting solid was washed with hexane to obtain 1.05 g of the desired product (yield 45%).

Morphology: orange yellow crystals $^1$H-NMR (CDCl$_3$) δ: 2.56 (s, 3H), 3.26 (t, J=8.7 Hz, 2H), 4.60 (t, J=8.7 Hz, 2H), 6.81 (d, J=8.7 Hz, 1H), 7.48 (d, J=8.7 Hz, 1H), 7.67 (br.s, 1H), 7.82 (s, 1H), 10.22 (s, 1H).

Reference Synthetic Example 4

4-(1-Hydrazonoethyl)-2-(5,6,7,8-tetrahydronaphthalen-yl)thiophen-3-ol

Synthesis was carried out in the same manner as in Reference Synthetic Example 2 by using 1-[4-hydroxy-5-(5,6,7,8-tetrahydronaphthalen-2-yl)thiophen-3-yl]ethanone Morphology: pale yellow amorphous
LC/MS: condition 1 Retention time 4.80 (min)
LC/MS (ESI$^+$) m/z; 287 [M+1]$^+$ Reference Synthetic Example 5

1-[5-(2,3-Dihydro-1H-inden-5-yl)-4-hydroxythiophen-3-yl]ethanone (1) Synthesis of (2,3-dihydro-1H-inden-5-yl)boronic acid

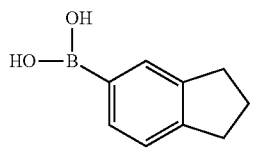

Synthesis was carried out by the following synthesis methods 3 and 4.

Synthesis Method 3

5.91 g (0.05 mol) of 2,3-dihydro-1H-indene was stirred with 60 ml of acetic acid at room temperature, and to the resulting solution, 12.3 g (0.055 mol) of zinc (II) bromide was added and then 19.5 g (0.05 mol) of benzyltrimethylammonium tribromide was added. After the addition, the reaction solution was stirred at room temperature for 4 hours to complete the reaction. After completion of the reaction, the reaction solution was extracted by adding ethyl acetate and saturated aqueous sodium chloride. The ethyl acetate layer was neutralized and washed with saturated aqueous sodium hydrogen carbonate, dried over anhydrous magnesium sulfate and concentrated under reduced pressure. The residue was purified by silica gel column chromatography (eluent: n-hexane) to isolate 5.11 g of an oil (yield: 51.9%). The oil turned out to be a mixture of about 70 to 80% of the 5-bromide and about 30 to 20% of the 4-bromide upon 1H-NMR analysis. 8.3 g (0.0421 mol) of 5-bromo-2,3-dihydro-1H-indene and 4-bromo-2,3-dihydro-1H-indene was stirred with 40 ml of dry tetrahydrofuran with cooling to −78° C., and 32.0 ml of 1.6 M n-butyllithium in n-hexane was added dropwise. After the dropwise addition, the reaction solution was stirred at −78° C. for 15 minutes, and 8.75 g (0.0842 mol) of trimethyl borate was added. After the dropwise addition, the reaction solution was stirred for 3 hours while the temperature was allowed to elevate to −20° C. Then, 50 ml of 1 M hydrochloric acid was added dropwise, and the reaction solution was stirred for 2 hours while the temperature was allowed to elevate to room temperature. The reaction solution was extracted by adding 300 ml of ethyl acetate and 250 ml of saturated aqueous sodium chloride. The ethyl acetate layer was washed with saturated aqueous sodium chloride and dried over anhydrous sodium sulfate, and the ethyl acetate was evaporated under reduced pressure. The residual crystals were stirred with 20 ml of ethyl acetate and dispersed by adding 150 ml of n-hexane. The crystals were collected by filtration, washed with n-hexane and dried to obtain 2.5 g of the desired product (yield: 36.7%).

Synthesis Method 4

10.0 g (0.0751 mol) of 5-amino-2,3-dihydro-1H-indene was stirred with 20 ml of methanol with cooling to 0° C. To the resulting solution, 38.8 ml of 47 wt % aqueous hydrobromic acid was added dropwise. After the dropwise addition, the resulting solution was stirred at 0° C., and 6.22 g (0.09 mol) of sodium nitrite in 10 ml of water was added dropwise while the temperature was maintained at 5° C. or below. After the dropwise addition, the reaction solution was stirred at 5° C. or below for 45 minutes to obtain a diazonium salt solution. 60 ml of 47% aqueous hydrobromic acid was mixed with 8.4 g of copper(II) bromide at room temperature with stirring. To the resulting solution, the diazonium salt solution was added dropwise, and after the dropwise addition, the resulting solution was stirred at room temperature for 1 hour and then stirred at 45° C. to 50° C. for 30 minutes with heating. The reaction solution was further stirred at 60° C. to 70° C. for 1 hour to complete the reaction. After the completion of the reaction, the reaction solution was extracted by adding 200 ml of ethyl acetate and 300 ml of water. The ethyl acetate layer was washed with saturated aqueous sodium chloride and neutralized and washed with saturated aqueous sodium hydrogen carbonate and dried over anhydrous sodium sulfate, and the ethyl acetate was evaporated under reduced pressure. The residue was purified by silica gel column chromatography (eluent: n-hexane) to isolate 6.15 g of the desired oily product (yield: 41.6%). 10 g (0.0507 mol) of 5-bromo-2,3-dihydro-1H-indene thus obtained was stirred with 50 ml of dry THF with cooling to −78° C. To the resulting solution, 38.5 ml of a 1.6 M n-butyllithium in n-hexane was added dropwise. After the dropwise addition, the resulting solution was stirred at −78° C. for 15 minutes, and then 10.4 g (0.10 mol) of trimethyl borate was added dropwise. After the dropwise addition, the resulting solution was stirred for 3 hours while the temperature was allowed to elevate to −20° C. Then, 60 ml of 1 M hydrochloric acid was added dropwise, and the reaction solution was stirred for 2 hours while the temperature was allowed to elevate to room temperature. The reaction solution was extracted by adding 300 ml of ethyl acetate and 250 ml of saturated aqueous sodium chloride. The ethyl acetate layer was washed with saturated aqueous sodium chloride, and the ethyl acetate was evaporated under reduced pressure. The residual crystals were dispersed in 200 ml of n-hexane, collected by filtration and dried to obtain 4.7 g of the desired product (yield: 57.2%).

(2) Synthesis of 5-(2,3-dihydro-1H-inden-5-yl)-4-methoxythiophene-3-carbonitrile

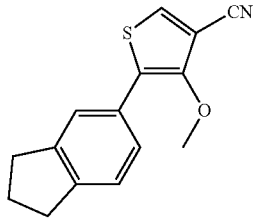 [SMILES: COc1c(C#N)csc1-c1ccc2c(c1)CCC2]

Synthesis was carried out in the same manner as in Synthesis Method 2 (4) in Reference Synthetic Example 3 by using 4.08 g (0.0252 mol) of (2,3-dihydro-1H-inden-5-yl) boronic acid described in Reference Synthetic Example 5(1) to obtain 5.0 g of the desired product (yield: 85.6%).

$^1$H-NMR (CDCl$_3$) δ: 2.07-2.15 (m, 2H), 2.92-2.97 (m, 4H), 3.91 (s, 3H), 7.26-7.28 (m, 1H), 7.41-7.43 (m, 1H), 7.49 (s, 1H), 7.69 (s, 1H).

(3) Synthesis of 1-[5-(2,3-dihydro-1H-inden-5-yl)-4-methoxythiophen-3-yl]ethanone

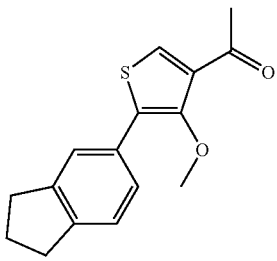 [SMILES: COc1c(C(C)=O)csc1-c1ccc2c(c1)CCC2]

Synthesis was carried out in the same manner as in Synthesis Method 2 (5) in Reference Synthetic Example 3 by using 4.5 g (0.0176 mol) of 5-(2,3-dihydro-1H-inden-5-yl)-4-methoxythiophene-3-carbonitrile to obtain 3.64 g of the desired product (yield: 75.8%).

$^1$H-NMR (CDCl$_3$) δ: 2.08-2.15 (m, 2H), 2.57 (s, 3H), 2.92-2.97 (m, 4H), 3.70 (s, 3H), 7.26-7.28 (m, 1H), 7.47-7.49 (m, 1H), 7.54 (s, 1H), 7.87 (s, 1H).

(4) Synthesis of 1-[5-(2,3-dihydro-1H-inden-5-yl)-4-hydroxythiophen-3-yl]ethanone Synthesis was carried out in the same manner as in Synthesis Method 2 (6) in Reference Synthetic Example 3 by using 3.5 g (0.0129 mol) of 1-[5-(2,3-dihydro-1H-inden-5-yl)-4-methoxythiophen-3-yl]ethanone to obtain 1.24 g of the desired product (yield: 37.3%).

$^1$H-NMR (CDCl$_3$) δ: 2.06-2.14 (m, 2H), 2.56 (s, 3H), 2.89-2.96 (m, 4H), 7.24-7.26 (m, 1H), 7.53-7.55 (m, 1H), 7.66 (s, 1H), 7.85 (s, 1H), 10.29 (s, 1H).

Reference Synthetic Example 6

2-(2,3-Dihydro-1H-inden-5-yl)-4-(1-hydrazonoethyl)thiophen-3-ol

Synthesis was carried out in the same manner as in Reference Synthetic Example 2 by using 1-[5-(2,3-dihydro-1H-inden-5-yl)-4-hydroxythiophen-3-yl]ethanone.

Morphology: yellow amorphous
LC/MS: condition 1 Retention time 4.82 (min)
LC/MS (ESI$^+$) m/z; 273 [M+1]$^+$ Reference Synthetic Example 7

1-[5-(2,3-Dihydrobenzofuran-5-yl)-4-hydroxythiophen-3-yl]ethanone (1) Synthesis of 5-(2,3-dihydro-benzofuran-5-yl)-4-methoxythiophene-3-carbonitrile

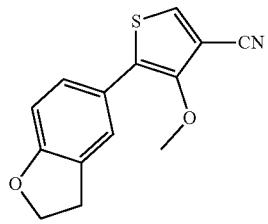 [SMILES: COc1c(C#N)csc1-c1ccc2c(c1)CCO2]

Synthesis was carried out in the same manner as in Synthesis Method 2 (4) in Reference Synthetic Example 3 by using 4.0 g (0.0244 mol) of (2,3-dihydrobenzofuran-5-yl) boronic acid to obtain 3.4 g of the desired product (yield: 60%).

$^1$H-NMR (CDCl$_3$) δ: 3.26 (t, J=8.7 Hz, 2H), 3.90 (s, 3H), 4.62 (t, J=8.7 Hz, 2H), 6.81-6.84 (m, 1H), 7.37-7.40 (m, 1H), 7.48 (s, 1H), 7.66 (s, 1H).

(2) Synthesis of 1-[5-(2,3-dihydro-benzofuran-5-yl)-4-methoxythiophen-3-yl]ethanone

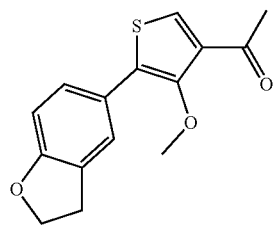 [SMILES: COc1c(C(C)=O)csc1-c1ccc2c(c1)CCO2]

Synthesis was carried out in the same manner as in Synthesis Method 2 (5) in Reference Synthetic Example 3 by using 2.6 g (0.0101 mol) of 5-(2,3-dihydro-benzofuran-5-yl)-4-methoxythiophene-3-carbonitrile to obtain 2.29 g of the desired product (yield: 87%).

$^1$H-NMR (CDCl$_3$) δ: 2.56 (s, 3H), 3.27 (t, J=8.7 Hz, 2H), 3.69 (s, 3H), 4.63 (t, J=8.7 Hz, 2H), 6.81-6.84 (m, 1H), 7.42-7.46 (m, 1H), 7.53 (s, 1H), 7.83 (s, 1H).

(3) Synthesis of 1-[5-(2,3-dihydro-benzofuran-5-yl)-4-hydroxythiophen-3-yl]ethanone Synthesis was carried out in the same manner as in Synthesis Method 2 (6) in Reference Synthetic Example 3 by using 1.58 g (0.0058 mol) of 1-[5-(2,3-dihydro-benzofuran-5-yl)-4-methoxythiophen-3-yl]ethanone to obtain the desired product (0.8 g yield: 53%).

$^1$H-NMR (CDCl$_3$) δ: 2.56 (s, 3H), 3.26 (t, J=8.7 Hz, 2H), 4.60 (t, J=8.7 Hz, 2H), 6.80-6.83 (m, 1H), 7.46-7.50 (m, 1H), 7.67 (s, 1H), 7.82 (s, 1H), 10.22 (s, 1H).

Reference Synthetic Example 8

2-(2,3-Dihydrobenzofuran-5-yl)-4-(1-hydrazonoethyl)thiophen-3-ol

Synthesis was carried out in the same manner as in Reference Synthetic Example 2 by using 1-[5-(2,3-dihydrobenzofuran-5-yl)-4-hydroxythiophen-3-yl]ethanone.

Morphology: yellow amorphous
LC/MS: condition 1 Retention time 4.30 (min)
LC/MS (ESI$^+$) m/z; 275 [M+1]$^+$
$^1$H-NMR (DMSO-d$_6$) δ: 2.09 (s, 3H), 3.19 (t, J=8.7 Hz, 2H), 4.49-4.55 (m, 2H), 6.52 (s, 2H), 6.74-6.78 (m, 1H), 7.42-7.45 (m, 2H), 7.58 (s, 1H), 12.18 (s, 1H).

The following formula (II) show the structures of the compounds obtained in Reference Synthetic Examples 1 to 8.

(II)

Ref Ex. 1
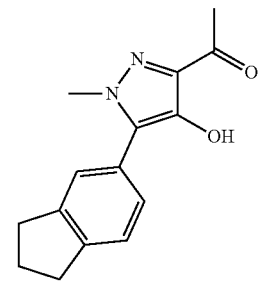

Ref Ex. 2
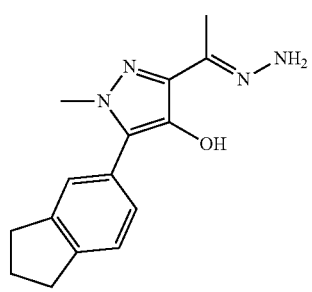

Ref Ex. 3
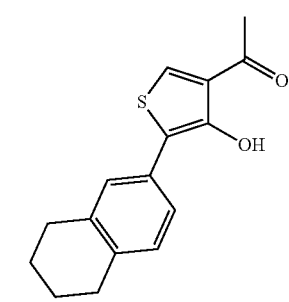

Ref Ex. 4
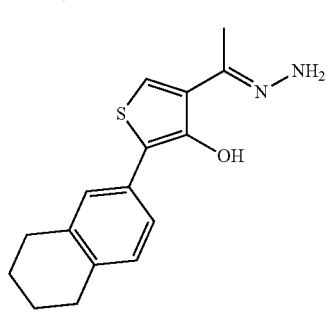

Ref Ex. 5
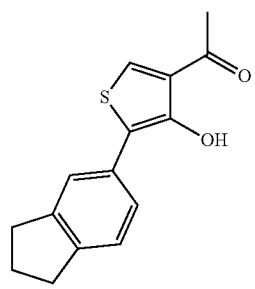

Ref Ex. 6
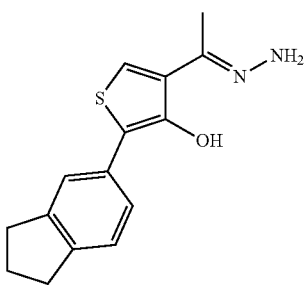

Ref Ex. 7
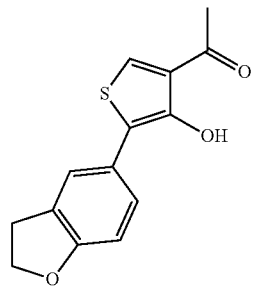

Ref Ex. 8
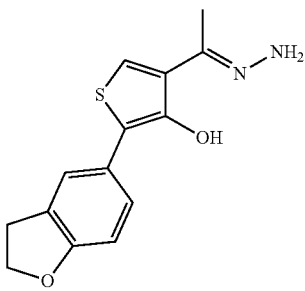

Reference Synthetic Example 9

5-(3-Isothiocyanatophenyl)-1H-tetrazole 1.18 g (10 mmol) in toluene (14 ml) was reacted with 0.85 g (13 mmol) of triethylamine hydrochloride and 1.79 g (13 mmol) of sodium azide at 100° C. for 25 hours. After cooling to room temperature, water (10 ml) was added to separate the reaction solution, and the aqueous layer was washed with ethyl acetate twice and concentrated. The resulting crude 3-(1H-tetrazol-5-yl)aniline (brown gum) was directly used for the subsequent reaction.

The crude 3-(1H-tetrazol-5-yl)aniline was mixed with dichloromethane (15 ml) and cooled to 0° C., and stirred with 2.8 ml (20 mmol) of triethylamine, 2.14 g (12 mmol) of 1,1'-thiocarbonyldiimidazole and N,N-dimethylformamide (5 mL) vigorously at 0° C. for 1 hour. Water (10 ml) was added, and concentrated hydrochloric acid was gradually added dropwise. The light brown solid precipitated at pH 6 to 7 was collected by filtration. Concentrated hydrochloric acid was gradually added dropwise, and the light brown solid precipitated at pH 5 was collected by filtration. The light brown solid was dried under reduced pressure to obtain the desired product (1.31 g, yield 64%, purity 86%).
Morphology: light brown solid
LC/MS: condition 1 Retention time 3.82 (min)
LC/MS (ESI$^+$) m/z; 204 [M+1]$^+$ Reference Synthetic Example 10

5-(4-Isothiocyanatophenyl)-1H-tetrazole

Synthesis was carried out in the same manner as in Reference Synthetic Example 9 by using 1.18 g (10 mmol) of 3-aminobenzonitrile to obtain the desired product (0.26 g, yield 13%, purity 90%).
Morphology: pale yellow solid
LC/MS: condition 1 Retention time 3.79 (min)
LC/MS (ESI$^+$) m/z; 204 [M+1]$^+$
LC/MS (ESI$^-$) m/z; 202 [M+1]$^+$ Reference Synthetic Example 11

4-(1H-Tetrazol-5-yl)benzohydrazide 1.16 g (10 mmol) of methyl 4-cyanobenzoate, 2.06 g (15 mmol) of triethylamine hydrochloride and 0.98 g (15 mmol) of sodium azide in toluene (20 ml) was allowed to react at 100° C. for 16 hours, and after cooling to room temperature, water (20 ml) was added, and the reaction solution was allowed to separate. Concentrated hydrochloric acid was added to the aqueous layer, and the precipitated colorless solid was collected by filtration through a Kiriyama funnel and dried under reduced pressure to obtain methyl 4-(1H-tetrazol-5-yl)benzoate (1.96 g, yield 96%).
0.20 g (0.99 mmol) of the 4-(1H-tetrazol-5-yl)benzoate was heated with ethanol (3.2 ml) and 0.84 g (16.8 mmol) of hydrazine monohydrate under reflux for 8.5 hours, and then the reaction solution was cooled to room temperature, and the precipitated pale yellow solid was collected by filtration through a Kiriyama funnel, washed with methanol and dried under reduced pressure to obtain the desired product (0.096 g, yield 47%, purity 99%).
Morphology: pale yellow solid
LC/MS: condition 1 Retention time 0.57 (min)
LC/MS (ESI$^+$) m/z; 205 [M+1]$^+$ Reference Synthetic Example 12

5-(Hydrazinecarbonyl)-N-[4-(2-hydroxyethylcarbamoyl)benzyl]thiophene-2-carboxamide (1) Synthesis of 4-[(tert-butoxycarbonylamino)methyl]benzoic acid 2.00 g (13.2 mmol) of 4-(aminomethyl)benzoic acid suspended in water (20 ml) was mixed with 3.81 g (27.6 mmol) of potassium carbonate and then with 3.57 g (16.4 mmol) of di-tert-butyl bicarbonate under cooling with ice. The mixture was allowed to react at 40° C. for 2.5 hours and stirred at room temperature overnight. Then, water (7 ml) and 5.6 g of citric acid monohydrate were gradually added, and the precipitated solid was collected by filtration, washed with water and dried under reduced pressure to obtain the desired product (3.05 g, yield 92%).

(2) Synthesis of tert-butyl 4-(2-hydroxyethylcarbamoyl)benzylcarbamate 2.06 g (8.21 mmol) of 4-[(tert-butoxycarbonylamino)methyl]benzoic acid suspended in 40 mL of methylene chloride was mixed with 1.63 g (10.1 mmol) of 1,1'-carbonyldiimidazole at room temperature and stirred at room temperature for 1.5 hours. The reaction solution was further stirred with 1.8 mL (30 mmol) of 2-aminoethanol overnight, and after addition of 40 mL of saturated aqueous sodium hydrogen carbonate, 20 mL of water and 200 mL of methylene chloride, was allowed to separate. The organic layer was washed with 80 mL of 1 M hydrochloric acid, with 40 mL of saturated aqueous sodium hydrogen carbonate and with 20 mL of saturated aqueous sodium chloride twice, dried over anhydrous sodium sulfate and filtered. The filtrate was concentrated under reduced pressure to obtain the desired product (2.30 g, yield 95%).

(3) Synthesis of methyl 5-[4-(2-hydroxyethylcarbamoyl)benzylcarbamoyl]thiophene-2-carboxylate 1.61 g (5.48 mmol) of tert-butyl 4-(2-hydroxyethylcarbamoyl)benzyl carbamate in 1,4-dioxane (20 ml) was stirred with 4 M hydrogen chloride/1,4-dioxane (20 ml) at room temperature overnight and concentrated under reduced pressure to obtain 4-(aminomethyl)-N-(2-hydroxyethyl)benzamide hydrochloride. After addition of saturated aqueous sodium hydrogen carbonate (48 ml), tetrahydrofuran (48 mL) and 1.15 g (5.60 mmol) of methyl 5-(chlorocarbonyl)thiophene-2-carboxylate (synthesized in accordance with WO2005100321), the reaction was carried out at room temperature for 7 hours. 100 mL of water was added to the reaction solution, and the precipitated solid was collected by filtration, washed with 50 mL of water and dried under reduced pressure to obtain the desired product (0.75 g, overall yield over two steps 38%).

(4) Synthesis of 5-hydrazinecarbonyl-N-[4-(2-hydroxyethylcarbamoyl)benzyl]thiophene-2-carboxamide 0.73 g (2.02 mmol) of methyl 5-[-(2-hydroxyethylcarbamoyl)benzylcarbamoyl]thiophene-2-carboxylate in 12 mL of ethanol was mixed with 1.67 mL (34.43 mmol) of hydrazine monohydrate and heated under reflux for 9 hours. The reaction solution was cooled with ice, and the precipitated solid was collected by filtration, washed with ethanol and dried under reduced pressure to obtain the desired product (0.68 g, yield 93%).

Morphology: colorless solid

LC/MS: condition 1 Retention time 2.99 (min)

LC/MS (ESI$^+$) m/z; 363 [M+1]$^+$

LC/MS (ESI$^-$) m/z; 361 [M+1]$^+$

The following formula (III) show the structures of the compounds obtained in Reference Synthetic Examples 9 to 12.

(III)

Ref Ex. 9

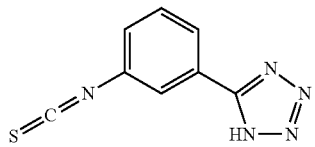

Ref Ex. 10

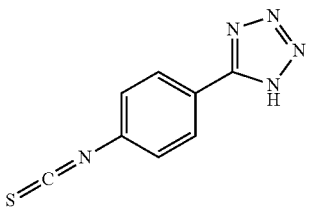

Ref Ex. 11

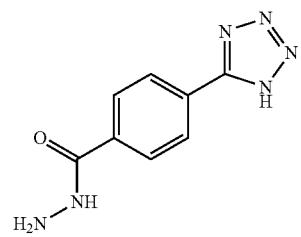

Ref Ex. 12

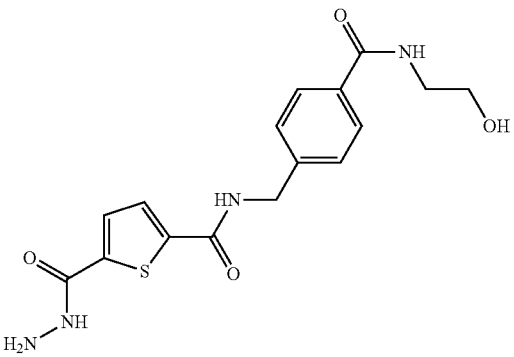

Synthetic Example 1

5-(2-{1-[5-(2,3-Dihydro-1H-inden-5-yl)-4-hydroxy-1-methyl-1H-pyrazol-3-yl]ethylidene}hydrazinecarbonyl)-N-(pyridin-4-ylmethyl)thiophene-2-carboxamide 1-[5-(2,3-Dihydro-1H-inden-5-yl)-4-hydroxy-1-methyl-1H-pyrazol-3-yl]ethanone (30 mg, 0.117 mmol) and 5-(hydrazinecarbonyl)-N-(pyridine-4-ylmethyl)thiophene-2-carboxamide (32 mg, 0.117 mmol, synthesized in accordance with WO2007010954) in dimethyl sulfoxide (0.9 mL) was heated at 100° C. for 3 days with stirring. After the reaction, the reaction solution was concentrated under reduced pressure. After addition of chloroform and ethyl acetate, the resulting crystals were collected by filtration and dried under reduced pressure to obtain the desired product (44 mg, 73% yield).

Morphology: pale yellow solid $^1$H-NMR (CDCl$_3$) δ: 2.06 (t, J=7.4 Hz, 2H), 2.44 (s, 3H), 2.93 (q, J=7.4 Hz, 4H), 3.31 (s, 3H), 4.50 (d, J=5.7 Hz, 2H), 7.25-7.40 (m, 5H), 7.86 (d, J=3.7 Hz, 1H), 8.00 (d, J=3.7 Hz, 1H), 8.51 (d, J=4.5 Hz, 2H), 9.33 (br s, 1H), 9.49 (s, 1H), 11.27 (s, 1H).

LC/MS: condition 1 Retention time 3.37, 3.50 (min)

LC/MS (ESI$^+$) m/z; 515 [M+1]$^+$

LC/MS (ESI$^-$) m/z; 513 [M-1]$^-$

Synthetic Examples 2 to 7

In Synthetic Examples 2 to 7, the compounds shown in the formula (IV) were synthesized in the same manner as in Synthetic Example 1. The yields and morphology of the resulting compounds, the LC/MS conditions used for their analysis and the observed peaks and retention times are shown in Table 2.

TABLE 2

| Syn. Ex. No. | Yield (%) | Morphology | LC/MS condition | Observed peak ESI$^+$ | Observed peak ESI$^-$ | Retention time (min) |
|---|---|---|---|---|---|---|
| 2 | 66 | Pale yellow solid | 1 | 529 | 527 | 3.47 |
| 3 | 82 | Pale yellow solid | 1 | 480 | 478 | 4.28, 4.40 |
| 4 | 95 | Pale yellow solid | 1 | 478 | 476 | 4.12, 4.30 |
| 5 | 100 | Yellow solid | 1 | 478 | 476 | 4.38, 4.53 |
| 6 | 94 | Yellow solid | 1 | 439 | 437 | 4.38, 4.53 |
| 7 | 67 | Pale yellow solid | 1 | 433 | 431 | 4.25, 4.53 |

Synthetic Example 8

Methyl 1-(2-{1-[5-(2,3-dihydro-1H-inden-5-yl)-4-hydroxy-1-methyl-1H-pyrazol-3-yl]ethylidene}hydrazinecarbonothioyl)piperidine-4-carboxylate 1-[5-(2,3-dihydro-1H-inden-5-yl)-4-hydroxyl-1-methyl-1H-pyrazol-3-yl]ethanone (50 mg, 0.195 mmol) and methyl 1-(hydrazinecarbonothioyl)piperidine-4-carboxylate (51 mg, 0.234 mmol, synthesized in accordance with WO2006062240) in N,N-dimethylformamide was stirred with concentrated hydrochloric acid (24 µL, 0.293 mmol) at room temperature for 1 day. After the reaction, ethyl acetate was added, and the reaction solution was washed with saturated aqueous ammonium chloride and saturated aqueous sodium chloride. The resulting organic layer was dried over anhydrous sodium sulfate and evaporated under reduced pressure. The resulting residue was purified by medium pressure silica gel column chromatography (hexane/ethyl acetate=1/1 (v/v)→ethyl acetate) to obtain the desired product (68 mg, 77% yield).

Morphology: pale yellow amorphous
LC/MS: condition 1 Retention time 4.50 (min)
LC/MS (ESI$^+$) m/z; 456 [M+1]$^+$
LC/MS (ESI$^-$) m/z; 454 [M−1]$^-$

Synthetic Example 9

1-(2-{1-[5-(2,3-Dihydro-1H-inden-5-yl)-4-hydroxy-1-methyl-1H-pyrazol-3-yl]ethylidene}hydrazinecarbonothioyl)piperidine-4-carboxylic acid Methyl 1-(2-{1-[5-(2,3-dihydro-1H-inden-5-yl)-4-hydroxy-1-methyl-1H-pyrazol-3-yl]ethylidene}hydrazinecarbonothioyl)piperidine-4-carboxylate (48 mg, 0.105 mmol) obtained in Synthetic Example 8 suspended in methanol was mixed with 1 M aqueous sodium hydroxide at room temperature and stirred at room temperature for 1 hour. After completion of the reaction, 1 M hydrochloric acid (0.32 mL) was added, an aqueous layer was extracted with chloroform three times, The resulting organic layer was dried over anhydrous sodium sulfate and evaporated under reduced pressure. The resulting residue was washed by suspending in hexane/ether and collected by filtration to obtain the desired product (32 mg, 69% yield).

Morphology: pale yellow amorphous
LC/MS: condition 1 Retention time 4.17 (min)
LC/MS (ESI$^+$) m/z; 442 [M+1]$^+$
LC/MS (ESI$^-$) m/z; 440 [M−1]$^-$

Synthetic Examples 10 to 12

In Synthetic Examples 10 to 12, the compounds shown in the formula (IV) were synthesized in the same manner as in Synthetic Example 9. The yields and morphology of the resulting compounds, the LC/MS conditions used for their analysis and the observed peaks and retention times are shown in Table 3.

TABLE 3

| Syn. Ex No. | Yield (%) | Morphology | LC/MS condition | Observed peak ESI$^+$ | Observed peak ESI$^-$ | Retention time (min) |
|---|---|---|---|---|---|---|
| 10 | 73 | Yellow solid | 1 | 425 | 423 | 4.07, 4.30 |
| 11 | 38 | Yellow solid | 1 | 419 | 417 | 3.94, 4.22 |
| 12 | 67 | Yellow solid | 1 | 464 | 462 | 4.20, 4.59 |

Synthetic Example 13

4-(2-{1-[5-(2,3-Dihydro-1H-inden-5-yl)-4-hydroxy-1-methyl-1H-pyrazol-3-yl]ethylidene}hydrazinecarbothioamido)benzoic acid 5-(2,3-Dihydro-1H-inden-5-yl)-3-(1-hydrazonoethyl)-1-methyl-1H-pyrazol-4-ol (47 mg, 0.174 mmol) in N,N-dimethylformamide (0.94 mL) was stirred with 4-isothiocyanatobenzoic acid (33 mg, 0.184 mmol) at room temperature for 4 hours and 40 minutes. After the reaction, 0.94 mL of water was added, and the resulting pale yellow solid was collected by filtration, washed with water and dried under reduced pressure to obtain the desired product (62 mg, 79% yield).

Morphology: pale yellow solid
LC/MS: condition 1 Retention time 4.25 (min)
LC/MS (ESI$^+$) m/z; 450 [M+1]$^+$
LC/MS (ESI$^-$) m/z; 448 [M−1]−

Synthetic Examples 14 to 15

In Synthetic Examples 14 to 15, the compounds shown in the formula (IV) were synthesized in the same manner as in Synthetic Example 13. The yields and morphology of the resulting compounds, the LC/MS conditions used for their analysis and the observed peaks and retention times are shown in Table 4.

TABLE 4

| Syn. Ex No. | Yield (%) | Morphology | LC/MS condition | Observed peak ESI$^+$ | Observed peak ESI$^-$ | Retention time (min) |
|---|---|---|---|---|---|---|
| 14 | 85 | Pale yellow solid | 1 | 450 | 448 | 4.25 |
| 15 | 58 | Pale yellow solid | 1 | 484, 486 | 482, 484 | 4.37 |

Synthetic Example 16

5-(2-{1-[4-Hydroxy-5-(5,6,7,8-tetrahydronaphthalen-2-yl)thiophen-3-yl]ethylidene}hydrazinecarbonyl)-N-[2-(pyridine-4-yl)ethyl]thiophene-2-carboxamide Synthesis was carried out in the same manner as in Synthetic Example 1 by using 1-[4-hydroxy-5-(5,6,7,8-tetrahydronaphthalen-2-yl)thiophen-3-yl]ethanone.

Yield: 62%
Morphology: pale yellow solid $^1$H-NMR (DMSO-$d_6$) δ: 1.72-1.77 (m, 4H), 2.47 (s, 3H), 2.71-2.75 (m, 4H), 2.87-2.91 (m, 2H), 3.51-3.57 (m, 2H), 7.07 (d, J=8.1 Hz, 1H), 7.27-7.29 (m, 2H), 7.47-7.49 (m, 2H), 7.75 (d, J=4.2 Hz, 1H), 7.95-7.98 (m, 2H), 8.47 (d, J=6.3 Hz, 2H), 8.80 (t, J=5.4 Hz, 1H), 11.33 (s, 1H), 12.07 (s, 1H).

LC/MS: condition 1 Retention time 3.95 (min)
LC/MS (ESI$^+$) m/z; 545 [M+1]$^+$
LC/MS (ESI$^-$) m/z; 543 [M−1]$^-$

Synthetic Example 17

3-(2-{1-[4-Hydroxy-5-(5,6,7,8-tetrahydronaphthalen-2-yl)thiophen-3-yl]ethylidene}hydrazinecarbothioamido)benzoic acid Synthesis was carried out in the same manner as in Synthetic Example 13 by using 4-(1-hydrazonoethyl)-2-(5,6,7,8-tetrahydronaphthalen-2-yl)thiophen-3-ol.

Yield: 80%
Morphology: pale yellow solid $^1$H-NMR (DMSO-$d_6$) δ: 1.73-1.74 (m, 4H), 2.39 (s, 3H), 2.70-2.74 (m, 4H), 7.07 (d, J=7.7 Hz, 1H), 7.43 (s, 1H), 7.49-7.51 (m, 2H), 7.73 (d, J=7.7 Hz, 1H), 7.92 (brs, 2H), 8.25 (s, 1H), 10.26 (s, 1H), 10.95 (s, 1H), 11.46 (brs, 1H), 13.01 (s, 1H).

LC/MS: condition 1 Retention time 4.78 (min)
LC/MS (ESI$^+$) m/z; 466 [M+1]$^+$
LC/MS (ESI$^-$) m/z; 464 [M−1]$^-$

Synthetic Examples 18 to 37

In Synthetic Examples 18 to 37, the compounds shown in the formula (V) were synthesized in the same manner as in Synthetic Example 1. The yields and morphology of the resulting compounds, the LC/MS conditions used for their analysis and the observed peaks and retention times are shown in Table 5. The NMR data are also shown for Synthetic Example 35.

TABLE 5

| Syn. Ex. No. | Yield (%) | Morphology | LC/MS condition | Observed peak ESI$^+$ | Observed peak ESI$^-$ | Retention time (min) |
|---|---|---|---|---|---|---|
| 18 | 60 | Yellow solid | 1 | 519 | 517 | 3.59 |
| 19 | 62 | Yellow solid | 1 | 533 | 531 | 3.54 |
| 20 | 48 | White solid | 1 | 484 | 482 | 4.63 |
| 21 | 44 | Pale yellow solid | 1 | 482 | 480 | 4.52 |
| 22 | 58 | Yellow solid | 1 | 482 | 480 | 4.77 |
| 23 | 68 | Yellow solid | 1 | 443 | 441 | 4.74 |
| 24 | 87 | Pale yellow solid | 1 | 437 | 435 | 4.67 |
| 25 | 62 | Yellow solid | 1 | 517 | 515 | 3.95 |
| 26 | 52 | Yellow solid | 1 | 531 | 529 | 3.85 |
| 27 | 23 | White solid | 1 | 482 | 480 | 5.05 |
| 28 | 77 | Pale yellow solid | 1 | 480 | 478 | 4.93 |
| 29 | 74 | Yellow solid | 1 | 480 | 478 | 5.15 |
| 30 | 68 | Yellow solid | 1 | 441 | 439 | 5.15 |
| 31 | 71 | Pale yellow solid | 1 | 435 | 433 | 5.10 |
| 32 | 38 | Yellow solid | 1 | 531 | 529 | 4.05 |
| 33 | 48 | White solid | 1 | 496 | 494 | 5.17 |
| 34 | 14 | White solid | 1 | 494 | 492 | 5.07 |
| 35 | 63 | Yellow solid | 1 | 494 | 492 | 5.27 |
| 36 | 69 | Yellow solid | 1 | 455 | 453 | 5.28 |
| 37 | 60 | Pale yellow solid | 1 | 449 | 447 | 5.25 |

Synthetic Example 35

$^1$H-NMR (DMSO-$d_6$) δ: 1.74-1.76 (m, 4H), 2.49 (s, 3H), 2.71-2.76 (m, 4H), 3.90 (s, 3H), 7.08 (d, J=8.1 Hz, 1H), 7.47-7.51 (m, 2H), 7.99 (s, 1H), 8.05 (d, J=8.4 Hz, 1H), 8.35 (d, J=8.1 Hz, 1H), 8.59 (s, 1H), 11.60 (s, 1H), 12.10 (s, 1H).

Synthetic Examples 38 to 43

In Synthetic Examples 38 to 43, the compounds shown in the formula (V) were synthesized in the same manner as in Synthetic Example 8. The yields and morphology of the resulting compounds and the observed peaks and retention times are shown in Table 6. The LC/MS analysis was carried out under condition 1 for these compounds. The NMR data are also shown for Synthetic Example 43.

TABLE 6

| Syn. Ex No. | Yield (%) | Morphology | Observed peak ESI+ | Observed peak ESI− | Retention time (min) |
|---|---|---|---|---|---|
| 38 | 100 | Pale yellow solid | 460 | 458 | 4.62 |
| 39 | 81 | Pale yellow solid | 488, 490 | 486, 488 | 4.55 |
| 40 | 94 | Pale yellow solid | 458 | 456 | 5.03 |
| 41 | 87 | Pale yellow solid | 486, 488 | 484, 486 | 4.95, 5.03 |
| 42 | 90 | Pale yellow solid | 472 | 470 | 5.13 |
| 43 | 84 | Pale yellow solid | 500, 502 | 498, 500 | 5.05, 5.20 |

Synthetic Example 43

$^1$H-NMR (DMSO-$d_6$) δ: 1.74 (s, 4H), 2.39 (s, 3H), 2.70-2.73 (m, 4H), 7.05-7.09 (m, 1H), 7.39-7.50 (m, 2H), 7.63-7.67 (m, 1H), 7.84-7.86 (m, 1H), 7.93 (s, 1H), 8.12 (s, 1H), 10.39 (s, 1H), 11.11 (s, 1H), 13.16 (s, 1H).

Synthetic Examples 44 to 55

In Synthetic Examples 44 to 55, the compounds shown in the formula (VI) were synthesized in the same manner as in Synthetic Example 9. The yields and morphology of the resulting compounds and the observed peaks and retention times are shown in Table 7. The LC/MS analysis was carried out under condition 1 for these compounds. The NMR data are also shown for Synthetic Example 50.

TABLE 7

| Syn. Ex No. | Yield (%) | Morphology | Observed peak ESI+ | Observed peak ESI− | Retention time (min) |
|---|---|---|---|---|---|
| 44 | 69 | Pale yellow solid | 446 | 444 | 4.30 |
| 45 | 54 | Yellow solid | 429 | 427 | 4.55 |
| 46 | 63 | Yellow solid | 423 | 421 | 4.37 |
| 47 | 41 | Yellow solid | 468 | 466 | 5.13 |
| 48 | 57 | Pale yellow solid | 444 | 442 | 4.70 |
| 49 | 50 | Yellow solid | 427 | 425 | 5.02 |
| 50 | 69 | Pale yellow solid | 421 | 419 | 4.80 |
| 51 | 41 | Yellow solid | 466 | 464 | 5.82 |
| 52 | 57 | White solid | 458 | 456 | 4.82 |
| 53 | 48 | Yellow solid | 441 | 439 | 5.13 |
| 54 | 45 | Yellow solid | 435 | 433 | 4.93 |
| 55 | 40 | Yellow solid | 480 | 478 | 6.00 |

Synthetic Example 50

$^1$H-NMR (DMSO-$d_6$) δ: 1.98-2.08 (m, 2H), 2.47 (s, 3H), 2.83-2.90 (m, 4H), 7.23-7.25 (m, 1H), 7.52-7.55 (m, 1H), 7.66 (s, 1H), 7.95 (s, 1H), 8.00-8.09 (m, 4H), 11.41 (s, 1H), 12.24 (s, 1H), 13.23 (s, 1H).

Synthetic Examples 56 to 60

In Synthetic Examples 56 to 60, the compounds shown in the formula (VI) were synthesized in the same manner as in Synthetic Example 13. The yields and morphology of the resulting compounds and the observed peaks and retention times are shown in Table 8. The LC/MS analysis was carried out under condition 1 for these compounds. The NMR data are also shown for Synthetic Example 57.

TABLE 8

| Syn. Ex. No. | Yield (%) | Morphology | Observed peak ESI+ | Observed peak ESI− | Retention time (min) |
|---|---|---|---|---|---|
| 56 | 82 | Pale yellow solid | 454 | 452 | 4.43 |
| 57 | 78 | Pale yellow solid | 454 | 452 | 4.43 |
| 58 | 79 | Pale yellow solid | 452 | 450 | 4.82 |
| 59 | 84 | Pale yellow solid | 452 | 450 | 4.82 |
| 60 | 78 | Pale yellow solid | 466 | 464 | 4.93 |

Synthetic Example 57

$^1$H-NMR (DMSO-$d_6$) δ: 2.38 (s, 3H), 3.22 (t, J=8.7 Hz, 2H), 4.54 (t, J=8.7 Hz, 2H), 6.79 (d, J=8.7 Hz, 1H), 7.46-7.51 (m, 2H), 7.65 (s, 1H), 7.71-7.74 (m, 1H), 7.86 (s, 1H), 7.90-7.95 (m, 1H), 8.24 (s, 1H), 10.25 (s, 1H), 10.94 (s, 1H), 13.00 (s, 1H).

Synthetic Example 61

N-[3-(1H-Tetrazol-5-yl)phenyl]-2-{1-[4-hydroxy-5-(5,6,7,8-tetrahydronaphthalen-2-yl)thiophen-3-yl]ethylidene}hydrazinecarbothioamide 4-(1-Hydrozonoethyl)-2-(5,6,7,8-tetrahydronaphthalen-2-yl)thiophen-3-ol (43 mg, 0.149 mmol) in N,N-dimethylformamide (3.0 mL) was mixed with 5-(3-isothiocyanatophenyl)-1H-tetrazole (30 mg, 0.149 mmol) at room temperature and stirred at room temperature for 2 days. After completion of the reaction, water was added, and the resulting solid was collected by filtration, washed with water and dried under reduced pressure to obtain the desired product (77 mg, 100% yield).

Morphology: pale yellow solid $^1$H-NMR (DMSO-$d_6$) δ: 1.74 (br.s, 4H), 2.40 (s, 3H), 2.70 (br.s, 4H), 7.07 (d, J=8.7 Hz, 1H), 7.43 (br.s, 1H), 7.49-7.51 (m, 1H), 7.58-7.64 (m, 1H), 7.81-7.95 (m, 4H), 8.35 (s, 1H), 10.33 (s, 1H), 11.01 (s, 1H).

LC/MS: condition 1 Retention time 4.96 (min)

LC/MS (ESI+) m/z; 490 [M+1]+

LC/MS (ESI−) m/z; 488 [M−1]−

Synthetic Examples 62 to 66

In Synthetic Examples 62 to 66, the compounds shown in the formula (VII) were synthesized in the same manner as in Synthetic Example 61. The yields and morphology of the resulting compounds, the LC/MS conditions used for their analysis and the observed peaks and retention times are shown in Table 9.

TABLE 9

| Syn. Ex. No. | Yield (%) | Morphology | LC/MS condition | Observed peak ESI$^+$ | Observed peak ESI$^-$ | Retention time (min) |
|---|---|---|---|---|---|---|
| 62 | 100 | Pale yellow solid | 1 | 490 | 488 | 4.86 |
| 63 | 97 | Pale yellow solid | 1 | 476 | 474 | 4.82 |
| 64 | 100 | Pale yellow solid | 1 | 476 | 474 | 4.74 |
| 65 | 84 | Pale yellow solid | 1 | 478 | 476 | 4.41 |
| 66 | 100 | Yellow solid | 1 | 478 | 476 | 4.29 |

Synthetic Example 67

N'-{1-[4-Hydroxy-5-(5,6,7,8-tetrahydronaphthalen-2-yl)thiophen-3-yl]ethylidene}4-(1H-tetrazol-5-yl)benzohydrazide 21.6 mg (0.0793 mmol) of 1-[4-hydroxy-5-(5,6,7,8-tetrahydronaphthalen-2-yl)thiophen-3-yl]ethanone and 17.9 mg (0.0877 mmol) of 4-(1H-tetrazol-5-yl)benzohydrazide in N,N-dimethylformamide (1.0 ml) was stirred with a drop of concentrated hydrochloric acid at 60° C. for 3 hours. After completion of the reaction, water was added, and the precipitated solid was collected by filtration, washed with chloroform (2.0 ml) and dried under reduced pressure to obtain the desired product (0.7 mg, yield 2%).

Morphology: yellow solid
LC/MS: condition 1 Retention time (5.11 min)
LC/MS (ESI$^+$) m/z; 459 [M+1]$^+$
LC/MS (ESI$^-$) m/z; 457 [M−1]$^-$

Synthetic Example 68

In Synthetic Example 68, the compound shown in the formula (VII) was synthesized in the same manner as in Synthetic Example 67. The yield and morphology of the resulting compound, the LC/MS condition used for its analysis and the observed peaks and retention time are shown in Table 10.

TABLE 10

| Syn. Ex No. | Yield (%) | Morphology | LC/MS condition | Observed peak ESI$^+$ | Observed peak ESI$^-$ | Retention time (min) |
|---|---|---|---|---|---|---|
| 68 | 20 | Yellow solid | 1 | 445 | 443 | 4.94 |

Synthetic Example 69

5-(2-{1-[4-Hydroxy-5-(5,6,7,8-tetrahydronaphthalen-2-yl)thiophen-3-yl]ethylidene}hydrazinecarbonyl)-N-[4-(2-hydroxyethylcarbamoyl)benzyl]thiophene-2-carboxamide Synthesis was carried out in the same manner as in Synthetic Example 1 by using 24.4 mg (0.0895 mmol) of 1-[4-hydroxy-5-(5,6,7,8-tetrahydronaphthalen-2-yl)thiophen-3-yl]ethanone and 32.6 mg (0.0900 mmol) of 5-(hydrazinecarbonyl)-N-[4-(2-hydroxyethylcarbamoyl)benzyl]thiophene-2-carboxamide to obtain the desired product (35.8 mg, yield 65%).

Morphology: yellow solid
LC/MS: condition 1 Retention time (4.62 min)
LC/MS (ESI$^+$) m/z; 617 [M+1]$^+$
LC/MS (ESI$^-$) m/z; 615 [M−1]$^-$ Synthetic Examples 70 to 71

In Synthetic Examples 70 to 71, the compounds shown in the formula (VII) were synthesized in the same manner as in Synthetic Example 69. The yields and morphology of the resulting compounds, the LC/MS conditions used for their analysis and the observed peaks and retention times are shown in Table 11.

TABLE 11

| Syn. Ex. No. | Yield (%) | Morphology | LC/MS condition | Observed peak ESI$^+$ | Observed peak ESI$^-$ | Retention time (min) |
|---|---|---|---|---|---|---|
| 70 | 64 | Yellow solid | 1 | 603 | 601 | 4.07 |
| 71 | 59 | Yellow solid | 1 | 605 | 603 | 4.11 |

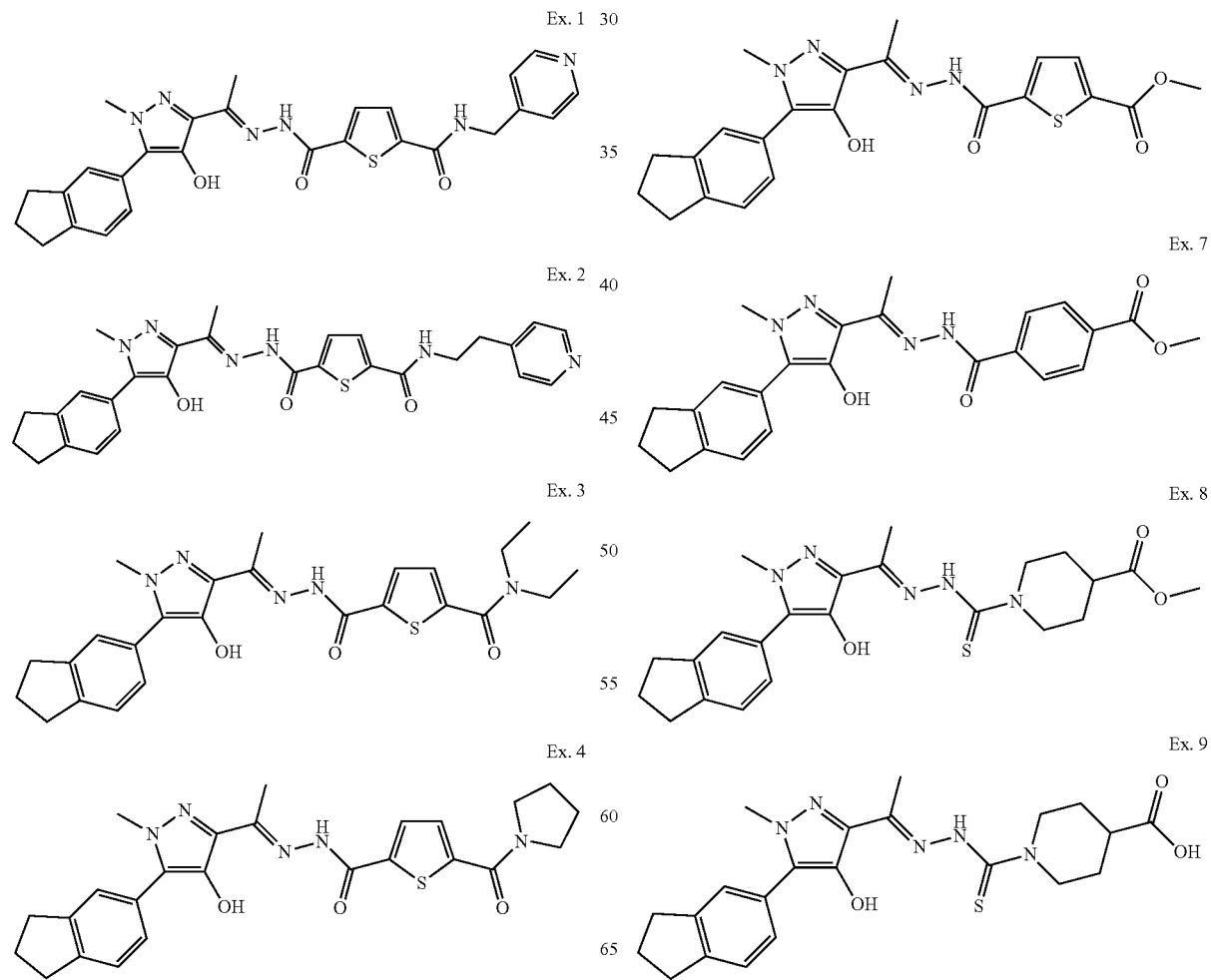

Ex. 10
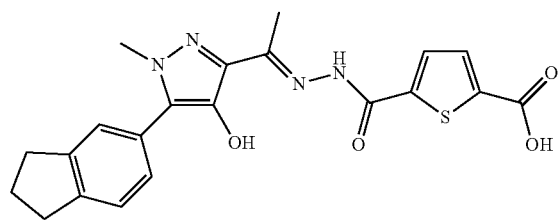
Ex. 11
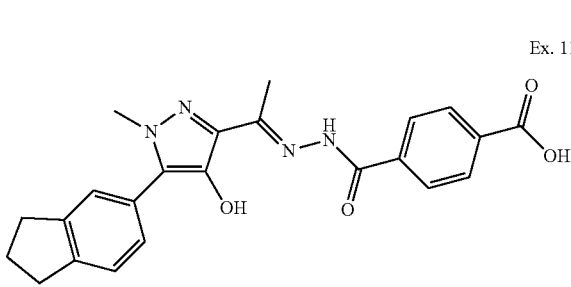
Ex. 12
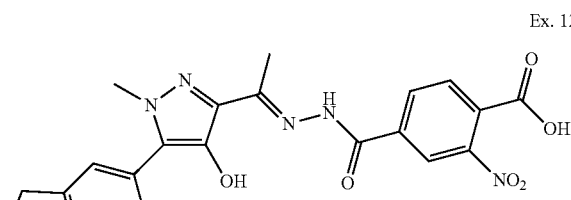
Ex. 13
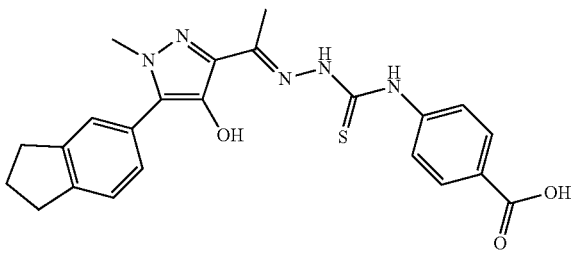
Ex. 14
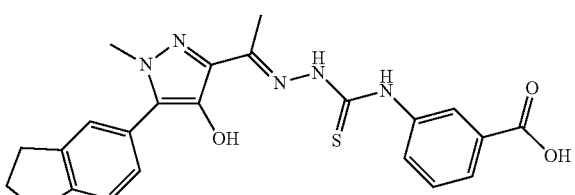
Ex. 15
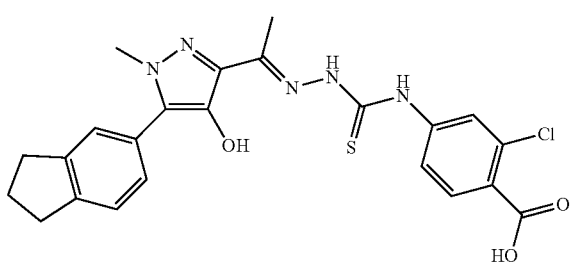
Ex. 16
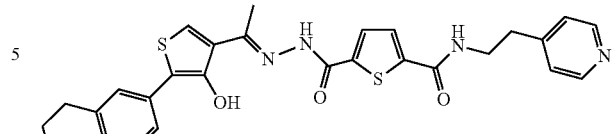
Ex. 17
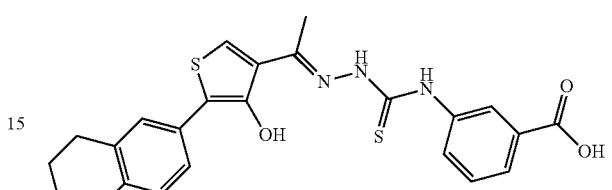
(V)
Ex. 18
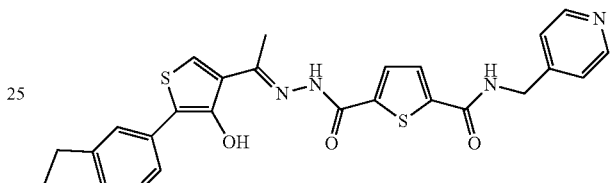
Ex. 19
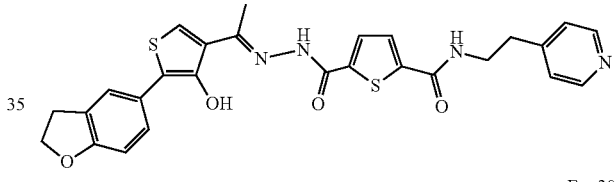
Ex. 20
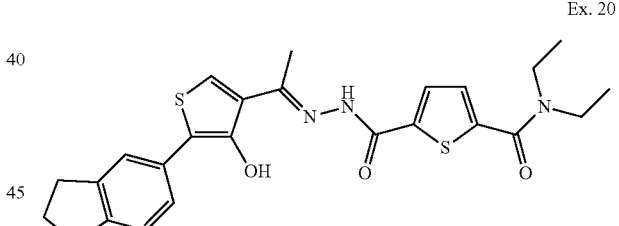
Ex. 21
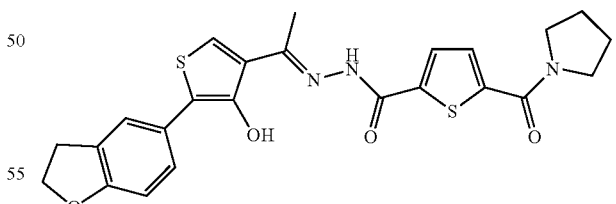
Ex. 22
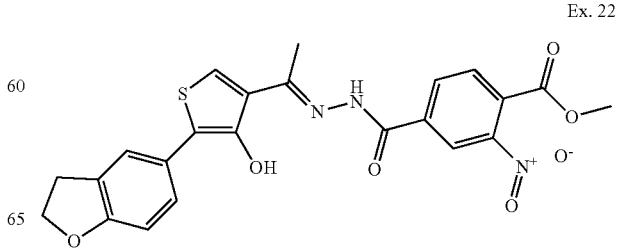

Ex. 23
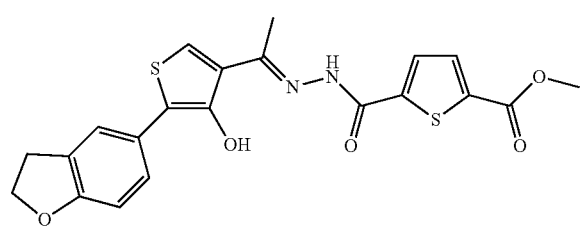
Ex. 24
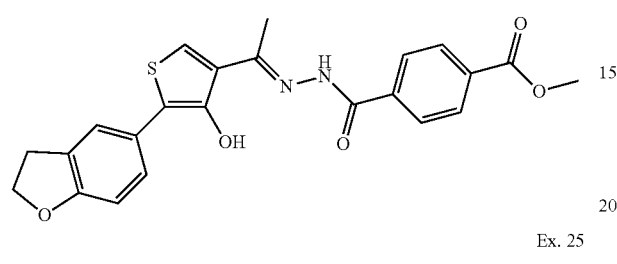
Ex. 25
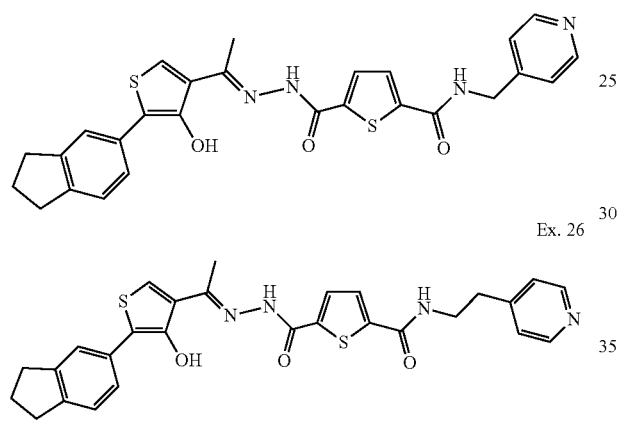
Ex. 26
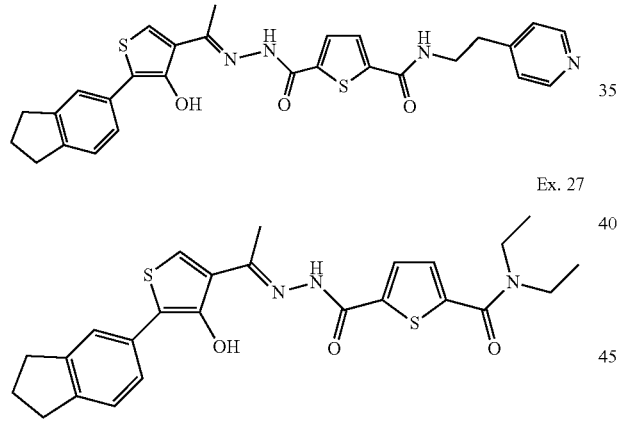
Ex. 27
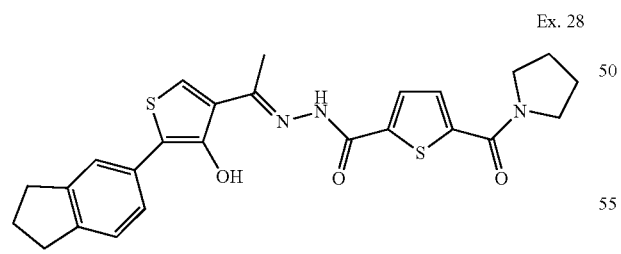
Ex. 28
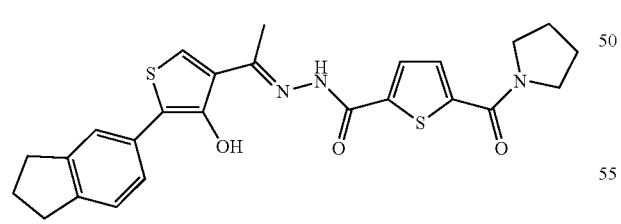
Ex. 29
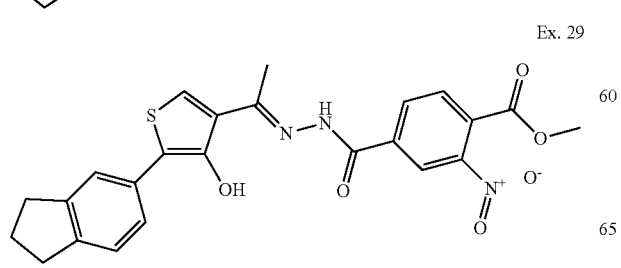
Ex. 30
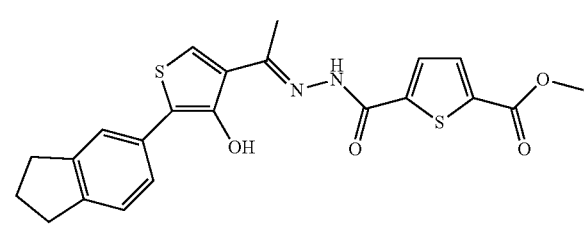
Ex. 31
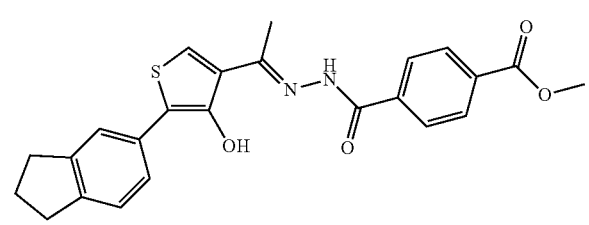
Ex. 32
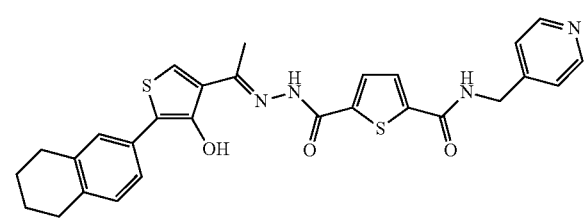
Ex. 33
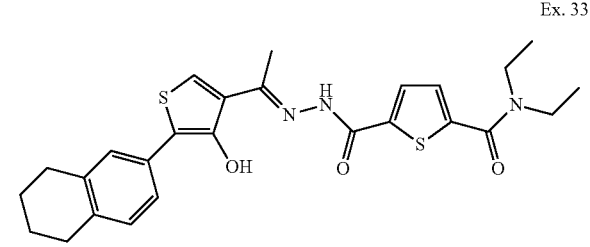
Ex. 34
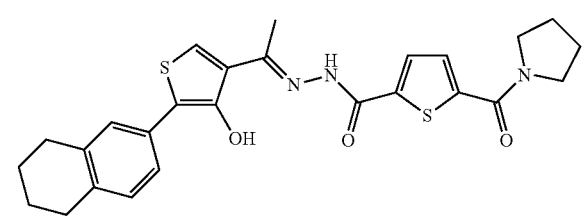
Ex. 35
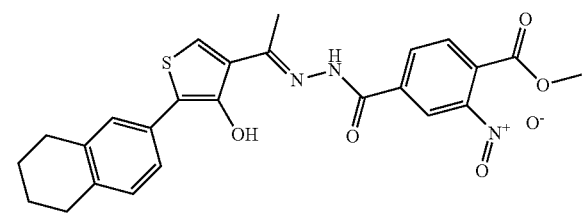

Ex. 36
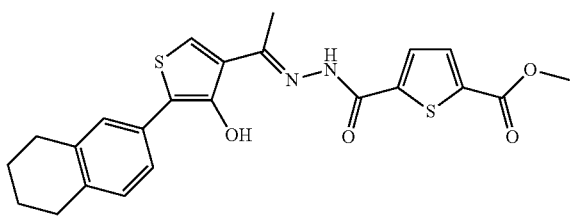
Ex. 37
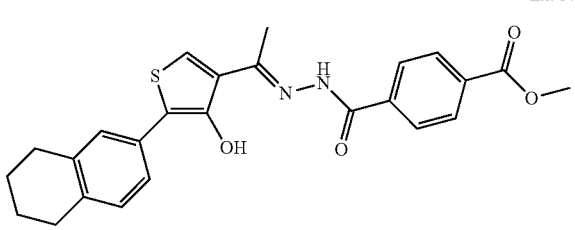
Ex. 38
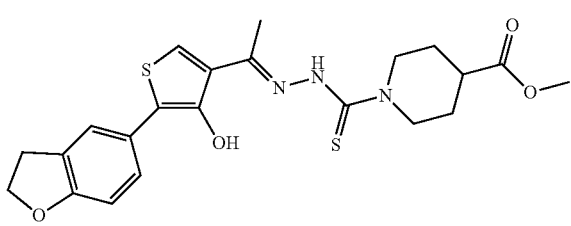
Ex. 39
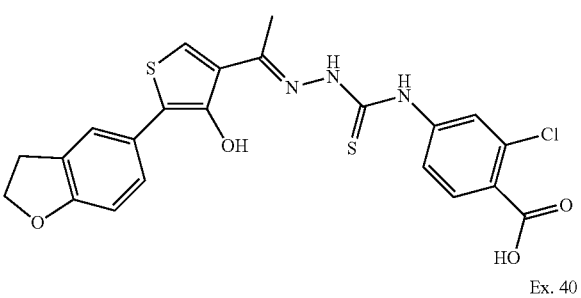
Ex. 40
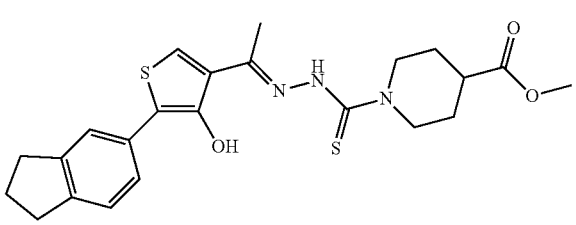
Ex. 41
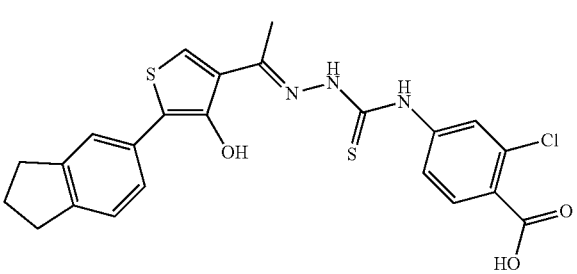
Ex. 42
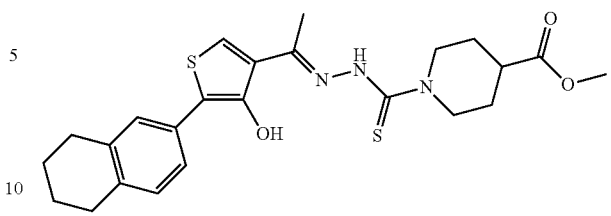
Ex. 43
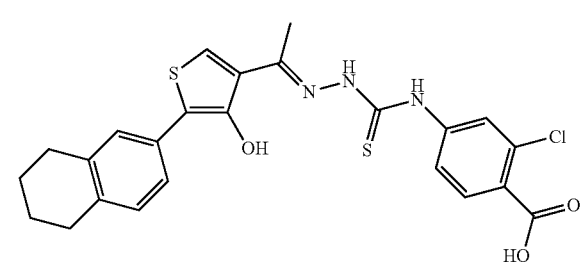
(VI)
Ex. 44
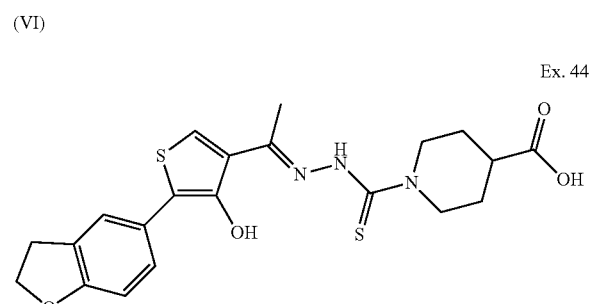
Ex. 45
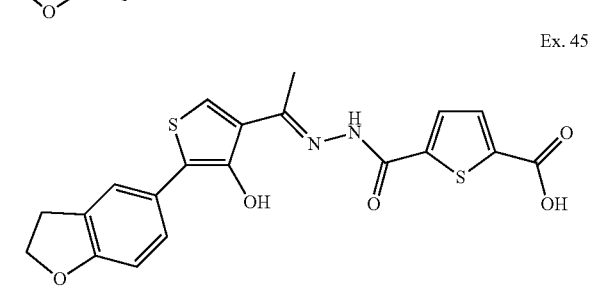
Ex. 46
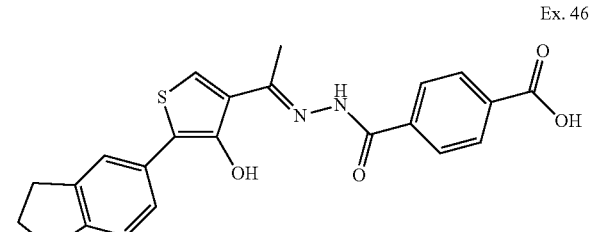
Ex. 47
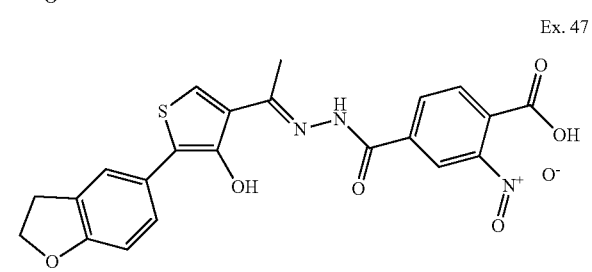

Ex. 48
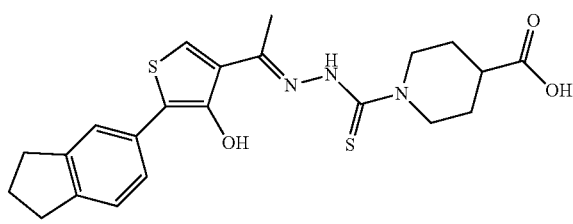
Ex. 49
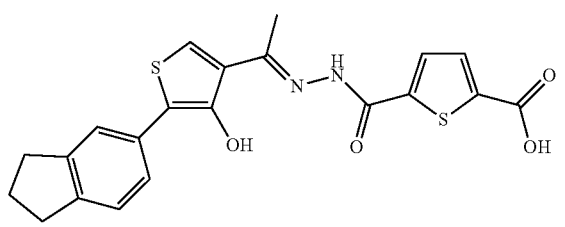
Ex. 50
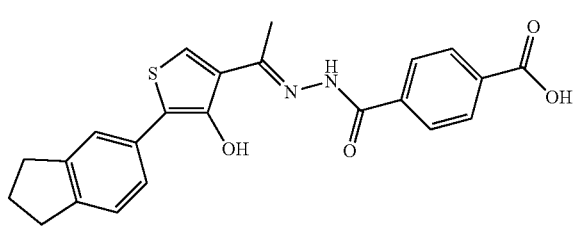
Ex. 51
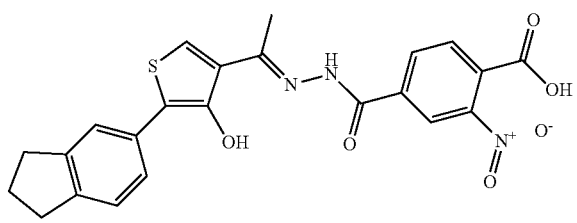
Ex. 52
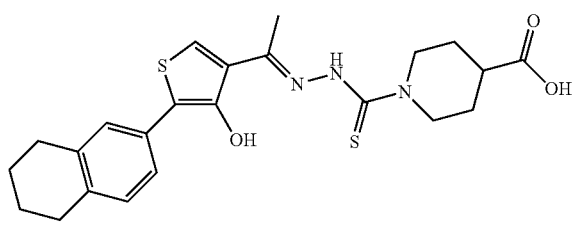
Ex. 53
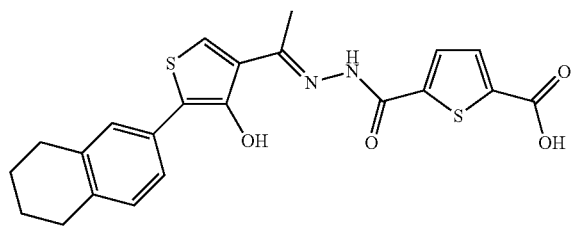
Ex. 54
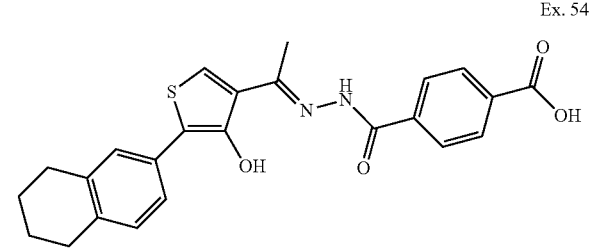
Ex. 55
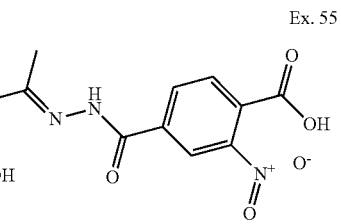
Ex. 56
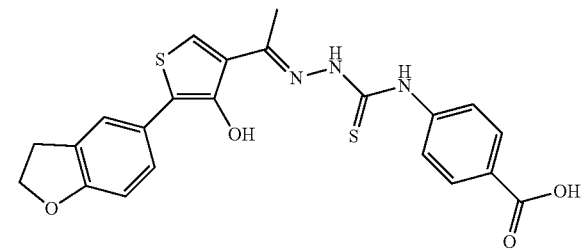
Ex. 57
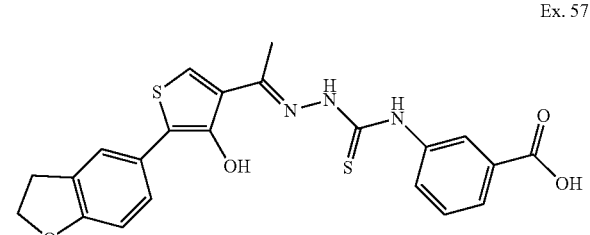
Ex. 58
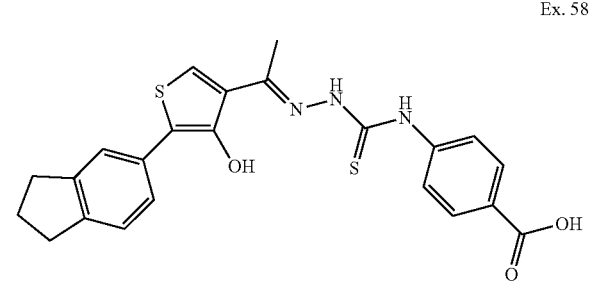
Ex. 59
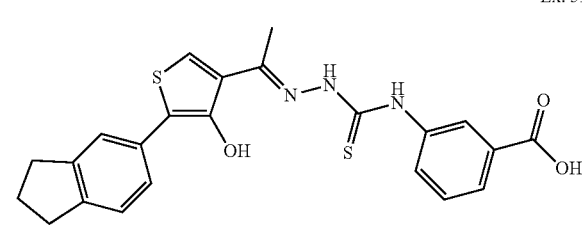

Ex. 60
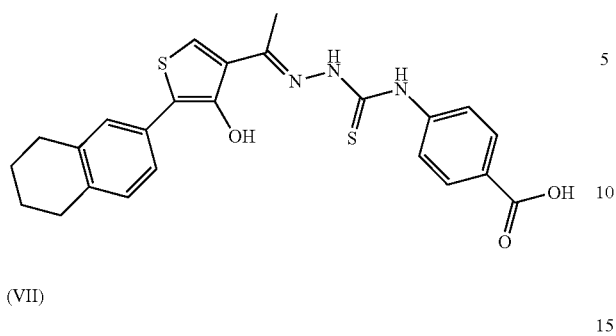
(VII)
Ex. 61
Ex. 62
Ex. 63
Ex. 64
Ex. 65
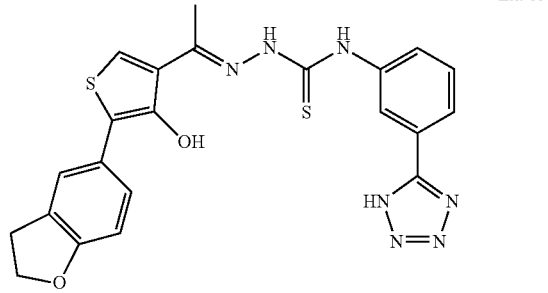
Ex. 66
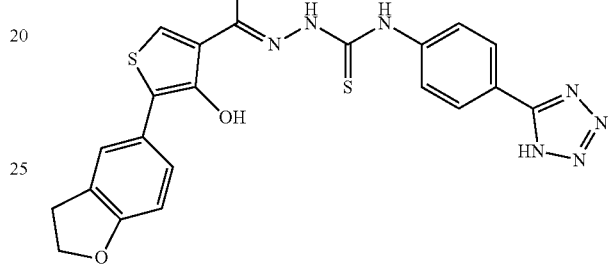
Ex. 67
Ex. 68

-continued

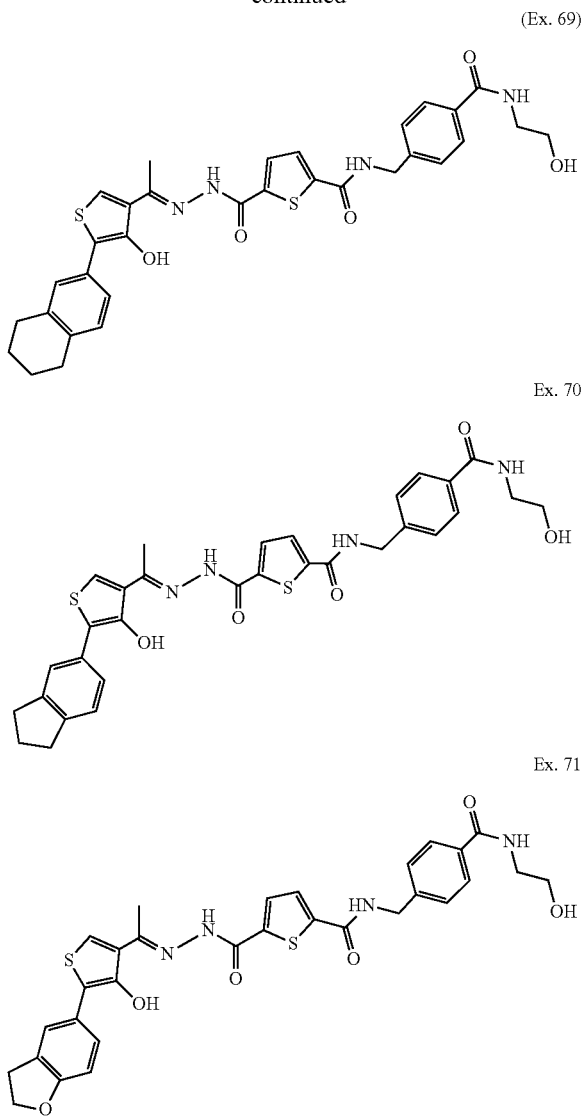

(Ex. 69)

Ex. 70

Ex. 71

Assay Example 1

Stimulation of Proliferation of a
Thrombopoietin-Dependent Cell Line

The responses of thrombopoietin receptor to the compounds of Synthetic Examples of the present invention were assayed using a human leukemic cell line, UT7/EPO-mpl.

(1) Cells and Cell Culture

UT7/EPO-mpl is a stable transformed cell line obtained by introducing into human leukemic cell line UT7/EPO a vector that induces expression of human thrombopoietin receptor (c-mpl) under control of cytomegalovirus immediate-early promoter by the method of Takatoku et al. (J. Biol. Chem., 272:7259-7263 (1997)). Proliferation of this cell line is stimulated by TPO, while its mother cell line UT7/EPO exhibits no response to TPO. These two cell lines were subcultured in IMDM (Invitrogen) containing 10% fetal bovine serum (Thermo Electron or BioWest) using a $CO_2$ incubator (5% $CO_2$, 37° C.).

(2) Cell Proliferation Assay

The subcultured cells described above were washed twice with PBS and suspended in IMDM containing 10% fetal bovine serum at a cell density of $6 \times 10^4$ cells/ml. The cell suspension was transferred to a 96-well tissue culture plate (CORNING) in 100-μl aliquots. Then either thrombopoietin (Pepro Tech EC) or the compound of Synthetic Examples dissolved in dimethyl sulfoxide were diluted 83-fold with IMDM containing 10% fetal bovine serum and added to the aforementioned cell suspension in 20-μl aliquots. The cell suspension was incubated in a $CO_2$ incubator (5% $CO_2$, 37° C.) for 4 days. Cell proliferation was assayed using WST-8 reagent (Kishida Chemical Co., Ltd.) according to instructions by the manufacturer. A 10-μl aliquot of 5 mM WST-8 reagent solution was added to each well of the tissue culture plate, and the plate was incubated at 37° C. for 4 hours. The formazan pigment generated was detected by measuring the absorbance at 450 nm with a 96-well microplate reader (Nihon Molecular Devices, Spectramax 190). Proliferation of thrombopoietin-responsive UT7/EPO-mpl cells was stimulated by the compounds of the Synthetic Examples in a concentration-dependent manner, while no effect of this compounds on proliferation was observed with UT7/EPO, the mother cell line. These results indicate that the compound of the Synthetic Examples of the present invention acts on the thrombopoietin receptor selectively as an activator.

The concentration of each compound that yields a growth rate corresponding to 50% of the growth of human leukemic cell line UT-7/EPO-mpl observed in the presence of 10 ng/mL TPO ($EC_{50}$) in the test on the compounds of the Synthetic Examples in Assay Example 1 are shown in Tables 12 and 13.

TABLE 12

| Syn. Ex. No. | $EC_{50}$ (ng/mL) |
|---|---|
| 1 | 0.8 |
| 2 | 1.8 |
| 3 | 33.7 |
| 4 | 5.3 |
| 5 | 5.6 |
| 6 | 8.3 |
| 7 | 18.6 |
| 8 | 45.3 |
| 9 | 33.8 |
| 10 | 19.3 |
| 11 | 24.1 |
| 12 | 0.8 |
| 13 | 26.6 |
| 14 | 10.2 |
| 15 | 6.2 |
| 16 | 0.27 |
| 17 | 23.0 |
| 18 | 2.8 |
| 19 | 16.0 |
| 21 | 48.0 |
| 25 | 0.27 |
| 26 | 0.46 |
| 27 | 3.1 |
| 28 | 2.8 |
| 29 | 6.2 |
| 30 | 8.3 |
| 31 | 23.0 |
| 32 | 0.24 |
| 33 | 2.4 |
| 34 | 1.2 |
| 35 | 5.4 |
| 36 | 4.3 |
| 37 | 18.0 |
| 39 | 21.0 |
| 40 | 24.0 |
| 41 | 3.3 |
| 42 | 23.0 |

TABLE 12-continued

| Syn. Ex. No. | $EC_{50}$ (ng/mL) |
|---|---|
| 43 | 2.4 |
| 46 | 40.0 |
| 47 | 26.0 |
| 48 | 1.8 |
| 49 | 1.4 |
| 50 | 0.74 |
| 51 | 0.21 |
| 52 | 1.7 |
| 53 | 0.55 |
| 54 | 1.3 |
| 55 | 0.19 |
| 56 | 26.0 |
| 58 | 2.6 |
| 59 | 24.0 |
| 60 | 2.7 |

TABLE 13

| Syn. Ex. No. | $EC_{50}$ (ng/mL) |
|---|---|
| 61 | 2.0 |
| 62 | 2.0 |
| 63 | 1.9 |
| 64 | 2.1 |
| 65 | 2.7 |
| 66 | 4.2 |
| 67 | 2.4 |
| 68 | 10.0 |
| 69 | 0.22 |
| 70 | 0.23 |
| 71 | 2.4 |

Assay Example 2

The biokinetics of the compounds of the present invention as a drug can be assayed in accordance with Assay Example 2 in WO2007/010954.

The compounds of the present invention show good biokinetics as a drug.

Assay Example 3

Megakaryocyte Colony Stimulating Activity

The action of the compounds of the present invention on the proliferation, differentiation and maturation of megakaryocyte cells can be measured by the megakaryocyte colony assay using human bone marrow cells in accordance with Assay Example 3 in WO2007/010954.

The compounds of the present invention have excellent megakaryocyte colony stimulating activity and increase platelets through the activity.

Assay Example 4

Increase in Nuclear Ploidy

The activities of the compounds of the Synthetic Examples on the nuclear ploidy of megakaryocytes from human hematopoietic progenitor cells and/or platelet production from megakarycytes differentiated from human hematopoietic progenitor cells can be evaluated in accordance with Yamane, Nakamura et al. (Blood, 112:542-550 (2008)).

The compounds of the present invention show good megakaryocyte maturation activity and/or platelet increasing activity in an assay of maturity of megakaryocytes from human hetatopoietic progenitor cells based on nuclear ploidy of megakaryocytes and/or an assay of platelet production from megakaryocytes.

Formulation Example 1

A granule preparation containing the following ingredients is prepared.

| Ingredients | |
|---|---|
| Compound represented by the formula (I) | 10 mg |
| Lactose | 700 mg |
| Corn Starch | 274 mg |
| HPC-L | 16 mg |
| | 1000 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated (extrusion granulation, die size 0.5-1 mm) and dried. The resulting dry granules are sifted through a shaking sieve (12/60 mesh) to obtain a granule preparation.

Formulation Example 2

A powder preparation for capsulation containing the following ingredients is prepared.

| Ingredients | |
|---|---|
| Compound represented by the formula (I) | 10 mg |
| Lactose | 79 mg |
| Corn Starch | 10 mg |
| Magnesium Stearate | 1 mg |
| | 100 mg |

A compound represented by the formula (I) and lactose are sifted through a 60-mesh sieve. Corn starch is sifted though a 120-mesh sieve. They are mixed with magnesium stearate in a V-type blender. The 10% powder is put in hard gelatin capsules No. 5, 100 mg each.

Formulation Example 3

A granule preparation for capsulation containing the following ingredients is prepared.

| Ingredients | |
|---|---|
| Compound represented by the formula (I) | 15 mg |
| Lactose | 90 mg |
| Corn Starch | 42 mg |
| HPC-L | 3 mg |
| | 150 mg |

A compound represented by the formula (I) and lactose are sifted through a 60-mesh sieve. Corn starch is sifted though a 120-mesh sieve. They are mixed in a V-type blender. The powder mixture is kneaded with a low-viscosity hydroxypropylcellulose (HPC-L) aqueous solution, granulated and dried.

The resulting dry granules are sifted through a shaking sieve (12/60 mesh). The granules are put in hard capsules No. 4, 150 mg each.

Formulation Example 4

A tablet preparation containing the following ingredients is prepared.

| Ingredients | |
|---|---|
| Compound represented by the formula (I) | 10 mg |
| Lactose | 90 mg |
| Microcrystalline cellulose | 30 mg |
| Magnesium Stearate | 5 mg |
| CMC-Na | 15 mg |
| | 150 mg |

A compound represented by the formula (I), lactose, microcrystalline cellulose and CMC-Na (carboxymethylcellulose sodium salt) are sifted through a 60-mesh sieve and mixed. The powder mixture is mixed with magnesium stearate to give a bulk powder mixture. The powder mixture is compressed directly into 150 mg tablets.

Formulation Example 5

An intravenous preparation is prepared as follows.

| Compound represented by the formula (I) | 100 mg |
|---|---|
| Saturated Fatty Acid Glyceride | 1000 mL |

Solutions having the above-mentioned composition are usually administered to a patient intravenously at a rate of 1 mL per 1 minute.

INDUSTRIAL APPLICABILITY

The fused heterocyclic compounds of the present invention stiulate differentiation and proliferation of hematopoietic stem cells, megakaryocytic progenitor cells and megakaryocytes, increase platelets, stimulate differentiation and proliferation of vascular endothelial cells and ehdothelical progenitor cells, have anti-arteriosclerosis action, are effective for therapeutic angeogenesis and useful as an ingredient of preventive, therapeutic and improving agents for diseases against which activation of the thrombopoietin receptor.

The entire disclosures of Japanese Patent Application No. 2009-244852 filed on Oct. 23, 2009 and Japanese Patent Application No. 2010-181032 filed on Aug. 12, 2010 including specifications, claims and summaries are incorporated herein by reference in their entireties.

The invention claimed is:
1. A compound of formula (I):

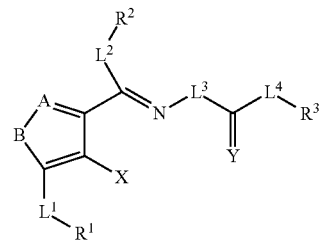

a tautomer, or a pharmaceutically acceptable salt of the compound,
wherein:
A is CH;
B is a sulfur atom;
$R^1$ is an indanyl group;
$L^1$ and $L^2$ are single bonds;
$L^3$ is NH;
X is OH;
$R^2$ is a hydrogen atom or a $C_{1-6}$ alkyl group; and
either
$L^4$ is a single bond; Y is an oxygen atom; and $R^3$ is a thienyl group substituted with a substituent selected from the group consisting of a carboxy group and a $C_{1-6}$ alkoxycarbonyl group or $R^3$ is a phenyl group substituted with a carboxy group or a $C_{1-6}$ alkoxycarbonyl group and optionally further substituted with a nitro group;
or
$L^4$ is NH; Y is a sulfur atom; and $R^3$ is a phenyl group substituted with a carboxy group or a $C_{1-6}$ alkoxycarbonyl group and optionally further substituted with a halogen group.

2. A composition, comprising:
the compound of claim 1, a tautomer, or a pharmaceutically acceptable salt of the compound, and
a pharmaceutically acceptable carrier.

3. The compound of claim 1, which is selected from the group consisting of

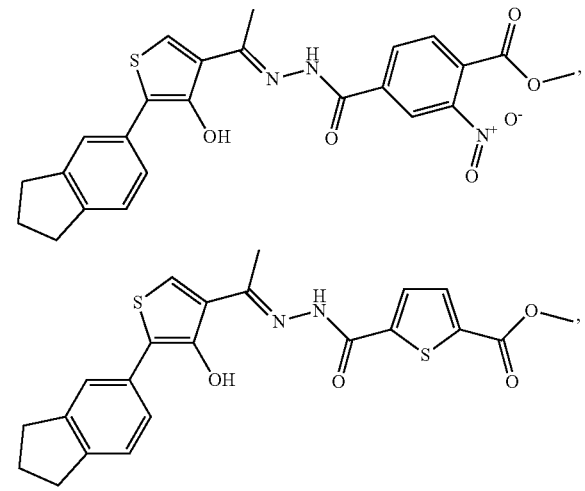

-continued
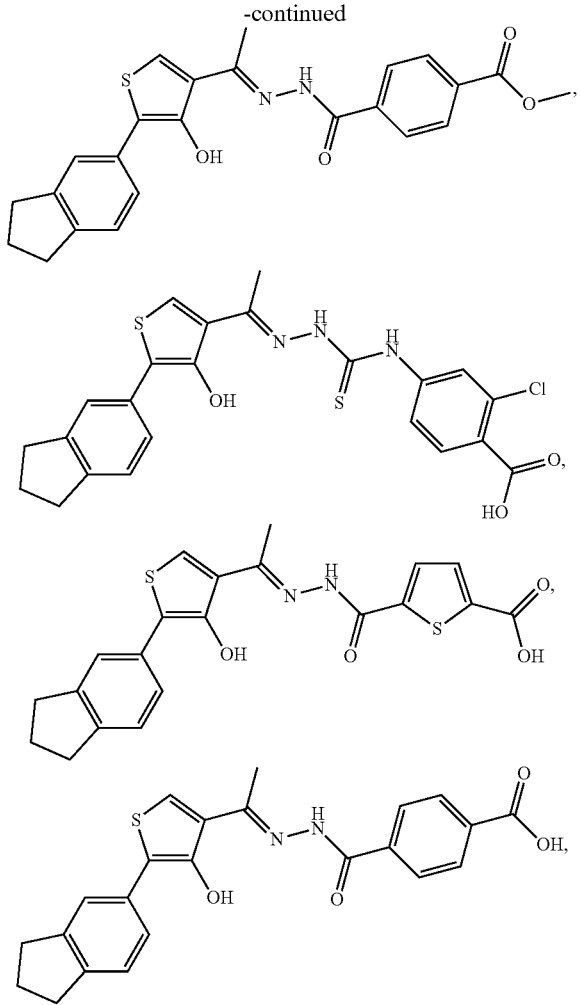
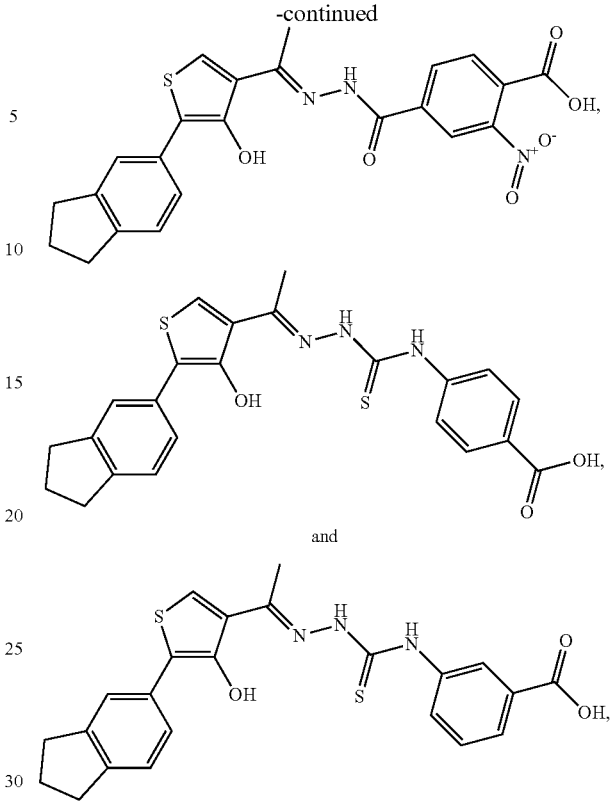
a tautomer, or a pharmaceutically acceptable salt of the compound.
4. A composition, comprising:
the compound of claim 3, a tautomer, or a pharmaceutically acceptable salt of the compound, and
a pharmaceutically acceptable carrier.
* * * * *